(12) United States Patent
Fernstrom et al.

(10) Patent No.: US 9,198,621 B2
(45) Date of Patent: Dec. 1, 2015

(54) METHOD, APPARATUS AND SYSTEM FOR FOOD INTAKE AND PHYSICAL ACTIVITY ASSESSMENT

(75) Inventors: John D. Fernstrom, Pittsburgh, PA (US); Madelyn H. Fernstrom, Pittsburgh, PA (US); Robert J. Sclabassi, Gibsonia, PA (US); Mingui Sun, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1884 days.

(21) Appl. No.: 12/141,741

(22) Filed: Jun. 18, 2008

(65) Prior Publication Data

US 2009/0012433 A1 Jan. 8, 2009

Related U.S. Application Data

(60) Provisional application No. 60/936,083, filed on Jun. 18, 2007, provisional application No. 60/949,033, filed on Jul. 11, 2007.

(51) Int. Cl.
| | |
|---|---|
| *A61B 5/00* | (2006.01) |
| *A61B 5/11* | (2006.01) |
| *G06K 9/00* | (2006.01) |
| *A61B 5/145* | (2006.01) |

(52) U.S. Cl.
CPC ............ *A61B 5/7264* (2013.01); *A61B 5/0022* (2013.01); *A61B 5/1112* (2013.01); *A61B 5/1123* (2013.01); *A61B 5/1128* (2013.01); *A61B 5/411* (2013.01); *G06K 9/00335* (2013.01); *G06K 9/00771* (2013.01); *A61B 5/145* (2013.01); *A61B 5/6822* (2013.01); *A61B 5/7232* (2013.01); *A61B 2503/06* (2013.01); *A61B 2505/07* (2013.01); *A61B 2562/0219* (2013.01); *G06K 2209/17* (2013.01)

(58) Field of Classification Search
CPC . G06K 9/00; G06K 9/00496; G06K 2209/00; G06K 2209/17; A61B 5/00
See application file for complete search history.

(56) References Cited

U.S. PATENT DOCUMENTS

| | | | |
|---|---|---|---|
| 3,069,654 A | 12/1962 | Hough | |
| 4,823,808 A | 4/1989 | Clegg et al. | |
| 5,640,635 A * | 6/1997 | Fullam et al. | 396/402 |
| 6,067,399 A * | 5/2000 | Berger | 386/280 |
| 6,350,235 B1 * | 2/2002 | Cohen et al. | 600/199 |

(Continued)

OTHER PUBLICATIONS

Akgul T, Sun M, Sclabassi RJ, Cetin AE. Characterization of sleep spindles using higher order statistics and spectra. IEEE Transactions on Biomedical Engineering. Aug. 2000;47(8):997-1009.

(Continued)

*Primary Examiner* — William Thomson
*Assistant Examiner* — Shirley Jian
(74) *Attorney, Agent, or Firm* — The Webb Law Firm

(57) ABSTRACT

Electronic systems, devices and methods are provided to accurately measure both food intake and physical activity in a subject. A device is provided to be placed on a subject which records video as well as other physiological and/or environmental data. Video data can be analyzed along with other data obtained by the device to determine food consumption and physical activity of the subject, much of which is accomplished by automated computer-implemented processes.

18 Claims, 28 Drawing Sheets

(56) References Cited

U.S. PATENT DOCUMENTS

| | | | |
|---|---|---|---|
| 6,527,711 | B1 | 3/2003 | Stivoric et al. |
| 6,553,386 | B1 | 4/2003 | Alabaster |
| 6,735,477 | B2 | 5/2004 | Levine |
| 6,922,184 | B2 | 7/2005 | Lawrence et al. |
| 6,932,766 | B2 | 8/2005 | Bergh et al. |
| 7,434,541 | B2* | 10/2008 | Kates ............................ 119/720 |
| 7,729,758 | B2* | 6/2010 | Haller et al. ...................... 607/2 |
| 7,810,750 | B2* | 10/2010 | Abreu ........................ 242/378.1 |
| 7,914,468 | B2* | 3/2011 | Shalon et al. ................. 600/590 |
| 7,983,933 | B2* | 7/2011 | Karkanias et al. ................ 705/2 |
| 8,271,092 | B2* | 9/2012 | Philipp .......................... 607/59 |
| 8,328,420 | B2* | 12/2012 | Abreu ........................... 374/208 |
| 8,540,363 | B2* | 9/2013 | Abreu ............................ 351/74 |
| 8,849,379 | B2* | 9/2014 | Abreu ........................... 600/474 |
| 9,042,596 | B2* | 5/2015 | Connor ......................... 382/100 |
| 2002/0010390 | A1* | 1/2002 | Guice et al. ................... 600/300 |
| 2002/0027164 | A1* | 3/2002 | Mault et al. .............. 235/462.46 |
| 2004/0100376 | A1* | 5/2004 | Lye et al. .................. 340/539.12 |
| 2004/0242976 | A1* | 12/2004 | Abreu ........................... 600/315 |
| 2006/0064037 | A1* | 3/2006 | Shalon et al. ................. 600/586 |
| 2007/0002039 | A1 | 1/2007 | Pendleton |
| 2007/0016098 | A1 | 1/2007 | Kim |
| 2007/0106127 | A1 | 5/2007 | Alman |
| 2007/0248238 | A1* | 10/2007 | Abreu ........................... 381/381 |
| 2008/0136916 | A1* | 6/2008 | Wolff ............................ 348/169 |
| 2008/0140444 | A1* | 6/2008 | Karkanias et al. ................ 705/2 |
| 2008/0143954 | A1* | 6/2008 | Abreu ........................... 351/158 |
| 2008/0144854 | A1* | 6/2008 | Abreu ............................ 381/74 |
| 2008/0267444 | A1* | 10/2008 | Simons-Nikolova et al. 382/100 |
| 2009/0105605 | A1* | 4/2009 | Abreu ........................... 600/549 |
| 2011/0051982 | A1* | 3/2011 | Abreu ........................... 381/384 |
| 2012/0220234 | A1* | 8/2012 | Abreu ......................... 455/41.2 |
| 2013/0336519 | A1* | 12/2013 | Connor ......................... 382/100 |
| 2014/0078462 | A1* | 3/2014 | Abreu ........................... 351/111 |
| 2014/0081578 | A1* | 3/2014 | Connor ........................... 702/19 |
| 2014/0349256 | A1* | 11/2014 | Connor ......................... 434/127 |
| 2014/0349257 | A1* | 11/2014 | Connor ......................... 434/127 |
| 2014/0350353 | A1* | 11/2014 | Connor ......................... 600/301 |

OTHER PUBLICATIONS

Baker-Fulco CJ, Kramer FM, Lesher LL, Merrill E, Johnson J, DeLany J. Dietary Intakes of Female and Male Combat Support Hospital Personnel Subsisting on Meal-Focused or Standard Versions of the Meal, Ready-to-Eat. Sep. 2002. U.S. Army Medical Research and Materiel Command Technical Report No. T-02/23.

Bandini LG, Schoeller DA, Cyr HN, Dietz WH. Validity of reported energy intake in obese and nonobese adolescents. Am J Clin Nutr. Sep. 1990;52(3):421-425.

Barsh GS, Farooqi IS, O'Rahilly S. Genetics of body-weight regulation. Nature. Apr. 6, 2000;404(6778):644-51.

Bates RR, Sun M, Scheuer ML, Sclabassi RJ. Analysis of Multi-Channel Subdural EEG by Recurrent Neural Networks In Attoh-Okine NO, Ayyub BM (eds.), Applied Research in Uncertainty Modeling and Analysis, pp. 139-160. Springer, NY, 2005.

Bates RR, Sun M, Scheuer ML, Sclabassi RJ. Detection of seizure foci by recurrent neural network. Proceedings of the 22nd Annual International Conference of the IEEE Engineering in Medicine and Biology Society, Chicago, IL; Jul. 2000;2:1377-9.

Bates RR, Sun M, Scheuer ML, Sclabassi RJ. Seizure detection by recurrent backpropagation neural network analysis. Proceedings of the 4th International Symposium on Uncertainty Modeling and Analysis, College Park, MD; Sep. 21-24, 2003:312-7.

Bathalon GP, Tucker KL, Hays NP, Vinken AG, Greenberg AS, McCrory MA, Roberts SB. Psychological measures of eating behavior and the accuracy of 3 common dietary assessment methods in healthy postmenopausal women. Am J Clin Nutr. Mar. 2000;71(3):739-45.

Bell CG, Gray J. The revolution yet to happen. Microsoft Technical Report MSR-TR-98-44, 1997. In Denning PJ, Metcalf RM (eds.), Beyond Calculation: The Next Fifty Years of Computing, pp. 5-32. Copernicus, NY, 1997.

Bell G. A personal digital store. Commun ACM. Jan. 2001;44(1):86-91.

Black AE, Bingham SA, Johansson G, Coward WA. Validation of dietary intakes of protein and energy against 24 hour urinary N and DLW energy expenditure in middle-aged women, retired men and post-obese subjects: comparisons with validation against presumed energy requirements. Eur J Clin Nutr. Jun. 1997;51(6):405-13.

Blundell JE. What foods do people habitually eat? A dilemma for nutrition, an enigma for psychology. Am J Clinical Nutrition. 2000;71(1):3-5.

Bodo Y, Laurent N., Dugelay JL. A scrambling method based on disturbance of motion vector. Proceedings of 10th ACM International Conference on Multimedia in Juan-les-Pins, France; Dec. 1-6, 2002:89-90.

Bouchard C, Tremblay A, Després JP, Nadeau A, Lupien PJ, Thériault G, Dussault J, Moorjani S, Pinault S, Fournier G. The response to long-term overfeeding in identical twins. N Engl J Med. May 24, 1990;322(21):1477-82.

Bouguet JY. Camera Calibration Toolbox for Matlab. Available at http://www.vision.caltech.edu/bouguetj/calib_doc/index.html (last accessed Jun. 16, 2008).

Boyle M, et al. The Effects of Filtered Video on Awareness and Privacy. Proceedings of CSCW 2000 Conference on Computer Supported Cooperative Work. CHI Letters, 2000;2(3):1-10. New York: ACM Press.

Bray GA, DeLany JP, Harsha DW, Volaufova J, Champagne CC. Evaluation of body fat in fatter and leaner 10-y-old African American and white children: the Baton Rouge Children's Study. Am J Clin Nutr. Apr. 2001;73(4):687-702.

Bray GA, Lovejoy JC, Smith SR, DeLany JP, Lefevre M, Hwang D, Ryan DH, York DA. The influence of different fats and fatty acids on obesity, insulin resistance and inflammation. J Nutr. Sep. 2002;132(9):2488-91.

Bray T, Paoli J, Sperberg-McQueen CM (eds.). World Wide Web Consortium (W3C) Recommendation: Extensible Markup Language (XML) 1.0. Feb. 10, 1998.

Breum L, Rasmussen MH, Hilsted J, Fernstrom JD.Twenty-four-hour plasma tryptophan concentrations and ratios are below normal in obese subjects and are not normalized by substantial weight reduction. Am J Clin Nutr. May 2003;77 (5):1112-8.

Buhl KM, Gallagher D, Hoy K, Matthews DE, Heymsfield SB. Unexplained disturbance in body weight regulation: diagnostic outcome assessed by doubly labeled water and body composition analyses in obese patients reporting low energy intakes. J Ann Diet Assoc. Dec. 1995;95(12):1393-400.

Campfield LA, Smith FJ, Guisez Y, Devos R, Burn P. Recombinant mouse OB protein: evidence for a peripheral signal linking adiposity and central neural networks. Science. Jul. 28, 1995;269(5223):546-9.

Castellani JW, Delany JP, O'Brien C, Hoyt RW, Santee WR, Young AJ. Energy expenditure in men and women during 54 h of exercise and caloric deprivation. Med Sci Sports Exerc. May 2006;38(5):894-900.

Castellani JW, Francis JR, Stulz DA, DeLany JP, Hoyt RW, Bovill ME, Young AJ. Body fluid regulation in a simulated disabled submarine: effects of cold, reduced O2, and elevated CO2. Aviat Space Environ Med. Aug. 2005;76(8):753-9.

Champagne CM, Bray GA, Kurtz AA, Monteiro JB, Tucker E, Volaufova J, Delany JP. Energy intake and energy expenditure: a controlled study comparing dietitians and non-dietitians. J Am Diet Assoc. Oct. 2002;102(10):1428-32.

Chang Y, Yan R, Chen D, Yang J. People Identification with Limited Labels in Privacy-Protected Video. Proceedings of the 2006 IEEE International Conference on Multimedia & Expo, Toronto, Ontario, Canada; Jul. 9-12, 2006:1005-8.

Charles PJ, Sun M, Sclabassi RJ. Statistical reduction of EEG data. Proceedings of the 22nd Annual International Conference of the IEEE Engineering in Medicine and Biology Society, Chicago, IL; Jul. 23-28, 2000;2:1394-5.

Chen D, Chang Y, Yan R, Yang J. Tools for protecting the Privacy of Specific Individuals in Video. EURASIP J Appl Signal Processing. 2007; Article ID 75427, 9 pp.

Chen D, Liu Q, Sun M, Yang J. Mining appearance models directly from compressed video. Proceedings of the 12th ACM SIGKDD

(56) References Cited

OTHER PUBLICATIONS

International Conference on Knowledge Discovery and Data Mining, Philadelphia, PA; Aug. 20-23, 2006.

Chen D, Malkin R, Yang J. Multimodal detection of human interaction events in a nursing home environment. Proceedings of ACM International Conference on Multimodal Interface, State College, PA; Oct. 13-15, 2004:82-9.

Chen D, Yan R, Yang J. Activity analysis in privacy-protected video. Submitted to IEEE Transactions on Multimedia, 2007, available at http://www.informedia.cs.cmu.edu/documents/T-MM_Privacy_J2c.pdf.

Chen D, Yang J, Malkin R, Wactlar HD. Detecting social interaction of elderly in a nursing home environment. ACM Transactions on Multimedia Computing, Communications, and Applications. Feb. 2007;3(1):Article 6.

Chen D, Yang J, Wactlar H. A study of detecting social interaction in a nursing home environment. IEEE International Workshop on Human-Computer Interaction in conjunction with the Tenth IEEE International Conference on Computer Vision, Beijing, China; Oct. 15-16, 2005. In Computer Vision in Human-Computer Interaction, pp. 199-210. Springer, Berlin/Heidelberg, Germany, 2005.

Chen D, Yang J, Wactlar HD. Towards automatic analysis of social interaction patterns in a nursing home environment from video. Proceedings of the 6th ACM SIGMM International Workshop on Multimedia Information Retrieval, New York, NY; Oct. 10-16, 2004:283-90.

Chen D, Yang J. Online learning region confidences for object tracking. Second Joint IEEE International Workshop on Visual Surveillance and Performance Evaluation of Tracking and Surveillance, in conjunction with the Tenth IEEE International Conference on Computer Vision, Beijing, China; Oct. 15-21, 2005:1-8.

Chen D, Yang Y. Exploiting high dimensional video features using layered gaussian mixture models. Proceedings of 18th International Conference on Pattern Recognition, Hong Kong; Aug. 20-24, 2006;2:1078-81.

Chen J, et al. Expand Training Set for Face Detection by GA Resampling. Proceedings of the 6th IEEE International Conference on Automatic Face and Gesture Recognition, Seoul, Korea; May 17-19, 2004: 73-78.

Choi S, Blake V, Cole S, Fernstrom JD. Effects of chronic fenfluramine administration on hypothalamic neuropeptide mRNA expression. Brain Res. May 4, 2006;1087(1):83-6. Epub Apr. 13, 2006.

Choi S, Jonak EM, Simpson L, Patil V, Fernstrom JD. Intermittent, chronic fenfluramine administration to rats repeatedly suppresses food intake despite substantial brain serotonin reductions. Brain Res. Feb. 22, 2002;928 (1-2):30-9.

Christel MG. Windowing time in digital libraries. Proceedings of the ACM/IEEE Joint Conference on Digital Libraries, Chapel Hill, NC; Jun. 11-15, 2006: 190-91.

Clark D, Tomas F, Withers RT, Chandler C, Brinkman M, Phillips J, Berry M, Ballard FJ, Nestel P. Energy metabolism in free-living, 'large-eating' and 'small-eating' women: studies using 2H2(18)O. Br J Nutr. Jul. 1994;72(1):21-31.

Clark J. (ed.) (1999). World Wide Web Consortium (W3C) Recommendation: ). XSL Transformations (XSLT). Nov. 16, 1999.

Coates PS, Fernstrom JD, Fernstrom MH, Schauer PR, Greenspan SL. Gastric bypass surgery for morbid obesity leads to an increase in bone turnover and a decrease in bone mass. J Clin Endocrinol Metab. Mar. 2004;89(3):1061-5.

DeLany JP, Bray GA, Harsha DW, Volaufova J. Energy expenditure and substrate oxidation predict changes in body fat in children. Am J Clin Nutr. Oct. 2006;84(4):862-70.

DeLany JP, Bray GA, Harsha DW, Volaufova J. Energy expenditure in African American and white boys and girls in a 2-y follow-up of the Baton Rouge Children's Study. Am J Clin Nutr. Feb. 2004;79(2):268-73.

DeLany JP, Bray GA, Harsha DW, Volaufova J. Energy expenditure in preadolescent African American and white boys and girls: the Baton Rouge Children's Study. Am J Clin Nutr. Apr. 2002;75(4):705-13.

DeLany JP, Schoeller DA, Hoyt RW, Askew EW, Sharp MA. Field use of D2 18O to measure energy expenditure of soldiers at different energy intakes. J Appl Physiol. Nov. 1989;67(5):1922-9.

Dittmann J, Steinmetz A. Enabling technology for the trading of MPEG-encoded video. Proceedings of the Second Australasian Conference on Information Security and Privacy. Information Security and Privacy, pp. 314-324, in Lecture Notes in Computer Science, vol. 1270. Springer, Berlin/Heidelberg, Germany, 1997.

Elad M. On the Origin of the Bilateral Filter and Ways to Improve It. IEEE Transactions on Image Processing. Oct. 2002;11(10):1141-51.

Ellenby MS, McNames J, Lai S, McDonald BA, Krieger D, Sclabassi RJ, Goldstein B. Uncoupling and recoupling of autonomic regulation of the heart beat in pediatric septic shock. Shock. Oct. 2001;16(4):274-7.

Lee M, Shen M, Yoneyama A, Jay Kuo CC. DCT-domain image registration techniques for compressed video. Proceedings of the 2005 IEEE Symposium on Circuits and Systems, Kobe, Japan; Mar. 23-26, 2005;5:4562-65.

Levas A, Brown E, Murdock JW, Ferrucci D. The Semantic Analysis Workbench (SAW): Towards a Framework for Knowledge Gathering and Synthesis. IBM Research report, RC23738 (W0503-053), Mar. 9, 2005.

Lewis RJ. Power analysis and sample size determination: concepts and software tools. 2000 Annual Meeting of the Society for Academic Emergency Medicine (SAEM), San Francisco, CA; May 22-25, 2000.

Li S, Chen G, Cheung A, Bhargava B, Lo KT. On the design of perceptual MPEG-Video encryption algorithms. IEEE Transaction on Circuits and Systems for Video Technology. Feb. 2007;17(2):241-23.

Li S, Chen G., Zheng X. Chaos-based encryption for digital images and videos. Multimedia Security Handbook, ch. 4, 1133-67 (B. Furht and D. Kirovski, eds., CRC Press, 2004).

Lichtman SW, Pisarska K, Berman ER, Pestone M, Dowling H, Offenbacher E, Weisel H, Heshka S, Matthews DE, Heymsfield SB. Discrepancy between self-reported and actual caloric intake and exercise in obese subjects. N Engl J Med. Dec. 31, 1992;327(27):1893-8.

Lienhart R, Maydt J. An extended set of haar-like features for rapid object detection. Proceedings of the 2002 International Conference on Image Processing, Rochester, NY;Sep. 22-25, 2002;1:900-03.

Lifson N. Theory of use of the turnover rates of body water for measuring energy and material balance. J Theor Biol. Sep. 1966;12(1):46-74.

Liu B, Sclabassi RJ, Liu Q, Kassam A, Li CC, Sun M. Automatic Tracking of Region of Interest in Neurosurgical Video. Proceedings of the IEEE 31st Annual Northeast Bioengineering Conference, Hoboken, NJ; Apr. 2-3, 2005:9-10.

Liu B, Sun M, Liu Q, Kassam A, Li CC, Sclabassi R. Automatic Detection of Region of Interest Based on Object Tracking in Neurosurgical Video. Proceedings of the 27th Annual Conference of the IEEE Engineering in Medicine and Biology Society, Shanghai, China; Sep. 2005;6:6273-6.

Liu Q, Chen D, Sun M, Sclabassi RJ. Specialized Video and Physiological Data Coding System for Remote Monitoring. Proceedings of the 2006 IEEE International Conference on Multimedia & Expo, Toronto, Ontario, Canada; Jul. 9-12, 2006:2001-4.

Liu Q, Sclabassi RJ, Li CC, Sun M. An Application of MAP-MRF to Change Detection in Image Sequence Based on Mean Field Theory. EURASIP J Appl Signal Processing. 2005;13:1956-68.

Liu Q, Sclabassi RJ, Sun M. Change Detection in Medical Monitoring Video Based on Markov Random Field Theory. Proceedings of 2004 International Symposium on Intelligent Signal Processing and Communication Systems, Seoul, Korea; Nov. 18-19, 2004:63-6.

Liu Q, Sun M, Sclabassi RJ. Patient Tracking for Video/EEG Monitoring Based on Change Detection in DCT Domain. Proceedings of the IEEE 31st Annual Northeast Bioengineering Conference, Hoboken, NJ; Apr. 2-3, 2005:114-5.

(56) References Cited

OTHER PUBLICATIONS

Ma WY, Manjunath BS. EdgeFlow: a technique for boundary detection and image segmentation. IEEE Trans Image Processing. Aug. 2000;9(8):1375-88.

Maffei M, Halaas J, Ravussin E, Pratley RE, Lee GH, Zhang Y, Fei H, Kim S, Lallone R, Ranganathan S, et al. Leptin levels in human and rodent: measurement of plasma leptin and ob RNA in obese and weight-reduced subjects. Nat Med. Nov. 1995;1(11):1155-61.

Malkin R, Chen D, Yang J, Waibel A. Directing attention in online aggregate sensor streams via auditory blind value assignment. Proceedings of the 2006 IEEE International Conference on Multimedia & Expo, Toronto, Ontario, Canada; Jul. 9-12, 2006:2137-40.

Malkin R, Chen D, Yang J, Waibel A. Multimodal estimation of user interruptibility for smart mobile applications. Proceeding of the 8th International Conference on Multimodal Interfaces, Banff, Canada; Nov. 2-4, 2006:118-25.

Manjunath BS, Ma WY. Texture features for browsing and retrieval of image data. IEEE Trans. on Pattern Analysis and Machine Intelligence. Aug. 1996;18(8):837-42.

Meier T, Ngan KN. Video segmentation for content-based coding. IEEE Trans on Circuits and Systems for Video Technology. Dec. 1999;9(8):1190-1203.

Moscheni F, Bhattacharjee S, Kunt M. Spatio-temporal Segmentation based on Region Merging. IEEE Transactions on Pattern Analysis and Machine Intelligence. Sep. 1998; 20(9):897-915.

Must A et al. The Disease Burden Associated with Overweight and Obesity. J Am Med Assoc. Oct. 1999:282 (16):1523-29.

Nardi BA, Schwarz H, Kuchinsky A, Lerichner R, Whittaker S, Sclabassi R. Turning Away from Talking Heads: The Use of Video-as-Data in Neurosurgery. Proceedings of the INTERACT '93 and CHI '93 Conference on Human Factors in Computing Systems, New York, NY; Apr. 24-29, 1993:327-34.

Nielsen SJ, Popkin BM. Patterns and trends in food portion sizes, 1977-1998. JAMA. Jan. 22-29, 2003;289(4):450-3.

NIH 1R01EB002309-01, "Video Compression for Remote Monitoring of Neurosurgery". (Abstract only).

NIH 2-R01-NS/MH38494-04, "Video-EEG Data Compression". (Abstract only).

NIH Grant R01EB002099, "Data Communication and Power Delivery for Implantable Micro Devices". (Abstract only).

Otsu N. A threshold selection method from gray-level histograms. IEEE Transactions on Systems, Man, and Cybernetics. Jan. 1979;9(1):62-66.

Pazarci M, Dipcin V. A MPEG2-transparent scrambling technique. IEEE Transactions on Consumer Electronics. May 2002; 48(2):345-55.

Peng R, Sclabassi RJ, Liu Q, Liu B, Xu J, Sun M. Object-Based Video Representation for Remote Patient Monitoring. First Transdisciplinary Conference on Distributed Diagnosis and Home Healthcare, Arlington, VA; Apr. 2-4, 2006:83-6.

Perlman AL, Ettema SL, Barkmeier J. Respiratory and acoustic signals associated with bolus passage during swallowing. Dysphagia. Mar. 2000;15(2):89-94.

Pingali G, Jain R. Electronic chronicles: empowering individuals, groups, and organizations. IEEE International Conference on Multimedia and Expo, Amsterdam, the Netherlands; Jul. 6-8, 2005:1540-4.

Pon KS, Sclabassi RJ, Liu Q, Scheuer M, Sun M. A Medical EEG/Video Multimedia Content Description System. Proceedings of 2004 International Symposium on Intelligent Signal Processing and Communication Systems, Seoul, Korea; Nov. 18-19, 2004:592-5.

Pon LS, Sun M, Sclabassi RJ. Adaptive separation of background activity and transient phenomenon in epileptic EEG using mathematical morphology and wavelet transforms. Proceedings of the 2nd Annual International Conference of the IEEE Engineering in Medicine and Biology Society, Chicago, IL; Jul. 2000;2:1583-5.

Pon LS, Sun M, Sclabassi RJ. The bi-directional spike detection in EEG using mathematical morphology and wavelet transform. Sixth International Conference on Signal Processing, Beijing, China; Aug. 26-30, 2002;2:1512-5.

Pon LS, Sun M, Sclabassi RJ. Analysis of heart rate changes associated with ictal activity. Proceedings of the 22nd Annual International Conference of the IEEE Engineering in Medicine and Biology Society, Chicago, IL; Jul. 2000;1:68-70.

Pon LS, Sun M, Sclabassi RJ. Interictal spike analysis using stochastic point process. Proceedings of the Fourth International Symposium on Uncertainty Modeling and Analysis, College Park, MD; Sep. 24, 2003:262-7.

Pon LS. Separation of Spiky Transients in EEG/MEG Using Morphological Filters in Multi-Resolution Analysis. Ph.D. Thesis, Department of Electrical Engineering, University of Pittsburgh, Feb. 2002.

Prentice AM, Black AE, Coward WA, Davies HL, Goldberg GR, Murgatroyd PR, Ashford J, Sawyer M, Whitehead RG. High levels of energy expenditure in obese women. Br Med J (Clin Res Ed). Apr. 12, 1986;292(6526):983-7.

Press WH, Teukolsky SA, Vetterling WT, Flannery BP. Numerical Recipes in C: The Art of Scientific Computing (2d ed.). Cambridge University Press, New York, NY, 1992.

Racette SB, Schoeller DA, Luke AH, Shay K, Hnilicka J, Kushner RF. Relative dilution spaces of 2H- and 18O-labeled water in humans. Am J Physiol. Oct. 1994;267(4 Pt 1):E585-90.

Rhee MY. Internet Security: Cryptographic Principles, Algorithms and Protocols. Wiley, Hoboken, NJ, 2003, pp. 57-75 and 162-172.

Rogers J, Puleston C, Rector A. The CLEF Chronicle: Patient histories derived from electronic health records. Proceedings of the 22nd International Conference on Data Engineering Workshops, Atlanta, GA; Apr. 3-7, 2006:x109.

Rudney JD, Ji Z, Larson CJ. The prediction of saliva swallowing frequency in humans from estimates of salivary flow rate and the volume of saliva swallowed. Archs Oral Biol. Jun. 1995;40(6):507-12.

Sarkar S, Phillips PJ, Liu Z, Vega IR, Grother P, Bowyer KW. The HumanID Gait Challenge Problem: Data Sets, Performance, and Analysis. IEEE Transactions on Pattern Analysis and Machine Intelligence. Feb. 2005;27(2):162-77.

Schatzkin A, Kipnis V, Carroll RJ, Midthune D, Subar AF, Bingham S, Schoeller DA, Troiano RP, Freedman LS. A comparison of a food frequency questionnaire with a 24-hour recall for use in an epidemiological cohort study: results from the biomarker-based Observing Protein and Energy Nutrition (OPEN) study. Int J Epidemiol. Dec. 2003;32 (6):1054-62.

Scher MS, Steppe DA, Dokianakis SG, Sun M, Guthrie RD, Sclabassi RJ. Cardiorespiratory behavior during sleep in full-term and preterm neonates at comparable postconceptional term ages. Pediatr Res. Dec. 1994;36(6):738-44.

Scher MS, Sun M, Hatzilabrou GM, Greenberg NL, Cebulka G, Krieger D, Guthrie RD, Sclabassi RJ. Computer analyses of EEG-sleep in the neonate: methodological considerations. J Clin Neurophysiol. Jul. 1990;7(3):417-41.

Scher MS, Sun M, Steppe DA, Guthrie RD, Sclabassi RJ. Comparisons of EEG spectral and correlation measures between healthy term and preterm infants. Pediatr Neurol. Mar. 1994;10(2):104-8.

Schoeller DA et al. How much physical activity is needed to minimize weight gain in previously obese women? Am J Clin Nutrition. 1997;66:551-56.

U.S. Department of Agriculture and Agricultural Research Service, "USDA nutrient database for standard reference, Release 19," available in Nutrient Database Laboratory Home Page, 2006, (www.ars.usda.gov/ba/bhnrc/ndl).

U.S. Department of Agriculture, Agricultural Research Service. 2007. USDA National Nutrient Database for Standard Reference, Release 20. Nutrient Data Laboratory Home Page, (www.ars.usda.gov/ba/bhnrc/ndl)).

U.S. Department of Labor (Bureau of Labor Statistics), American time use survey—2005, USDL 06-1276. Washington, D.C., Jul. 27, 2006.

Vanderschoot J, Schreur HJW. Biaxial esophagus microphone recording of lung sound. Proceedings of the Annual International Conference of the IEEE Engineering in Medicine and Biology Society. Oct. 31-Nov. 3, 1991;13(4):1631-2.

(56) References Cited

OTHER PUBLICATIONS

Velthuis-te Wierik EJ, Westerterp KR, van den Berg H. Impact of a moderately energy-restricted diet on energy metabolism and body composition in non-obese men. Int J Obes Relat Metab Disord. May 1995;19(5)318-24.

Vincent L, Soille P. Watersheds in Digital Spaces: An Efficient Algorithm Based on Immersion Simulation. IEEE Transactions on Pattern Analysis and Machine Intelligence. Jun. 1991;13(6):583-89.

Vincent L. Morphological Grayscale Reconstruction in Image Analysis: Applications and Efficient Algorithms. IEEE Transactions on Image Processing. Apr. 1993;2(2):176-201.

Viola P, Jones MJ. Robust Real-Time Face Detection. Int J Computer Vision. 2004;57(2):137-54.

Viola P, Jones W. Rapid Object Detection using a Boosted Cascade of Simple Features. Proceedings of the 2001 IEEE Computer Society Conference on Computer Vision and Pattern Recognition, Kauai, Hawaii; Dec. 9-14, 2001;1:511-7.

Vitabile S, Pollaccia G, Pilato G, Sorbello F. Road signs recognition using a dynamic pixel aggregation technique in the HSV color space. Proceedings of the 11th International Conference on Image Analysis and Processing, Palermo, Italy; Sep. 26-28, 2001:572-7.

Wang JYA, E.H. Adelson. Representing Moving Images with Layers. IEEE Transactions on Image Processing. Sep. 1994;3(5):625-38.

Wang C, Yu HB, Zheng M. A DCT-based MPEG-2 transparent scrambling algorithm. IEEE Transactions on Consumer Electronics. Nov. 2003;49(4):1208-13.

Wang H, Wang LY. Continuous intro-operative respiratory auscultation in anesthesia. Proceedings of IEEE Sensors. Oct. 2003;2:1002-05.

Wang J, Chun J. Image registration for an imaging system on-board fast moving military vehicle. Proceedings of the IEEE 2000 National Aerospace and Electronics Conference, Dayton, Ohio; Oct. 10-12, 2000;239-43.

Wang W, Chen D, Gao W, Yang J. Modeling background from compressed video. Second Joint IEEE International Workshop on Visual Surveillance and Performance Evaluation of Tracking and Surveillance, in conjunction with the Tenth IEEE International Conference on Computer Vision, Beijing, China; Oct. 15-16, 2005:161-8.

Wareham NJ, Rennie KL. The assessment of physical activity in individuals and populations: why try to be more precise about how physical activity is assessed? Int J Obes Relat Metab Disord. Aug. 1998;22 Suppl 2:S30-8.

Webster JG. Medical Instrumentation: Application and Design (3d ed.). Wiley, Hoboken NJ, 1993.

Wessel BL, Roche P, Sun M, Sclabassi RJ. Optimization of an implantable volume conduction antenna. 26th Annual Conference of the IEEE Engineering in Medicine and Biology Society, San Francisco, CA; Sep. 1-4, 2004;2:4111-4.

World Wide Web Consortium W3C. Synchronized Multimedia Integration Language (SMIL) 1.0 Specification, Jun. 15, 1998. Available at: http://www.w3.org/TR/REC-smil/.

Xu J, Ilgin H, Liu Q, Kassam A, Sclabassi RJ, Chaparro LF, Sun M. Content-based video coding for remote monitoring of neurosurgery. Proceedings of the 26th Annual International Conference of the Engineering in Medicine and Biology Society, San Francisco, CA; Sep. 1-5, 2004;2:3136-9.

Xu J, Ilgin H, Liu Q, Sun M, Sclabassi RJ, Chaparro LF. Multi-channel video for patient monitoring based on DCT compositing. Proceedings of the IEEE 30th Annual Northeast Bioengineering Conference, Springfield, MA; Apr. 17-18, 2004:63-4.

Xu J, Sclabassi RJ, Liu B, Sun M. Content-Based Video Preprocessing for Remote Monitoring of Neurosurgery. First Transdisciplinary Conference on Distributed Diagnosis and Home Healthcare, Arlington, VA; Apr. 2-4, 2006:67-70.

Xu J, Sclabassi RJ, Liu Q, Hu C, Chaparro LF, Sun M. A region-based video coding method for remote monitoring of neurosurgery. Proceedings of the IEEE 31st Annual Northeast Bioengineering Conference, Hoboken, NJ; Apr. 2-3, 2005:89-91.

Yan R, Yang J, Hauptmann A. Automatically labeling video data using multi-class active learning. Proceedings of 9th International Conference on Computer Vision, Nice, France; Oct. 13-16, 2003:516-23.

Yan R, Zhang J, Yang J, Hauptmann A. A discriminative learning framework with pairwise constraints for video object classification. Proceedings of the 2004 IEEE Computer Society Conference on Computer Vision and Pattern Recognition, Washington, DC; Jul. 27-Jul. 2, 2004;2:284-91.

Yan R, Zhang J, Yang J, Hauptmann A. A discriminative learning framework with pairwise constraints for video object classification. IEEE Transaction on Pattern Analysis and Machine Intelligence. Apr. 2006;28(4):578-93.

Yang J, Chen X, Kunz W, Kundra H. Face as an index: knowing who is who using a PDA. Int J Imaging Syst Technol. 2003,13(1):33-41.

Yang J, Chen X, Kunz W. A PDA-based face recognition system. Proceedings of the 6th IEEE Workshop on Applications of Computer Vision, Orlando, FL; Dec. 3-4, 2002:19-23.

Yang J, Gao J, Zhang Y, Chen X, Waibel A. An automatic sign recognition and translation system. Proceedings of the 2001 Workshop on Perceptive User Interfaces, Orlando, Florida; Nov. 15-16, 2001:1-8.

Yang J, Holtz W, Yang W, Vo MT. An adaptive multimodal interface for wireless applications. Proceedings of 2nd International Symposium on Wearable Computers, Oct. 19-20, 1998:172-73.

Yang J, Yang W, Denecke M, Waibel A. Smart sight: a tourist assistant system. Proceedings of 3rd International Symposium on Wearable Computers, San Francisco, CA; Oct. 18-19, 1999:73-78.

Yang L, Zheng N, Cheng H, Fernstrom JD, Sun M, Yang J. Automatic Dietary Assessment from Fast Food Categorization (abstract). Proceedings of the 2008 IEEE 34th Annual Northeast Bioengineering Conference, Providence, RI; Apr. 4-6, 2008.

Yao N et al. A Laser Based Depth Measurement Method for Digital Imaging of Close-up Objects (abstract) Proceedings of the 16th International Conference on Mechanics in Medicine and Biology, Pittsburgh, PA; Jul. 23-25, 2008.

Yao N et al. A Video Processing Approach to the Study of Obesity (abstract). Proceedings of the 2007 IEEE International Conference on Multimedia & Expo, Beijing, China; Jul. 2-5, 2007:1727-1730.

Yao N et al. A Video-based Algorithm for Food Intake Estimation in the Study of Obesity. Proceedings of the 2007 IEEE 33rd Annual Northeast Bioengineering Conference, Stony Brook, New York; Mar. 10-11, 2007: 298-99.

Yadollahi A, Moussavi AMK. A robust method for estimating respiratory flow using tracheal sounds entropy. IEEE Transactions on Biomedical Engineering. Apr. 2006;53(4):662-68.

Zhang J, Chen X, Yang J, Waibel A. A PDA-based sign translator. Proceedings of 4th IEEE International Conference on Multimodal Interfaces, Pittsburgh, PA; Oct. 14-16, 2002:217-22.

Zhang K et al. Measurement of daily physical activity. Obesity Res. Jan. 2003; 11(1):33-40.

Zheng H, Wang H, Wang LY, Yin G. Lung sound pattern analysis for anesthesia monitoring. Proceedings of the 2005 American Control Conference, Portland, OR; Jun. 8-10, 2005;3:1563-8.

www.minisun.com, IDEEA, overview.

Schoeller DA, Bandini LG, Dietz WH. Inaccuracies in self-reported intake identified by comparison with the doubly labelled water method. Can J Physiol Pharmacol. Jul. 1990;68(7):941-9.

Schoeller DA. How accurate is self-reported dietary energy intake? Nutr Rev. Oct. 1990;48(10):373-9.

Schoeller DA. Measurement of energy expenditure in free-living humans by using doubly labeled water. J Nutr. Nov. 1988;118(11):1278-89.

Schoeller DA. Recent advances from application of doubly labeled water to measurement of human energy expenditure. J Nutr. Oct. 1999;129(10):1765-8.

Schutz Y, Weinsier RL, Hunter GR. Assessment of free-living physical activity in humans: an overview of currently available and proposed new measures. Obesity Res. Jun. 2001;9(6):368-79.

Sclabassi RJ, Harper RM. Laboratory computers in neurophysiology. Proceedings of the IEEE. Nov. 1973; 61 (11):1602-14.

Sclabassi RJ, Leichner R, Kuchinsky A, Krieger DN, Prince F. The Multimedia Medical Monitoring Diagnosis and Consultation

(56) References Cited

OTHER PUBLICATIONS

Project. Proceedings of the 24th Annual Hawaii Conference on System Sciences, Jan. 8-11, 1991;3:717-28.
Sclabassi RJ, Sonmez M, Sun M. EEG source localization: a neural network approach. Neurol Res. Jul. 2001;23(5):457-64.
Sclabassi RJ, Sun M, Sekhar L, Wasserman JF, Blue HB. An acoustic aneurysm-detector. Med Instrum. Dec. 1987;21(6):317-22.
Seale JL, Rumpler WV. Comparison of energy expenditure measurements by diet records, energy intake balance, doubly labeled water and room calorimetry. Eur J Clin Nutr. Dec. 1997;51(12):856-63.
Sekhar LN, Sclabassi RJ, Sun M, Blue HB, Wasserman JF. Intraaneurysmal pressure measurements in experimental saccular aneurysms in dogs. Stroke. Mar. 1998;19(3):352-6.
Sekihara K, Nagarajan S, Poeppel D, Miyashita Y. Estimating neural sources from each time-frequency component of magnetoencephalographic data. Proceedings of the IEEE-SP International Symposium on Time-Frequency and Time-Scale Analysis, Pittsburgh, PA; Oct. 6-9, 1998:69-72.
Sekihara K, Nagarajan SS, Poeppel D, Marantz A, Miyashita Y. Application of an MEG eigenspace beamformer to reconstructing spatio-temporal activities of neural sources. Hum Brain Mapp. Apr. 2002;15(4):199-215.
Sekihara K, Nagarajan SS, Poeppel D, Miyashita Y. Reconstructing spatio-temporal activities of neural sources using an MEG vector beamformer technique. IEEE Transactions on Biomedical Engineering. Jul. 2001;48(7):760-71.
Sekihara K, Nagarajan SS, Poeppel D, Miyashita Y. Time-frequency MEG-MUSIC algorithm. IEEE Transactions on Medical Imaging. Jan. 1999;18(1):92-7.
Sekihara K, Nagarajan SS, Poeppel D, Miyauchi S, Fujimaki N, Koizumi H, Miyashita Y. Estimating neural sources from each time-frequency component of magnetoencephalographic data. IEEE Trans Biomed Eng. May 2000;47 (5):642-53.
Sekihara K, Poeppel D, Marantz A, Koizumi H, Miyashita Y. Noise covariance incorporated MEG-MUSIC algorithm: a method for multi-dipole estimation tolerant of the influence of background brain activity. IEEE Transactions on Biomedical Engineering. Sep. 1997;44(9):839-47.
Sierra G, Telfort V, Popov B, Pelletier M, Despault P, Agarwal R, Lanzo V. Comparison of respiratory rate estimation based on tracheal sounds versus a capnograph. Proceedings of the 27th Annual International Conferences on Engineering in Medicine and Biology Society, Shanghai, China; Sep. 1-4, 2005;6:6145-8.
Simon R, Krieger D, Znati T, Lofink R, Sclabassi RJ. Multimedia MedNet: A Medical Collaboration and Consultation System. Computer. May 1995;28(5):65-73.
Song AY, Rubin JP, Thomas V, Dudas JR, Marra KG, Fernstrom MH. Body image and quality of life in post massive weight loss body contouring patients. Obesity (Silver Spring). Sep. 2006;14(9):1626-36.
Sonmez M, Sun M, Li CC, Sclabassi RJ. A hierarchical decision module based on multiple neural networks. International Conference on Neural Networks, Houston, TX; Jun. 1997,1:238-41.
Sonmez M, Sun M, Yan X, Sclabassi RJ. Extension of a training set for artificial neural networks and its application to brain source localization. IEEE International Conference on Neural Networks, Washington, DC; Jun. 3-6, 1996;2:635-40.
Sovijarvi ARA, Helisto P, Malmberg LP, Kallio K, Paajanen E, Saarinen A, Lipponen P, Haltsonen S, Pekanen L, Piirila P, Naeveri L, Katila T. A new versatile PC-based lung sound analyzer with automatic crackle analysis (HeLSA); repeatability of spectral parameters and sound amplitude in healthy subjects. Technology and Health Care. 1998;6 (1):11-22.
Spong MW, Bullo F. Controlled Symmetries and Passive Walking. IEEE Transactions on Automatic Control. Jul. 2005;50(7):1025-31.
Stein CJ, Colditz GA. The Epidemic of Obesity. J Clin Endocrinol Metab. 2004;89(6):2522-25.
Sun M, Hackworth SA, Tang Z, Zhao J, Li DL, Enos SE, Errigo B, Gilbert G, Marchessault R, Cardin S, Turner T, Sclabassi RJ. Platform Technologies for Minimally Invasive Physiological Monitoring. Proceedings of the 25th Army Science Conference, Orlando, FL; Nov. 1, 2006.
Sun M, Justin GA, Roche PA, Zhao J, Wessel BL, Zhang Y, Sclabassi RJ. Passing data and supplying power to neural implants. IEEE Eng Med Biol Mag. Sep.-Oct. 2006;25(5):39-46.
Sun M, Liu Q, Scheurer ML, Sclabassi RJ. Assessment of Object-Based Video Compression for Epilepsy Monitoring. Proceedings of the Second Joint Engineering in Medicine and Biology 4th Annual Conference and the Annual Fall Meeting of the Biomedical Engineering Society, Houston, TX; Feb. 9-10, 2006;2:1045-6.
Sun M, Liu Q, Xu J, Liu B, Hu C, Kassam A, Sclabassi RJ. A multimedia system for remote neurosurgical monitoring Proceedings of 2004 International Symposium on Intelligent Signal Processing and Communication Systems, Seoul, Korea; Nov. 18-19, 2004:379-83.
Sun M, Scheuer ML, Qian S, Pon LS, Sclabassi RJ. Time-frequency distributions of subdural EEG at epileptic seizure onset. Proceedings of the IEEE-SP International Symposium on Time-Frequency and Time-Scale Analysis, Pittsburgh, PA; Oct. 1998:73-6.
Sun M, Scheuer ML, Sclabassi RJ. Extraction and analysis of early ictal activity in subdural electroencephalogram. Ann Biomed Eng. Oct. 2001;29(10):878-86.
Sun M, Sclabassi RJ. Decomposition of biomedical signals for enhancement of their time-frequency distributions. J Franklin Institute. Jul. 2000;337(4):453-67.
Sun M, Sclabassi RJ. Precise determination of starting time of epileptic seizures using subdural EEG and wavelet transform. Proceedings of the IEEE-SP International Symposium on Time-Frequency and Time-Scale Analysis, Pittsburgh, PA; Oct. 1998:257-60.
Sun M, Sclabassi RJ. Wavelet Feature Extraction from Neurophysiological Signals. In Akay M (ed). Time Frequency and Wavelets in Biomedical Signal Processing, chapter 11, pp. 305-321. Wiley-IEEE Press, New York, NY, 1997.
Sun M, Sekhar LN, Sclabassi RJ, Wasserman JF, Blue HB, Luyckx KA. Recording and processing aneurysmal vibration signals in dogs. J Biomed Eng. Jul. 1988;10(4):336-42.
Sun M, Shi Y, Liu Q, Sclabassi RJ. Sample Domain Integration of Medical Data for Multimedia Diagnosis. IEEE Workshop on Multimedia Signal Processing, St. Thomas, Virgin Island; Dec. 9-11, 2002:363-6.
Sun M, Wessel BL, Liang W, Roche PA, Liu Q, Mickle M, Sclabassi RJ. A Volume Conduction Antenna for Implantable Devices. Proceedings of the 25th Annual International Conferences of the IEEE Engineering in Medicine and Biology Society, Cancun, Mexico; Sep. 17-21, 2003;4:3356-9.
Sun M, Yan X, Sclabassi RJ. Soft computation of numerical solutions to differential equations in EEG analysis. In Tan YP, Yap KH, Wang L (eds.). Intelligent Multimedia Processing with Soft Computing, pp. 431-451. Springer-Verlag, Heidelberg, Germany, 2005.
Sun M, Yan X, Sclabassi RJ. Solving partial differential equations in real-time using artifical neural network signal processing as an alternative to finite element analysis. Proceedings of the 2003 International Conference on Neural Networks and Signal Processing, Nanjing, China; Dec. 14-17, 2003;1:381-4.
Sural S, Qian G, Pramanik S. Segmentation and Histogram Generation using the HSV Color Space for Image Retrieval. Proceedings of the 2002 International Conference on Image Processing, Rochester, NY; Sep. 22-25, 2002;2:11-589-92.
Tharion WJ, Baker-Fulco CJ, Bovill ME, Montain SM, DeLany JP, Champagne CM, Hoyt RW, Lieberman HR. Adequacy of Garrison feeding for Special Forces soldiers during training. Mil Med. Jun. 2004;169(6):483-90.
Tharion WJ, Hoyt RW, Cline AD, DeLany JP, Lieberman HR. Energy expenditure and water turnover assessed by doubly labeled water during manual work in a dry and warm environment. J Hum-Environ Sys. 2004;7(1):11-7.
Tharion WJ, Lieberman HR, Montain SJ, Young AJ, Baker-Fulco CJ, Delany JP, Hoyt RW. Energy requirements of military personnel. Appetite. Feb. 2005;44(1):47-65. Epub Nov. 14, 2004.
Tharion WJ, Yokota M, Buller MJ, DeLany JP, Hoyt RW. Total energy expenditure estimated using a foot-contact pedometer. Med Sci Monit. Sep. 2004;10(9):CR504-9. Epub Aug. 20, 2004.

(56) References Cited

OTHER PUBLICATIONS

Thompson FE, Byers T. Dietary assessment resource manual. J Nutr. Nov. 1994;124(11 Suppl):2245S-2317S.
Tomasi C, Manduchi R. Bilateral Filtering for Gray and Color Images. Proceedings of the 6th International Conferences on Computer Vision, Bombay, India; Jan. 4-7, 1998;839-46.
Trabulsi J, Schoeller DA. Evaluation of dietary assessment instruments against doubly labeled water, a biomarker of habitual energy intake. Am J Physiol Endocrinol Metab. Nov. 2001;281(5):E891-9.
Tuschl RJ, Platte P, Laessle RG, Stichler W, Pirke KM. Energy expenditure and everyday eating behavior in healthy young women. Am J Clin Nutr. Jul. 1990;52(1):81-6.
Eng J. Sample size estimation: how many individuals should be studied? Radiology. May 2003;227(2):309-13.
Ershow AG, Ortega A, Baldwin JT, Hill JO. Engineering Approaches to Energy Balance and Obesity: Opportunities for Novel Collaborations and Research. J Diabetes Sci Tech. Jan. 2007;1(1):95-105.
Farooqi IS, Jebb SA, Langmack G, Lawrence E, Cheetham CH, Prentice AM, Hughes IA, McCamish MA, O'Rahilly S. Effects of recombinant leptin therapy in a child with congenital leptin deficiency. N Engl J Med. Sep. 16, 1999;341 (12):879-84.
Fernstrom JD, Courcoulas AP, Houck PR, Fernstrom MH. Long-term changes in blood pressure in extremely obese patients who have undergone bariatric surgery. Arch Surg. Mar. 2006;141(3):276-83.
Ferrucci D, Lally A. Building an example application with the Unstructured Information Management Architecture. IBM Systems Journal. Jul. 2004;43(3):455-75.
Ferrucci D, Lally A. UIMA: an architectural approach to unstructured information processing in the corporate research environment. J Natural Language Engineering. Sep. 2004;10(3-4):327-48.
Firmin H, Reilly S, Fourcin A. Non-invasive monitoring of reflexive swallowing. Speech Hearing and Language: work in progress. 1997;10:171-84.
Flegal KM et al. Prevalence and trends in obesity among US adults, 1999-2000. J Am Med Assoc. Oct. 2002;288 (14):1723-27.
Foutrakis GN, Yonas H, Sclabassi RJ. Saccular aneurysm formation in curved and bifurcating arteries. AJNR Am J Neuroradiol. Aug. 1999;20(7):1309-17.
Freedman DS et al. Trends and Correlates of Class 3 Obesity in the United States from 1990 through 2000. J Am Med Assoc. Oct. 2002;288(14):1758-61.
Friedl KE. Bioenergetics of Animal Locomotion: Lessons for Expedient Monitoring in Human Fitness and Weight Management. Diabetes Technol Ther. Feb. 2004;6(1):83-86.
Friedman JM, Halaas JL. Leptin and the regulation of body weight in mammals. Nature. Oct. 22, 1998;395(6704):763-70.
Friedman JM. Obesity in the new millennium. Nature. Apr. 6, 2000;404(6778):632-4.
Frykman PN, Harman EA, Opstad PK, Hoyt RW, DeLany JP, Friedl KE. Effects of a 3-month endurance event on physical performance and body composition: the G2 trans-Greenland expedition. Wilderness Environ Med. 2003 Winter;14(4):240-8.
Gao J et al. Articulated Motion Modeling for Activity Analysis. Proceedings of the 3rd International Conference on Image Video Retrieval, Dublin City, Ireland; Jul. 21-23, 2004.
Gao J et al. Combining Motion Segmentation with Tracking for Activity Analysis. Proceedings of the 6th IEEE International Conference on Automatic Face and Gesture Recognition, Seoul, Korea; May 17-19, 2004:699-704.
Gao J et al. Dining Activity Analysis Using a Hidden Markov Model. Proceedings of the 17th International Conference on Pattern Recognition, Cambridge, United Kingdom; Aug. 23-26, 2004.
Gemmell J, Bell G, Lueder R, Drucker S, Wong C. MyLifeBits: Fulfilling the Memex Vision. Proceedings of 10th ACM International Conference on Multimedia in Juan-les-Pins, France; Dec. 1-6, 2002:235-8.
Gephart K, Sun M, Sclabassi RJ. Nonlinear dynamics of heart rate in epilepsy. Proceedings of the 22nd Annual International Conference of the IEEE Engineering in Medicine and Biology Society, Chicago, IL; Jul. 23-28, 2000;4:2903-5.

Gonzalez RC, Woods RE. Digital Image Processing. Addison-Wesley Publishing Company, Lebanon, Indiana, 1993.
Goran MI, Poehlman ET. Total energy expenditure and energy requirements in healthy elderly persons. Metabolism. Jul. 1992;41(7):744-53.
Goris AH, Westerterp KR. Postabsorptive respiratory quotient and food quotient-an analysis in lean and obese men and women. Eur J Clin Nutr. Jul. 2000;54(7):546-50.
Goris AHC et al. Undereating and underrecording of habitual food intake in obese men: selective underreporting of fat intake. Am J Clin Nutr. 2000;71:130-34.
Greiner S, Yang J. Privacy Protection in an Electronic Chronicle System (abstract). Proceedings of the 2008 IEEE 34th Annual Northeast Bioengineering Conference, Providence, RI; Apr. 4-6, 2008.
Guven S, Podlaseck M, Pingali G. PICASSO: Pervasive Information Chronicling, Access, Search, and Sharing for Organizations. Proceedings of the Third IEEE International Conference on Pervasive Computing and Communications (PerCom 2005), Kauai, Hawaii; Mar. 8-12, 2005: 341-350.
Harper R, Sclabassi RJ, Estrin T. Time series analysis and sleep research. IEEE Transactions on Automatic Control. Dec. 1974;19(6): 932-43.
Hassoun MH. Fundamentals of Artificial Neural Networks. MIT Press, Cambridge, MA, 1995.
Hauptmann AG, Gao J, Yan R, Qi Y, Yang J, Wactlar HD. Automated Analysis of Nursing Home Observations. IEEE Pervasive Computing. Apr.-Jun. 2004;3(2):15-21.
Heilbronn LK, de Jonge L, Frisard MI, DeLany JP, Larson-Meyer DE, Rood J, Nguyen T, Martin CK, Volaufova J, Most MM, Greenway FL, Smith SR, Deutsch WA, Williamson DA, Ravussin E; Pennington CALERIE Team. Effect of 6-month calorie restriction on biomarkers of longevity, metabolic adaptation, and oxidative stress in overweight individuals: a randomized controlled trial. JAMA. Apr. 5, 2006;295(13):1539-48.
Herodotou N, Plataniotis KN, Venetsanopoulos AN. A color segmentation scheme for object-based video coding. Proceedings of the 1998 IEEE Symposium on Advances in Digital Filtering and Signal Processing, Jun. 5-6, 1998:25-30.
Hiiemae KM, Crompton AW. Mastication, food transport and swallowing. In Hildebrand M, Bramble DM, Liem KF, Wake DB (eds.), Functional Vertebrate Morphology, pp. 262-290. Belknap Press, Cambridge, MA, 1985.
Hintz JL. PASS 2000 User's Guide. Kaysville, UT, 2000, pp. 1-7 (Cover and Table of Contents) and 7-1 to 7-9.
Hitachi Metals America, Ltd. Press Release: Development of the World's Smallest Accelerometer Sensor. Aug. 23, 2006.
Hoyt RW, Buller MJ, Santee WR, Yokota M, Weyand PG, Delany JP. Total energy expenditure estimated using foot-ground contact pedometry. Diabetes Technol Ther. Feb. 2004;6(1):71-81.
Hu C, Sclabassi RJ, Scheuer ML, Xu J, Liu Q, Sun M. Comparing Interlaced and Progressive Scans for MPEG Coding of Medical Video. Proceedings of the 31st Annual Northeast Bioengineering Conference, Hoboken, NJ, Apr. 2-3, 2005:116-7.
Hui X, Hua DH, Liu W, Zheng XY. A brief introduction of national standard of the People's Republic of China 'Mass Center of Chinese Adults.' Proceedings of the 20th Annual International Conference of the IEEE Engineering in Medicine and Biology Society, Oct. 29-Nov. 1, 1998; 6(29):3374-8.
Hunter J. MPEG-7 Behind the Scenes. D-Lib Magazine. Sep. 1999;5(9).
Irwin ML, Ainsworth BE, Conway JM. Estimation of energy expenditure from physical activity measures: determinants of accuracy. Obesity Res. Sep. 2001;9(9):517-25.
Jain R. Media vision: Multimedia electronic chronicles. IEEE Multimedia. Jul.-Sep. 2003;10(3):111-12.
Janz KF. Physical activity in epidemiology: moving from questionnaire to objective measurement. Brit J Sports Med. 2006;40:191-92.
Justin GA, Zhang, Sclabassi RJ, Sun M. Biofuel Cells as a Possible Power Source for Implantable Electronic Devices. Proceedings of the 30th Annual Northeast Bioengineering Conference, Springfield, MA; Apr. 17-18, 2004:45-6.

(56) References Cited

OTHER PUBLICATIONS

Kachigan SK. Statistical Analysis: An Interdisciplinary Introduction to Univariate & Multivariate Methods. Radius Press, New York, NY, 1986.

Kaczkowski CH, Jones PJ, Feng J, Bayley HS. Four-day multimedia diet records underestimate energy needs in middle-aged and elderly women as determined by doubly-labeled water. J Nutr. Apr. 2000;130(4):802-5.

Kass M, Witkin A, Terzopoulos D. Snakes: active contour models. Int J Computer Vision. Jan. 1988;1(4):321-31.

Kempen KP, Saris WH, Westerterp KR. Energy balance during an 8-wk energy-restricted diet with and without exercise in obese women. Am J Clin Nutr. Oct. 1995;62(4):722-9.

Kiyokawa H, Greenberg M, Shirota K, Pasterkamp H. Auditory detection of simulated crackles in breath sounds. Chest. Jun. 2001;119(6):1886-92.

Klahn MS, Perlman AL. Temporal and durational patterns associating respiration and swallowing. Dysphagia. 1999 Summer;14(3):131-38.

Kohl III HW, Lee IM, Vuori IM, Wheeler FC, Bauman A, Sallis JF. Physical Activity and Public Health: The Emergence of a Subdiscipline—Report from the International Congress on Physical Activity and Public Health Apr. 17-21, 2006, Atlanta, Georgia, USA. J Physical Activity Health. Oct. 2006;3(4):344-64.

Kopelman PG. Obesity as a medical problem. Nature. Apr. 6, 2000;404(6778):635-43.

\* cited by examiner

METHOD, APPARATUS AND SYSTEM FOR FOOD INTAKE AND PHYSICAL ACTIVITY ASSESSMENT

CROSS REFERENCE TO RELATED APPLICATIONS

This application claims the benefit under 35 U.S.C. §119 (e) to U.S. Provisional Patent Application No. 60/936,083, filed Jun. 18, 2007 and U.S. Provisional Patent Application No. 60/949,033, filed Jul. 11, 2007, both of which are incorporated herein by reference in their entirety.

STATEMENT REGARDING FEDERAL FUNDING

The U.S. Government has a paid-up license in this invention and the right in limited circumstances to require the patent owner to license others on reasonable terms as provided for by the terms of Grant No. U01-HL91736 awarded by the National Institutes of Health.

In the United States, approximately 65% of adults and 16% children are overweight (body mass index (BMI) at least 25 $kg/m^2$) or obese (BMI≥30 $kg/m^2$). Obesity has been linked to many types of cancer (e.g., breast, colon, and prostate cancers), type 2 diabetes, coronary and congestive heart diseases, stroke, digestive diseases, respiratory diseases, osteoarthritis, and birth defects. Obesity related deaths are estimated to be 300,000 each year in the U.S., and the direct and indirect costs to the American society are estimated to be $117 billion annually.

Obesity is a complex disorder caused by a heterogeneous group of genetic and environmental factors. Research in genetics has already linked obesity to a number of components in the homeostatic system. Several genes have been identified in association with metabolic disorders and obesity, including the adrenergic-receptor gene and a group of receptor genes involved in appetite regulation. It has also been found that overweight and obesity run in families and, based on findings from a twin study, environmental factors have a lesser degree of influence within twins than between unrelated individuals. It has been suggested that obesity genes encode the molecular components of the physiological system that regulates body weight. In this regulatory system, leptin has been identified as a critical molecular component. Animal experiments have shown a significant increase in body weight when the level of leptin is reduced.

Environmental factors, such as energy intake, energy expenditure, culture, and lifestyle clearly play critical roles in obesity. A model of gene-environmental interaction has been suggested in which there is a monotonic increase in BMI with the genetic susceptibility. Without gene-environmental interaction, the slope of increase is same for the high risk and low-risk environments. However, with gene-environmental interaction, the slope of increase is much higher in the high risk environment. This model offers a plausible explanation for the relatively rapid rise in clinically diagnosed obesity that has been occurring in the United States compared to most other countries.

While the genetic study of obesity can be performed in laboratory settings based on field-acquired blood or tissue samples, environmental studies, including energy balance, lifestyle, and cultural aspects, must use "free-living" data acquired from numerous individuals. The acquisition of such data poses a daunting task due to the insufficient methodologies suitable for assessment of the general population.

Current dietary assessment is largely dependent on self-reported data by respondents. Standard 24-hour recall studies itemize all food and nutrients consumed during the past day, and food frequency questionnaires detail the usual frequencies of a long list of foods over a specific period of time. Other forms of dietary recall questionnaires have also been designed to meet particular research needs. Although these methods have been widely adopted in various research and public health settings, nutritional scientists have questioned whether the self-reported data truly reflects the amounts of energy that the respondents ingest because of the existence of significant under-reporting (caloric amnesia). It has been shown that the discrepancy in the energy between the reported intake and the measured expenditure using the doubly labeled water method is between 20% and 50% among obese subjects. It has also been shown that the underreporting is selective among food compositions, such as fat, and there is a substantial under-eating behavior in the obese subjects (26% on average) during the assessment period. These findings have raised serious concerns as to the validity of many constructed arguments which link nutritional data with diseases. As pointed out by Blundell (J. E. Blundell, "What foods do people habitually eat? A dilemma for nutrition, an enigma for psychology," *American Journal of Clinical Nutrition*, 2000, 71(1):3-5: "If these data themselves are unreliable, then the arguments will be questionable and the conclusions will be doubtful or actually misleading".

Current assessment of physical activity is mainly based on detailed records of activity type and duration, such as aerobic exercise, strength (e.g., resistance) exercise, and sports participation. As in the case of dietary assessment, reporting errors exist. In contrast to the dietary case where few measurement tools are available, there exist a number of wearable sensors which measure body motion and dynamics (A. G. Ershow, A. Ortega, J. T. Baldwin, J. O. Hill, "Engineering Approaches to Energy Balance and Obesity: Opportunities for Novel Collaborations and Research Report of a Joint National Science Foundation and National Institutes of Health Workshop," Journal of Diabetes Science and Technology, 2007, 1:95-105 and Y. Schutz, R. L. Weinsier, and G. R. Hunter, "Assessment of free-living physical activity in humans: an overview of currently available and proposed new measures," Obesity Research, 2001, 9:368-379). Commercial systems are also available, such as SenseWear (Bodymedia, Inc., Pittsburgh, Pa.) (www.bodymedia.com/products/bodymedia.jsp). For example, Zhang et al. ("Measurement of daily physical activity," Obes. Res., 2003, 11:33-40) described a system called IDEEA which consists of five sensors attached on the chest, two front thighs, and two feet. All these sensors are wired through the body to a central unit. The IDEEA system can accurately identify 5 primary postures, 22 secondary postures, and 5 limb movements. Although IDEEA is highly accurate in motion measurement, the physical activities recognized by the system are inadequate to represent complex real-life situations. In addition, the required installation of five sensors and wiring harnesses at different body locations discourages its application in large-scale studies.

SUMMARY

Electronic systems, devices and methods are provided to accurately measure both food intake and physical activity. A novel multimedia method, an electronic device, and an integrated data processing system are described. The electronic device acquires multimedia data automatically. These data are then processed by a computer which provides a comprehensive report allowing clinicians to treat patients more effectively according to the field-acquired data. This helps healthy individuals to lose weight and keep tracking of their nutritional balance and physical activity level by self-management.

The multimedia technology forms the basis of the design. A miniature, convenient, and wearable electronic device is used to acquire and store both video and physiological data which include, but are not exclusive to, the swallowing and respiratory signals, and, optionally, environmental data. These signals can be unitized to monitor food intake and physical events constantly. The integrated system also utilizes advanced multimedia data processing algorithms to extract, organize, and summarize the acquired information.

The described devices, systems and methods are applicable to the clinical evaluation at obesity and weight management clinics where objective assessment of diet and physical activity is a critical issue. A second application of this invention is to healthy people who wish to lose weight and monitor their nutritional balance and physical activity level.

One main advantage of the described devices, systems and methods is in the use of advanced multimedia technology, which forms the basis of the design. The most unusual feature of this invention is its ability to measure both food intake and physical activity in a simple, unobtrusive, convenient, and cosmetically acceptable way, as compared to the existing designs which are often specific to one type of activity (see e.g. U.S. Pat. Nos. 6,527,711; 6,932,766 and 6,922,184).

According to one embodiment, a device is provided for remote monitoring of food intake and physical activity in a subject. The device comprises: a housing having a proximal side and a distal side; one or more physiological sensors; a video camera; a data transfer interface connected to the sensors and the video camera; and one or more power supplies. The proximal side of the housing may comprises an acoustic coupling portion, and the device may further comprise a microphone within the housing that optionally is acoustically coupled to the proximal side of the housing. The acoustic coupling portion may comprises a protuberance on the proximal side of the housing. The protuberance extends from the housing a distance sufficient to establish acoustic and mechanical coupling of the housing to a subject's skin.

According to one non-limiting embodiment, the device is formed into a "necklace", comprising a plurality of necklace portions attached to the housing wherein at least one of the plurality of necklace portions comprises one or more cables comprising one or both of one or more data transfer cables (which includes any form of data cables, such as wires and fiber optics) and one or more power cables; a secondary housing attaches to the necklace portions. The device also comprises a plurality of aesthetic features (such as beads, pearls, pendants, charms, etc.) on the plurality of necklace portions. The aesthetic features comprise one or more batteries connected by one or more power cables to the device and optionally one or more sensors connected to the device. In this embodiment, the housing is attached as a pendant from the necklace portion and the necklace portion and the housing are configured so that, when the device is worn by a subject, the housing rests over the subject's jugular notch.

In any embodiment of the device, the physiological sensor may be one or more of an accelerometer (2D or 3D), a microphone, an oxygen saturation sensor and an electrode. The device also may comprise a range finder, such as a laser range finder. The range finder may be a range finder that emits three or more laser or other coherent light beams which facilitate calculation of distances by the range finder and related processes which calculate distance. In one embodiment, the range finder illuminates an object with fiducial markers to facilitate calculation of distance to the object from another spatial point.

The device typically comprises one or more aesthetic features. The housing is preferably small, such that the housing is no larger than one or two inches in a major dimension. The video camera may be contained within the housing, or may be connected to the device so that it may be placed at a location other than at the jugular notch, which may be covered up by clothing, especially when a shirt and tie is worn by a subject. The video camera may be contained within the housing and a lens of the video camera is on a distal side of the housing. The lens of the video camera may have a depth of field of less than three feet to maximize privacy of recorded persons.

As described above, the device may further comprise one or more necklace portions attached to the housing, wherein the housing is attached as a pendant from the necklace portion and wherein the necklace portion and the housing are configured so that, when the device is worn by a subject, the housing rests over the subject's jugular notch.

Power may be supplied to the device by any useful means. In one embodiment, power is supplied by a battery (disposable or rechargeable) connected to the device. The battery may comprise one or more polymeric lithium ion batteries configured as beads or within beads or other aesthetic about the necklace portion. To assist in determining physical activity by the subject, the device may comprise one or more of a global positioning device. Other sensors include environmental monitoring sensors, optical sensors, and oxygen saturation sensor connected to the data transfer interface (that is, connected to the device).

In order to facilitate positioning and physical or acoustic coupling of the device to a subject, the device may further comprise a medically acceptable adhesive on a proximal side of the housing.

The data transfer interface may comprise one of an interface for a portable data storage device, a connector for a cable and a wireless data transmitter/receiver. According to one embodiment, the data transfer interface comprises a universal serial bus (USB) interface.

Also provided is a system for remote monitoring of food intake and physical activity in a subject, comprising any embodiment of the device described above. The system further comprises a computer (any form of suitable computing device); and a data communication device, such as a cellular phone, a mobile phone or a smart phone, for transmitting data obtained from the device to the computer. The system comprises one or more computer processes, contained in the computer or at any location(s) within the system, for determining a dimension of a food item in video data obtained from the video camera; and physical activity of a subject wearing the device in video obtained from one or both of the video camera and accelerometer. The system may further comprise one or more of: a data encryption process for encrypting data obtained from the device; a process for obscuring facial features of a person in video data obtained from the video camera; a process for distinguishing data associated with food and drink consumption from other data obtained from one or both of the microphone and accelerometer; and a process for distinguishing data associated with physical activity from other data obtained from the device. The system also may further comprise a database comprising dietary information for different foods, and a computer process for determining nutritional information from food dimension data obtained by the computer processes for determining a dimension of a food item in video data obtained from the video camera.

In another embodiment, a method of remote monitoring of food intake and physical activity in a subject is provided. The method comprises obtaining video data from a video camera suitably placed on a subject to show food consumption by the subject and physical activity of the subject; and determining from the video data one or both of food consumption by the subject and physical activity of the subject. The method may further comprise obtaining data from one or both of a microphone and an accelerometer placed on or near the jugular notch of the subject and one or both of food intake activity (e.g., swallowing) by the subject and physical activity (e.g., breathing) of the subject from data obtained from the one or both of a microphone and an accelerometer.

Also provided herein is a range finder for determining distance from a first object to an object in an image, comprising: a source of three or more coherent light beams, such as laser beams, oriented to produce fiducial markers on the object in the image; and a computer process for calculating from the fiducial markers on the object: distance to the object from the first object (e.g., a video camera or other reference point) and/or a physical dimension of an object in an image, such as: distance to the object from the first object, the physical distance between any pair of points in the image, and/or the physical area, volume or mass of an object in the image. A method of determining physical dimensions of an object in an image also is provided, comprising: illuminating the object in the image with three or more coherent light beams to produce a fiducial marker on the object in the image; producing an image of the object with the fiducial markers; and calculating one or more physical dimensions of an object and/or distances between objects in the image from the fiducial markers in the image.

BRIEF DESCRIPTION OF THE DRAWINGS

The figures are provided for illustrative purposes only and are not intended to limit the scope of the present invention(s).

FIG. 2A: An image of an outdoor scene recorded during running; FIG. 2B: A graphical representation of computed step frequency and motion characteristics based on x-projections; FIG. 2C is a graphical representation showing calculated slope changes based on y-projections.

FIG. 9 provides images of simulated effects of our privacy protection methods.

(FIG. 11B) shifts of a walking video).

FIG. 14A is a confusion matrix of food categorization accuracy. FIG. 14B shows some correct food labeling results.

DETAILED DESCRIPTION

Figure 1A:
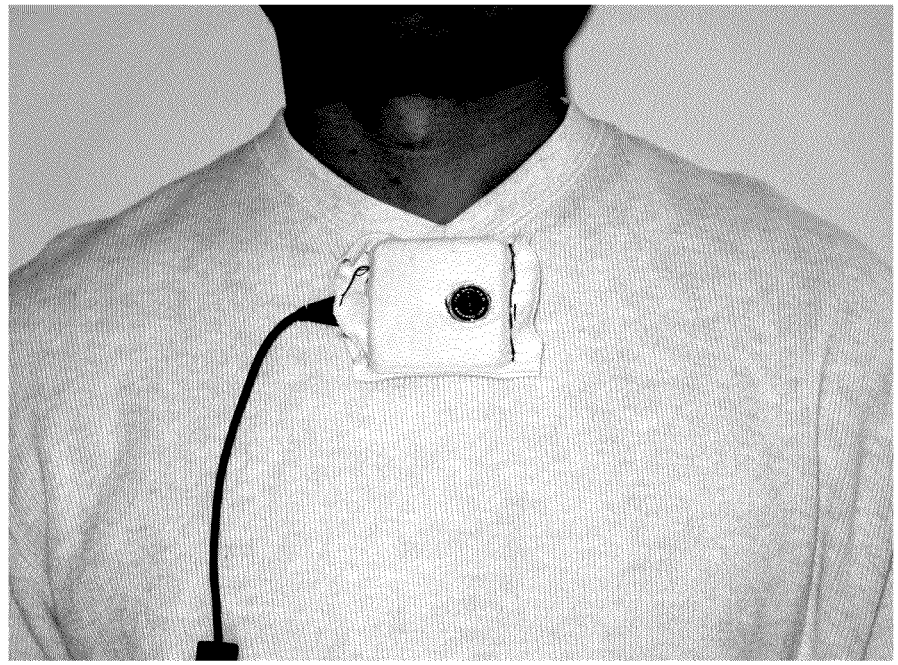
FIG. 1A is a photograph showing placement of a web camera attached in the area of a jugular notch.

Provided herein are devices, systems and methods useful for monitoring food intake and activity in a subject, such as a human. These devices, systems and methods may be implemented in a research setting and/or in a monitoring/treatment setting for an individual.

As mentioned above, one major difference between the e-chronicle (electronic chronicle) approach to the assessment of diet and physical activity described herein and the existing approaches is in the use of extensively recorded objective video. As an electronic visual memory, this powerful technology stores all the scenes that the individual has observed while performing various tasks throughout the entire recording period. Since "seeing is believing", the e-chronicle system described herein allows more complete event understanding than any of the existing non-video based methods. Unlike the traditional video surveillance systems which can only replay the recorded events manually, the described e-chronicle system is an advanced intelligent system with a unique ability to computationally extract and index the events of interest. As a result, the workload for "mining data" from the e-chronicle is greatly reduced. The e-chronicle also acts as a "trustful agent" that filters out the appearance of people and excludes human images from observation/identification by other humans.

The report of food intake by free-living individuals is subject to error. When individuals record their intake for subsequent analysis, they generally underreport their intake, when compared to estimates of intake based on energy expenditure by doubly-labeled water (DLW) and the absence of a change in body mass during the observation period. And, when asked to record their intake, subjects may change their eating habits, often reducing intake, presumably because they are paying more attention to what they actually are consuming. Hence, the record of intake does not represent what they would normally be ingesting. The record of intake is nonetheless of great interest, beyond a measure of total energy intake (or expenditure), because it provides an indication of what has been eaten, affording a calculation of what nutrients have been consumed and in what amounts, and it also provides a record of the timing of food ingestion. Such information is extremely useful, for example, in advising obese individuals on how to modify their diets to lose weight. However, if the information provided is inaccurate, its usefulness is limited. An accurate method for measuring food intake in real time, which would allow identification of the foodstuffs consumed, the amounts, and the timing over the 24-hour period, would thus be extremely useful. In advising the obese on weight loss strategies, it would enable the clinician and/or dietician to make better, more informed recommendations to patients on modifying dietary habits to improve the timing and composition of foods consumed, while optimizing palatability and acceptability. Patients are unlikely to be compliant with dietary recommendations for very long, if they do not fit with their basic food and eating preferences. And such preferences cannot be identified if accurate reporting of eating habits is absent.

Physical activity includes not only purposeful exercise programs, but also a variety of transportation, home-keeping, and work routines that are physical in nature. It has been an enormous technical challenge to design a convenient and inexpensive system to identify, characterize, and quantify all physical events performed by individuals. The devices, systems and methods described herein can meet this challenge.

Because voluntary movements of the human body (e.g. walking, jogging, running) are accompanied by direction-varying perturbations (such as periodic swings) in the video images acquired by a recording device, automatic identification of physical movements undertaken by the individual can be evaluated and identified using change detection algorithms. Information such as location and altitude can also be obtained using Global Positioning System (GPS) technology (within the resolution of the GPS system). With the data from both sources, the detected motions can then be classified according to the type of movement as well as to various other parameters. For example, during walking, the pace of the walk (pace frequency), variations in slope (horizontal/inclined surface), and distance traveled can be determined computationally. As shown in Example 7, below, the weight of a load and placement of that load can be calculated from video data. In addition, knowledge of a subject's physically active and inactive periods, along with the information extracted from respiratory events, makes it possible to estimate not only the total energy expenditure, but also the resting metabolic rate (RMR) which is of a great interest in the metabolic study of obesity.

In most cases, bodyweight is clinically managed by dietary control and physical exercise. For many individuals, the long-term success of this method is unsatisfactory because of their psychological and emotional resistance to the routines involved. Recent physical activity guidelines have emphasized the accumulation of shorter episodes of moderate physical activity which may include those routinely performed for living, work, and recreation. Similarly, a flexible dietary plan emphasizing the favored foods of an individual but, on average, limiting portion size, and therefore energy input, is more appealing and likely to produce an enduring effect. The design of a highly individualized weight control program requires detailed information about the individual's living and working environment, cultural background, and lifestyle. The technology described herein provides a unique platform to acquire such information using both video and optionally GPS data, making this design practical. For example, an individualized weight management plan may include certain lifestyle related items such as: jogging in a nearby park, walking a family dog in a specifically designed route, climbing stairs at work, and working in a garden, growing vegetables of certain preferred types, maintaining the garden daily without using power tools, and consuming the harvest. Again, the implementation of these plans can be monitored closely by the described technologies and evaluated with respect to energy balance estimates derived from the e-chronicle constructed for the individual.

The systems provided herein, including related methods and devices, utilize recorded video which forms an electronic record of the visual history. The data typically are recorded continuously over a time period or determined by a swallowing or respiratory event. The systems also comprise one or more physiological sensors, such as a microphone to record swallowing and respiratory signals which may be used to turn on or off the camera, and, optionally speech, a laser range finder (for measuring the distance of the camera to food and the dimension (portion size) of the food), a microphone (for respiration and swallowing), an accelerometer (for body acceleration), an optical sensor (for skin movement due to swallowing), an oxygen saturation sensor (for blood oxygen level and heart rate), a pair or an array of skin-surface electrodes (for skin impedance), etc. The systems also optionally comprise a GPS device. Any element of the device is considered to be "connected" to one or more other elements of the device when it is physically attached in any manner to the device and, where appropriate for a specific element, the element is in data communication with other elements of the device and/or able to receive power from and/or transfer power to (e.g., in the case of batteries) other elements of the device, as is appropriate for the specific element and its relationship to other elements of the device. These recording modalities inevitably raise serious concerns regarding privacy. However, methods may be employed to ensure the privacy protection of the human subjects as well as other individuals with whom they would come in contact. This privacy issue is addressed in greater detail below. According to certain embodiments, several security layers of privacy protection may be implemented in a concatenated fashion. Multi-layered protection is believed necessary to guard against any possible system failure. A first security layer may be to hardware-install specially designed electronic components to limit the scope (depth of field) of the video camera and to cancel the speech signal. A second security layer can be to use advanced encryption of all multi-media data. Preferably, no human will be allowed to access any information during data recording, transmission, and transportation. A third security layer can be an extensive filtering implemented by the e chronicle software. For example, all images of humans appearing in the entire video record may be automatically identified and destroyed. In addition, a neural network classifier can be utilized to identify and destroy all speech sounds. Again, no human needs to be involved in this security layer. In a last security layer, passwords can be used to allow authorized persons, who are required to sign a legal document of non-disclosure, to access the e-chronicle. This access is possible only after all the previous security layers are automatically implemented. In addition to the three layers of privacy protection, a convenient mechanism can be provided by the systems to switch-off or block the camera in sensitive locations or public places where photographing or video taking is prohibited.

The proposed sensor and e-chronicle system may comprise advanced electronic and computational technologies. However, high-technology devices do not have to be expensive. The hardware cost of the system will be mostly determined by the miniature sensor device, which contains a video camera, one or more physiological sensors, and supporting electronics. Nevertheless, the described devices, when produced in a reasonable quantity, will be relatively inexpensive to make. Methods of transmitting data to the e-chronicle software vary, and include, without limitation, transmittal by cell-phone (smart phone); wireless (e.g., spread spectrum) technology, such as by Bluetooth, IEEE 802.11g or ZigBee, protocols; or by physical transfer of small mass storage devices such as flash storage devices, including compact flash, smartmedia or USB key flash drives. It is believed that the systems described herein will be financially feasible for both clinical and research applications.

A device is provided for monitoring food intake and physical activity in a subject. The device comprises a housing comprising a video camera and, selectively, other types of sensors, such as a range finder (for measuring the distance of the camera to food and the dimension (portion size) of the food), a microphone (for respiration and swallowing), an accelerometer (for body acceleration), an optical sensor (for skin movement due to swallowing), an oxygen saturation sensor (for blood oxygen level and heart rate), a pair or an array of skin-surface electrodes (for skin impedance), etc. Suitable miniature video cameras, microphones, accelerometers (2D or 3D), and some other sensors are readily available from a number of commercial sources. Two embodiments of a range finder, specifically, a laser range finder, are provided in the Examples. Range finders based on non-laser technologies are possible, but laser range finders may be preferred in the miniature devices and related systems described herein. The sensors may be contained within the housing or in separate housings attached and/or connected to the device, such as, according to one non-limiting embodiment, within decorative beads (e.g., "pearls"), other aesthetic features and/or other portions of the device, such as a back unit (housing in the back of the neck), such as in a necklace embodiment of the device as described herein. The housing or other portion of the device optionally comprises a vibrator, a GPS device (Global Positioning Device) and other environmental monitoring sensors, such as a daylight/indoor light sensor, a thermometer, a humidity meter, an X-ray exposure sensor, and/or one or more air quality sensors for a variety of pollutants, microorganisms, allergens, and carcinogens. The components of the device, such as pendants, housings, back housings, "beads" or other aesthetic features, are selected according to the particular scientific or clinical study and typically are one inch or less in size. Signals from the sensors, video camera and GPS device are amplified and/or processed, as is necessary and/or desirable to produce a data stream. Analog signals typically are converted to digital signals using analog-to-digital converters and may be compressed according to any useful standard, such as MPEG4. The device also comprises a power supply, which may be a battery or a parallel or serial connection of a number of batteries. The battery or batteries may be placed anywhere within the device, such as in a unit behind the back (back unit), within "beads", linked by the cables inside a necklace or within any housing and/or aesthetic feature of the device.

The device also comprises a communications subsystem. The communications subsystem is an element or combination of elements that is configured (selected, arranged, etc.) to transfer data from the device to a computing device, optionally over a data network, such as a mobile or fixed telephone network (including VoIP and the like), and the internet. In one embodiment, the communications subsystem comprises a portable data storage device, such as a USB key or a digital media card, along with an appropriate connector/interface for transferring data from the device to the portable data storage device. The data stream may be temporarily stored in a memory module included in the device for transfer to the data communication subsystem. In another embodiment, the data communication subsystem comprises an interface, such as a USB, or any other interface useful in transferring data from one electronic component to another, for communicating data from the device to a mobile data communications device, such as a smart phone for continual or periodic transfer of acquired data over a communications network to a remote computer with an interface capable of receiving data. In yet another embodiment, the device comprises a short-range (e.g., less than approximately 100 feet) wireless data communication device, such as a Bluetooth or ZigBee transmitter, and optionally receiver, which transfers data acquired from the device to a data communication network via a suitable communications device, such as a mobile data communications device or a wireless access point of a data network, such as a computer network. As can be appreciated by those of skill in the art, given the present disclosure, there are a myriad of options as to how to effectively transfer data acquired by the video camera, and physiological and environmental sensors, including an accelerometer, GPS device etc. of the device to an external location (not on the subject).

The device may comprise one or more aesthetic features, namely, one or more features that do not relate to function of the device, but are included for aesthetic or decorative reasons. Aesthetic features include the shapes of the device, housing, and associated components, including necklace, "pearls", and back unit, the colors or color schemes of the device, housing, and associated components, and the materials used to manufacture them. For example, aesthetic features include the configuration of the device into a necklace with a decorative pendant, such as described below, or a tie pin, clip or button.

Configuration of the device, including choice of video camera, physiological and environmental sensors, vibrator, GPS device, power supply, communication subsystem and aesthetic features is a matter of design choice and device optimization. Additional electronic elements, including, without limitation: resistors, capacitors, PCB boards, A/D converters or other data converters, integrated circuits, filters, wires, cables, data storage memory (e.g., ROM, RAM, flash memory, etc.) connectors, power supply and data and power cables within the necklace, GPS and wireless communication antennas within the necklace or by part of its sheaths, and power supplies (e.g., batteries) placed within the device or "pearls", etc. may be included in the design of the device and system to accomplish the desired goal of operating the system and obtaining and transferring data in a form useful for the purposes described herein. Given the teachings of the present disclosure, a person of skill in the art will be able to configure the various elements of any embodiment of the device or system described herein to achieve the object of operating the system and obtaining and transferring data to and from the device and components thereof.

Data acquired from the device are transferred to a computer comprising one or more processes for carrying out the methods described herein. As described herein, processes, including database functions, algorithm implementation, data analysis, privacy protection, encryption, video processing, Graphical User Interface (GUI), etc., may be implemented on a single Personal Computer (PC), laptop, workstation, etc., with computing functions being implemented locally on one computer or distributed in any fashion among two or more computer processing units. As used herein, a computer refers to any variation in computer implementation, including local, remote or distributed processing. Thus, a computer comprising one or more processes for storing and/or analyzing data acquired from the device includes, without limitation, any configuration of computer(s), computer hardware, processors, computer software and/or data storage (temporary, such as RAM, or long-term, such as hard drive) that is useful in performing the stated tasks/processes. Implementation of algorithms and tasks described herein is believed to be within the abilities of those of skill in the art using suitable software and/or hardware.

Provided are systems for obtaining and processing data related to food intake and physical activity of a subject. The systems are an extension of the above-described device, to include any embodiment of the device, a remote computer comprising one or more processes for storing and analyzing data acquired from the device and any useful data communication device for transmitting data from the device to the remote computer, such as any embodiment described herein. Non-limiting examples of processes that the remote computer comprises (is configured, contains, is modified to carry out, etc.) include, as described herein, suitable interfaces, database functions, privacy functions including processes for identifying and obscuring faces of videotaped individuals and/or spoken language acquired by the device.

In another embodiment methods are provided for measuring food intake and physical activity, comprising obtaining continuously-recorded video data and esophageal sound and/or accelerometer data from a subject and determining from the data food intake of the subject. The method may utilize any device and/or system described herein. It should be noted that by "continuous", it is meant that data is recorded over a time period with little or no interruption. Interruptions may occur when the device is not worn, when the video camera is set in "automatic mode", for instance, controlled by swallowing or respiratory events, or it is temporarily shut off manually for any reason.

Example 1

In order to study the effectiveness of using the multimedia technology for dietary assessment, we conducted experiments using a compact digital web camera (SiPix StyleCam Blink, dimensions 2.22×2.22×0.65 inch, focal length 6.3 mm, aperture size F3.0). This camera (left panel in FIG. 1) records digital video (320×240 pixels at 30 frames per second (frames/s)) and transmits data to a USB port of a computer. One snap shot of a breakfast video is shown in the right panel FIG. 1: Left: A web camera is attached in the area of jugular notch; Right: Breakfast items with computer assisted measurements of FIG. 1. The goal of this study was to measure the volume, weight, and calories of food by video and image processing. The measurement was semi-automatic, i.e. assisted by an observer. For most foods (e.g., an uncut chicken, salad in a container, and fruits), we roughly know their shape, but their size may vary considerably. Since the shape knowledge is available, it is often possible to estimate its volume from a single perspective. In order to realize this possibility, we investigated the 3D projection problem and answered a critical question: how does a line of pixels in an image correspond to a line on the food? We have derived a formula relating them by $$L = \frac{H}{j_1 \cdot j_2 \cdot d_y} \sqrt{(i_1 \cdot j_2 - i_2 \cdot j_1)^2 d_x^2 + (j_1 - j_1)^2 f^2},$$

where f, $d_x$, $d_y$, ($i_1$, $j_1$), ($i_2$, $j_2$) and H are, respectively, camera focal length (known), size of CCD cell dimensions (known), image coordinates (in pixels) of the ends of line (known), and the vertical distance from the camera to the top of dining table (estimated). With this relation, the pixel and its physical object correspondent can be one-to-one mapped. For example, when an electronic ruler is utilized to gauge certain points on the food/drink, the measured distance (in number of pixels) can be converted to physical length (see the right panel). Consequently, the volume, weight, and calories can be computed using the shape knowledge and a USDA National database (see, e.g., U.S. Department of Agriculture and Agricultural Research Service, "USDA nutrient database for standard reference, Release 19," available in Nutrient Database Laboratory Home Page, 2006, (www.ars.usda.gov/ba/bhnrc/ndl) and U.S. Department of Agriculture, Agricultural Research Service. 2007. USDA National Nutrient Database for Standard Reference, Release 20. Nutrient Data Laboratory Home Page, (www.ars.usda.gov/ba/bhnrc/ndl)).

Figure 2A:
FIG. 2A-2C.
Figure 2B:
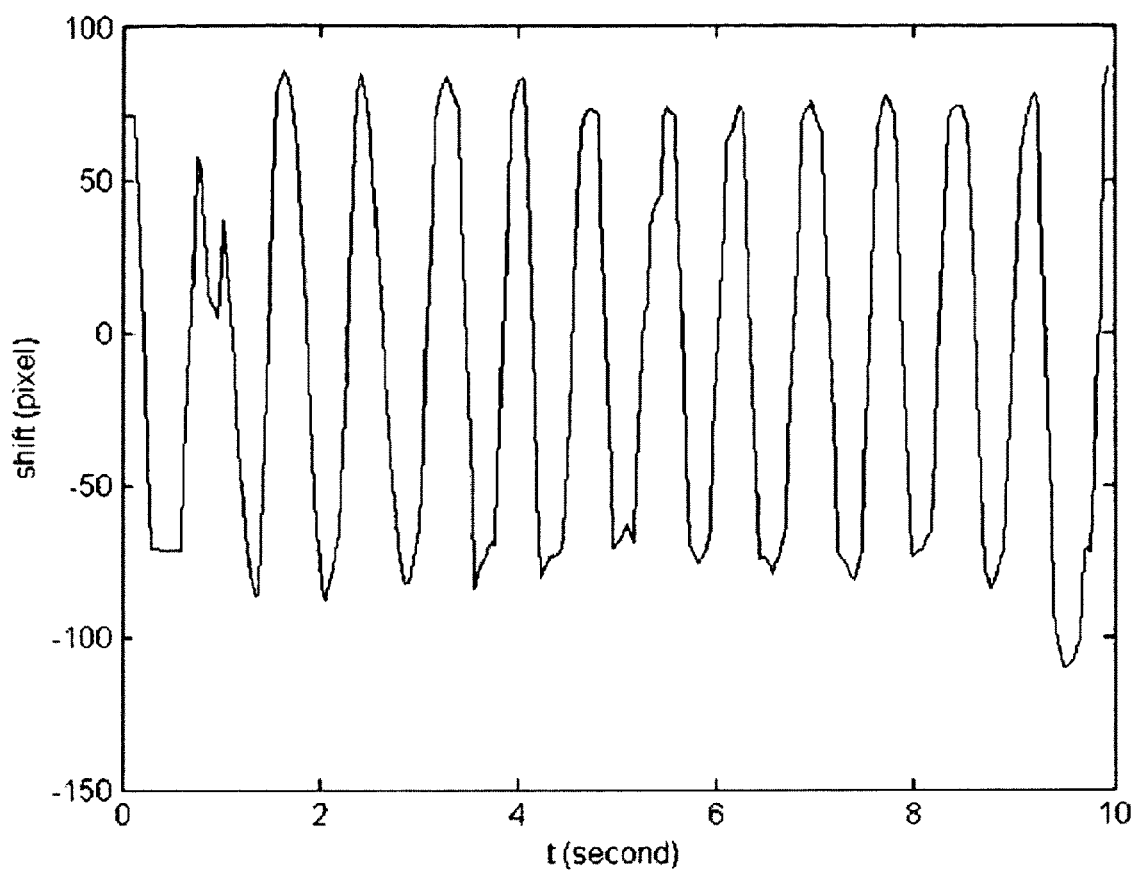
Figure 2C:
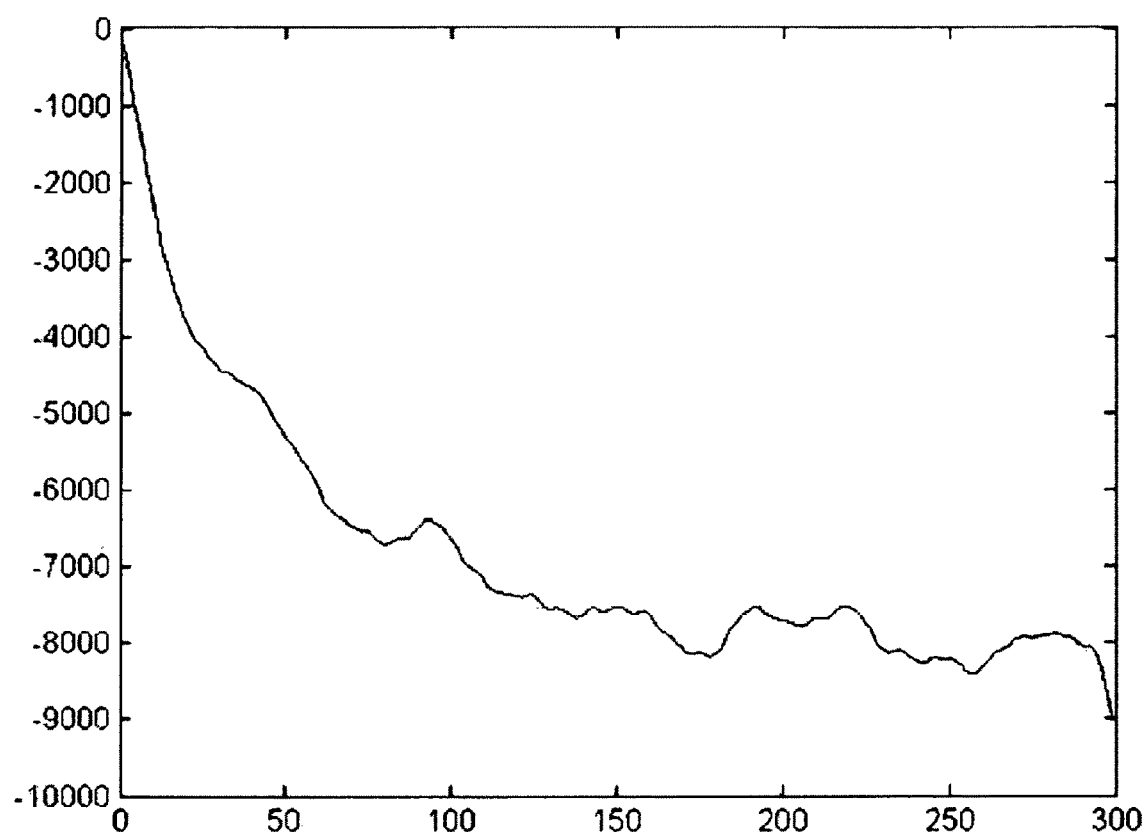

The recorded video is effective for measuring not only food intake, but also physical activity. In a study of walking and running, we performed experiments using a SONY DCR-TRV20 camcorder affixed to the center of the lower neck while performing these activities. During replay of the recorded video (FIG. 2A), we observed interesting characteristic swings of the outdoor scene. At most times, human observers were able to correctly tell whether the person was walking or running, and whether the terrain was up-hill or down-hill. Encouraged by these observations, we utilized video processing techniques to perform quantitative measurements. We developed a simple method to assess the observed displacements by first computing the x- and y-projections within video frames and then evaluating the cross-correlation values between frame pairs. FIG. 2B shows the result of a running example calculated from the x-projections. The frequency and motion characteristics during the 13 running steps can be clearly observed. Using the y-projections and a smoothing filter, we were able to characterize the slope changes over a distance (FIG. 2C).

Figure 3A:
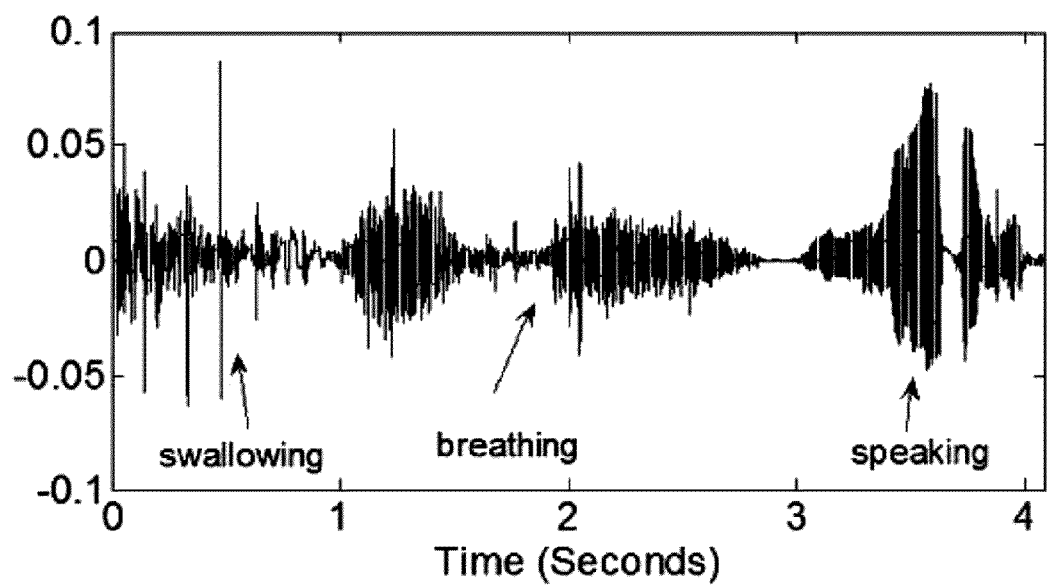
FIG. 3A is a raw waveform of a microphone signal.
Figure 3B:
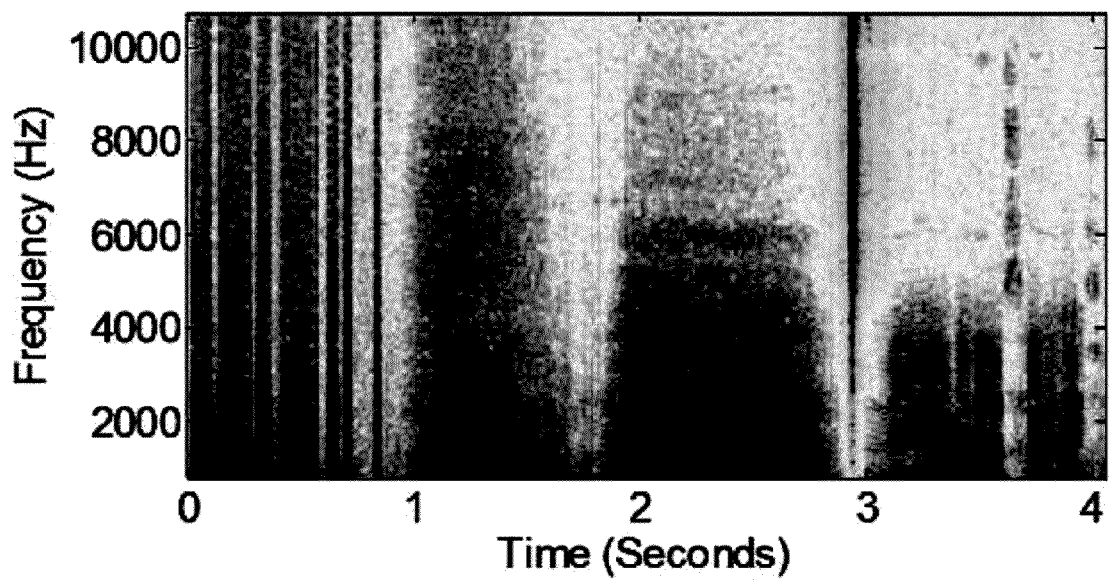
FIG. 3B is a raw spectrogram of a microphone signal.
Figure 3C:
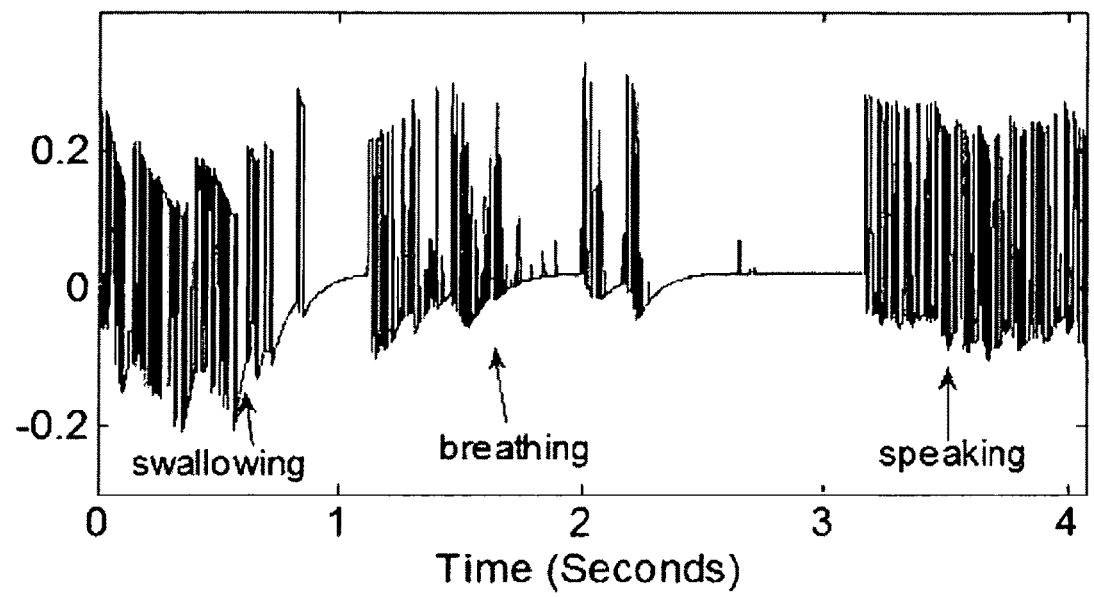
FIG. 3C is a raw waveform of an accelerometer signal.
Figure 3D:
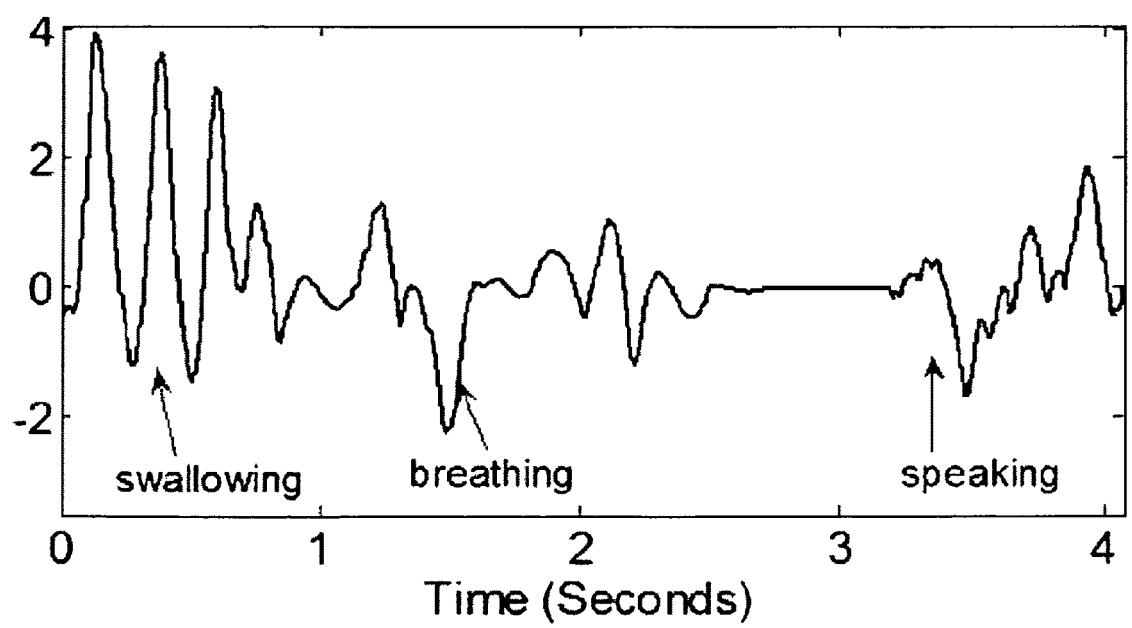
FIG. 3D is an integrated waveform of an accelerometer signal.

Respiration and Swallowing Signal Acquisition: One embodiment of the device uses two physiological sensors, a microphone and an accelerometer to jointly monitor the swallowing and respiratory events. These signals are used not only for evaluation of food intake and physical activity, but also may be used control signals to turn on and turn off the video camera for the purpose of conserving battery power and recording only the relevant data. Specifically, once several continuous swallowing or stronger-than-the-baseline respiratory events are detected, the video camera is automatically turned on for video or image recording. A computer process implemented by the device may be used to accomplish this. Once these activities stop for a pre-defined period of time, the camera may be automatically turned off. There exists a large body of literature on recording these signals at the neck region as well as various data processing techniques employed (G. Sierra, V. Telfort, B. Popov, M. Pelletier, P. Despault, R. Agarwal, V. Lanzo, "Comparison of respiratory rate estimation based on tracheal sounds versus a capnograph," IEEE EMBS 2005, 2005, 6145-6148; H. Wang, L. Y. Wang, "Continuous intro-operative respiratory auscultation in anesthesia," Proc. of IEEE Sensors 2003, 2003, 2:1002-1005; A. Yodollahi, Z. M. K. Moussavi, "A robust method for estimating respiratory flow using tracheal sounds entropy," IEEE Trans. on Biomedical Engineering, 2006, 53(4): 662-668; and H. Firmin, S. Reilly, A. Fourcin, "Non-invasive monitoring of reflexive swallowing," Speech Hearing and Language: work in progress, 1997, 10: 171-184). In order to verify these results, we affixed a miniature piezoelectric cartridge microphone (TypeWM 60-PC, Jameco Valuepro, Ltd.) and a MEMS accelerometer (Type SQ-SEN-200, SignalQuest Inc.) at the jugular notch. The output signals, after preconditioning and amplification, were simultaneously recorded. The data obtained were generally satisfactory although substantial friction noise was present if the sensors were not securely affixed to the skin. While the microphone was sensitive to the acoustic emission during swallow and respiration, the accelerometer seemed to be more responsive to the organ motion associated with these activities. FIGS. 3A and 3B show segments of simultaneously recorded raw waveforms while the human subject performed swallowing, breathing, and talking in a sequence. 3C and 3D provide the spectrogram of the microphone signal and the result after double integration of the accelerometer signal. Clearly, these processed forms facilitate pattern recognition and classification described below.

Figure 4:
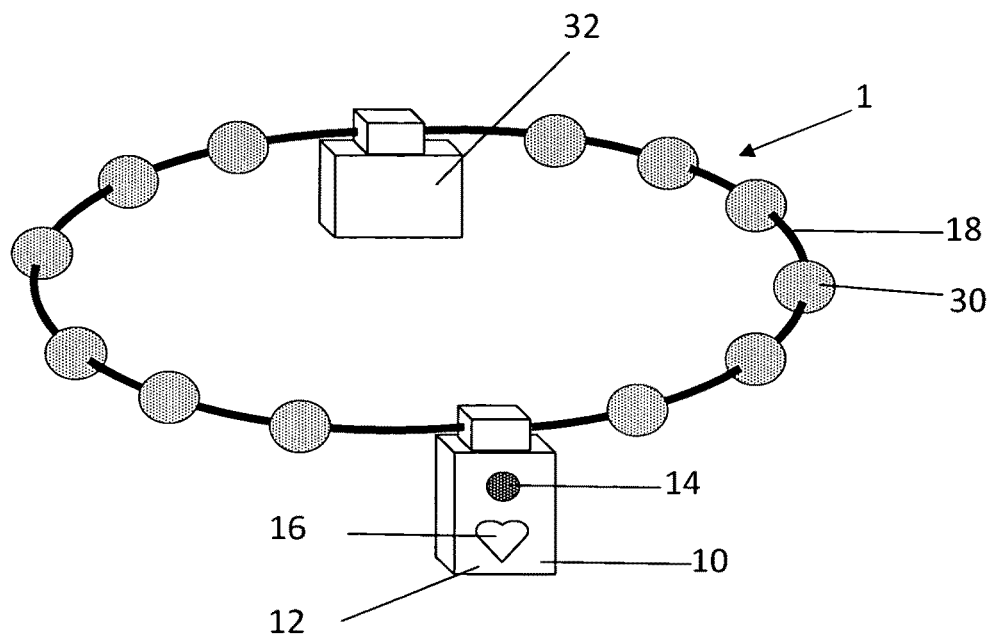
FIG. 4 is a schematic diagram of one embodiment of a "necklace" device as described herein.

Electronic Design: FIGS. 4-7 are illustrative and schematic in nature and are provided to illustrate certain examples of the devices described herein, and are not intended to be limiting. FIG. 4 shows one embodiment of the device described herein. Device 1 comprises pendant 10. Pendant 10 comprises a housing 12 and a video camera showing lens 14 on a distal side of housing 12. Aesthetic feature 16 also is shown. Cable 18 forms a necklace portion of the device 1. Attached to cable 18 are beads 30 (e.g., pearl colored and sized beads, giving the device the appearance of a pearl necklace) comprising rechargeable polymer lithium ion batteries to power the device 1. Any type of batteries can be used for this purpose and housed within the beads 130 or other aesthetic features, though polymer lithium ion batteries may be favored because they can be manufactured into a variety of shapes and sizes. Attached to the cable 18 is a communications interface 32. The communications interface 32 may comprise without limitations an interface for a portable memory device, such as a USB key, or a smart compact flash card or another flash memory device, or the like; a cable connector, such as a USB port, for transferring data to a device, such as a smart phone, or a computer network; and/or a wireless interface, such as a Bluetooth transmitter/receiver. As mentioned elsewhere, design, configuration of the various parts, including wiring, choice of connecters and electronic elements, etc. are well within the abilities of a person of skill in the relevant arts.

Figure 5:
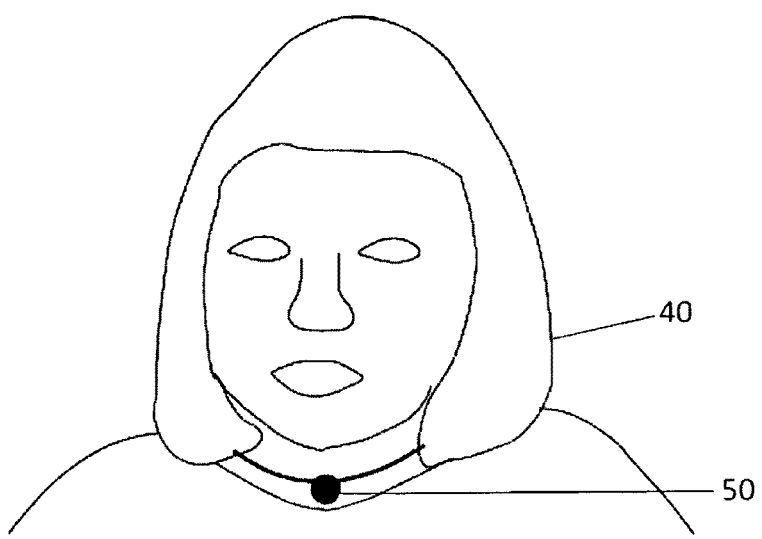
FIG. 5 illustrates placement of one embodiment of a "necklace" device as described herein.

FIG. 5 depicts one embodiment of a pendant 50 on a subject 40.

In the necklace embodiment, such as in the necklace shown in FIG. 4, the aesthetic features can be any useful forms of attachments, such as beads (shown, for example, in FIG. 4), charms, pendants, etc. in a variety of shapes, sizes and colors. These attachments are not necessarily only decorative objects, but also can serve as housings for rechargeable polymer lithium ion batteries, sensors and/or circuits that cannot be placed within (e.g.) the pendant and back unit because of their size and weight limitations. In addition, these attachments can serve as platforms for custom sensors as payloads for a variety of scientific or clinical studies requiring the acquisition of environmental, physiological, and behavioral data. These optional payload sensors include, without limitation, a GPS receiver for geological location sensing, an accelerometer for body movement sensing, a light sensor for indoor/outdoor assessment, a thermometer, a humidity meter for weather and indoor conditions, an acoustic sensor for environmental noise level, an X-ray sensor for sun exposure, and one or more, or an array of air quality sensors for a variety of pollutant, microorganism, allergen, carcinogen, and other chemical sensing. Some of these sensors are commercially available and useful without modification, while others may need to be designed or modified to suit this particular application. Typically, the device/system provides standard data and power interfaces to allow these payloads to be used in the plug-and-play fashion.

The necklace also serves multiple functions. The cable (e.g., sheath) may contain data and power cables. In addition, one or more radio-frequency antennas for wireless communication and GPS signal reception may be placed in the cable. Where applicable, there may be one or more connectors inside each pearl or other aesthetic feature comprising a power supply and/or sensor for appropriate routing of data and power. The length of the necklace preferably is adjustable so that the pendant can be securely placed on top of the jugular notch.

The back unit servers many purposes, such as: 1) a weight balance for the system to improve comfort in wearing the device while producing a suitable tension force P2 (see below) allowing the pendant in physical contact with the skin, 2) an additional housing for sensors, electronic circuits and/or a rechargeable lithium ion battery, 3) a data processing and storage center, and/or 4) a communication hub when a wireless or wired communication channel is installed for the system.

Figure 6A:
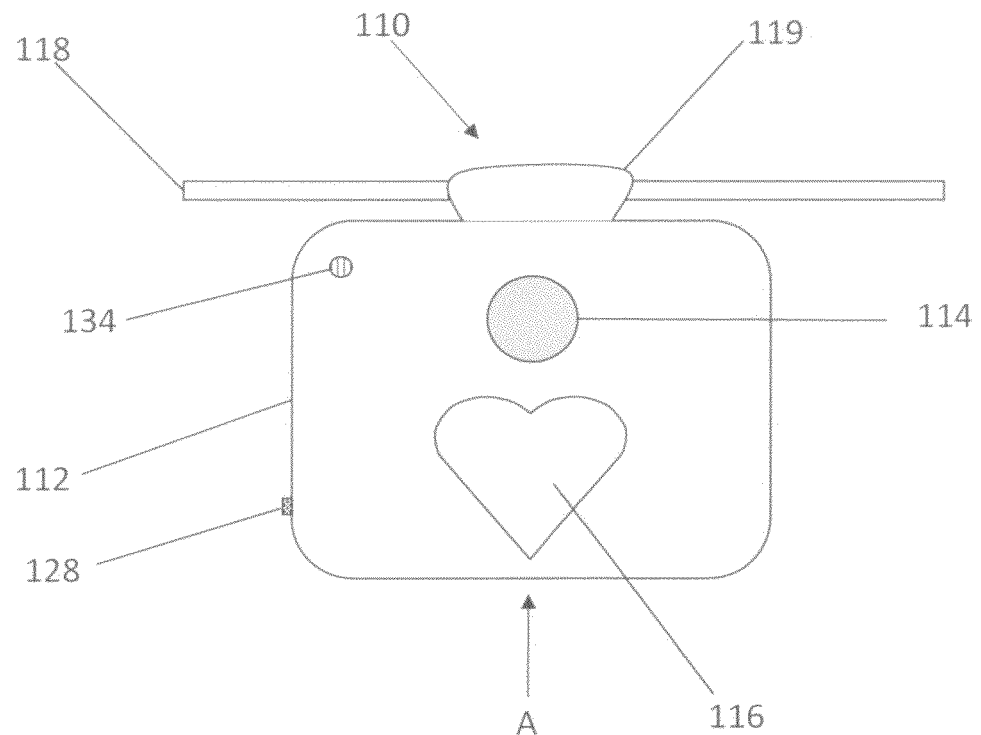
FIGS. 6A, 6B and 6D are schematic diagrams of one embodiment of a pendant device as described herein.
Figure 6B:
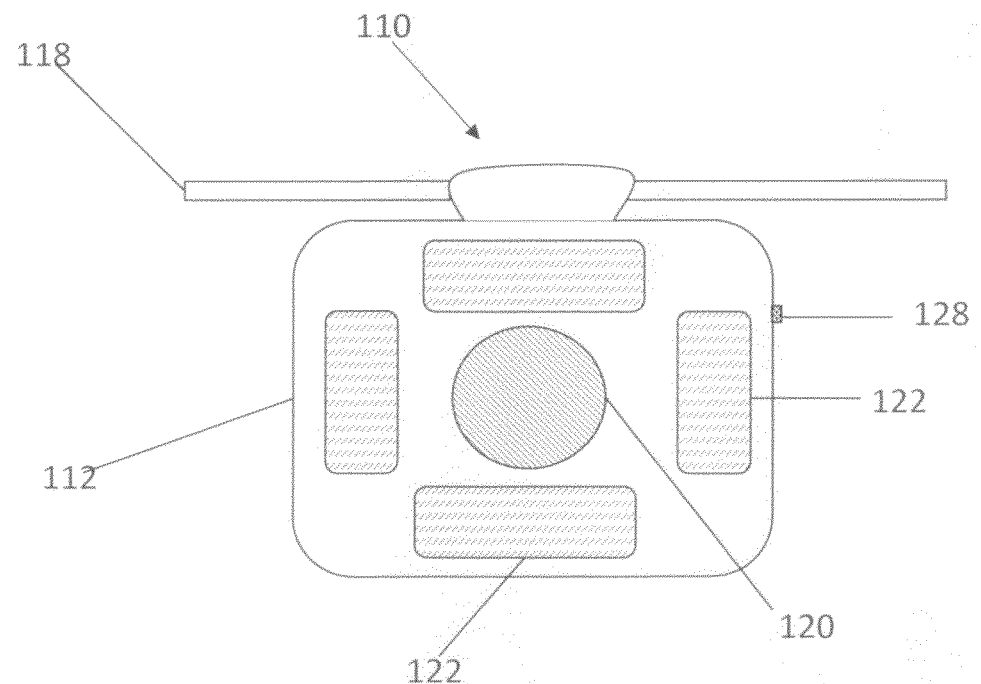
Figure 6C:
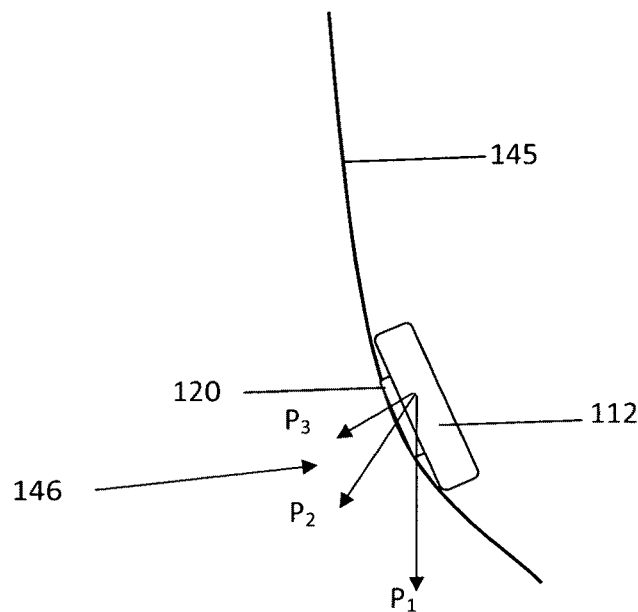
FIG. 6C shows placement of the pendant in a jugular notch, and associated force vectors.

The overall design of one embodiment of a pendant, such as pendant 10 is shown in FIGS. 6A-6C. FIG. 6A shows a view of a distal side (away from a subject's body when worn) of a pendant 110. Pendant 110 comprises a housing 112 containing a video camera with a lens 114 on a distal side of housing 112. Also shown is an example of an aesthetic feature 116 on the housing 112. Housing 112 hangs from a cable 118 (e.g. necklace portions) which comprises wires for transferring data to and from the pendant 110 and transferring power to the pendant 110. Tab 119 joins housing 112 and cable 118. A switch 128, is shown on the side of the pendant 110, allows the user to manually turn on and off the device, video camera and/or other elements of the device. Housing 112 or other components/elements of the device may contain a vibrator, e.g., to inform the human subject status of the system, for example and without limitation, by using a set of predefined code patterns. A phase mask 134 or lens of a laser range finder is exposed through an opening in the device housing. The laser range finder is used to measure distance between the camera and food. By knowing the distance, the food dimensions on the recorded pictures or video frames can be determined (see, e.g., Example 3, below). The laser range finder typically produces at least three beams. These beams are generated by individual laser diodes, or by splitting a single laser beam from a laser diode using an optical system such as a phase mask.

FIG. 6B shows a proximal side (towards a subject's body when worn) of the pendant 110 of FIG. 6A. Housing 112 is depicted in this embodiment as housing a coupling portion 120 (e.g. an acoustic coupling portion) for physically coupling housing 112 to the subject's skin, thereby improving transfer of sound, such as swallowing noises, from the subject to the pendant 110. Switch 128 is shown.

In this particular embodiment, physical coupling of the housing 112 to the subject is accomplished by use of adhesive pads 122, which maintain pendant 110 in a fixed position on a subject with sufficient physical coupling. Adhesives and adhesive pads can be any useful shape, composition and thickness. For instance, the adhesive pads 122 may be a sing, contiguous ring, oval, rectangle, etc. In one embodiment adhesive pads 122 are a single pad that adheres to the housing 112 around or substantially around the coupling portion 120, with a greater strength than to the skin of a subject, but not so strongly that the adhesive pad(s) 122 cannot be fairly easily removed from housing 112, so that new adhesive pad(s) 122 can be replaced when needed.

In certain embodiments, adhesive is not necessary. An illustration of this is provided in FIG. 6C, showing pendant 110 on a subject's neck skin 145 at the jugular notch 146. In such a case, the gravity force produced by both the weight of the pendant, P1, and the tension force, P2, resulting from the necklace around the neck jointly produce a component force, P3, in the opposite direction of the surface norm of the skin. Component force P3 effectively holds the pendant to the skin when the body is still or in a mild movement. During heavy physical activity, such as running and jumping, it may become necessary to apply additional force to hold the pendant to the skin for improved physical coupling. In such an instance, adhesive may be used, as described above.

Figure 6D:
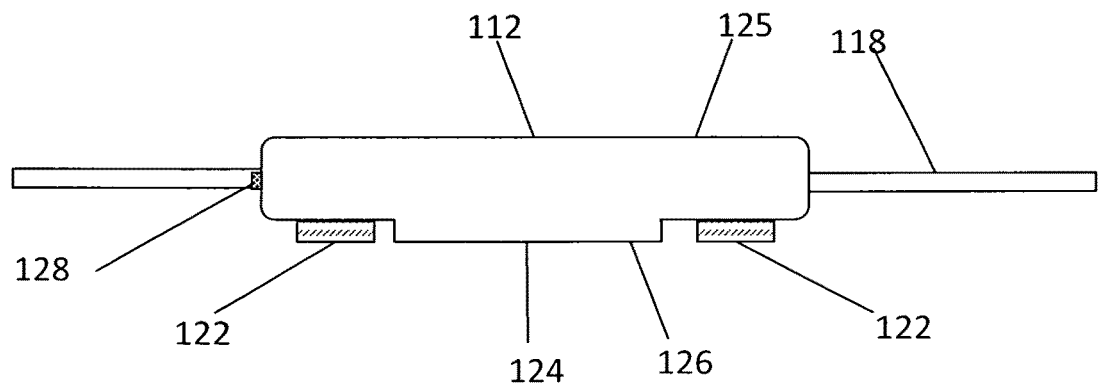

FIG. 6D shows a side view of the pendant 110 shown in FIGS. 6A and 6B from viewpoint A, shown in FIG. 6A, FIG. 6D shows the housing 112, cable 118, adhesive pads 122 coupling portion 124, and switch 128, as well as indicating the distal 125 and proximal 126 sides of the housing 112. Coupling portion 124 is shown as a protuberance with a square profile. As is evident a protuberance can have any useful profile, such as a curved profile.

The pendant-like device for example as shown schematically in FIGS. 6A-6D, referred to here as an electronic pendant, can be affixed at the jugular notch, connected by two cables inside necklace-like sheaths, such as cables 118 of FIGS. 6A-6C and cable 18 of FIG. 4. Electrical connectors are used between the sheaths and the pendant for data and power connections. This design is more suitable for women who represent approximately 80% of the patient population at a typical clinical unit.

For men, or others who do not wish to wear the "necklace" embodiment described above, the device can be covered by a tie or shirt (e.g., a neck shirt) with the camera lens exposed in any useful manner. For example, as shown in FIG. 7A-7B, the video camera can be configured in the form of a tie pin or other type of pin and connected by wire(s) to an electronic pendant.

Figure 7A:
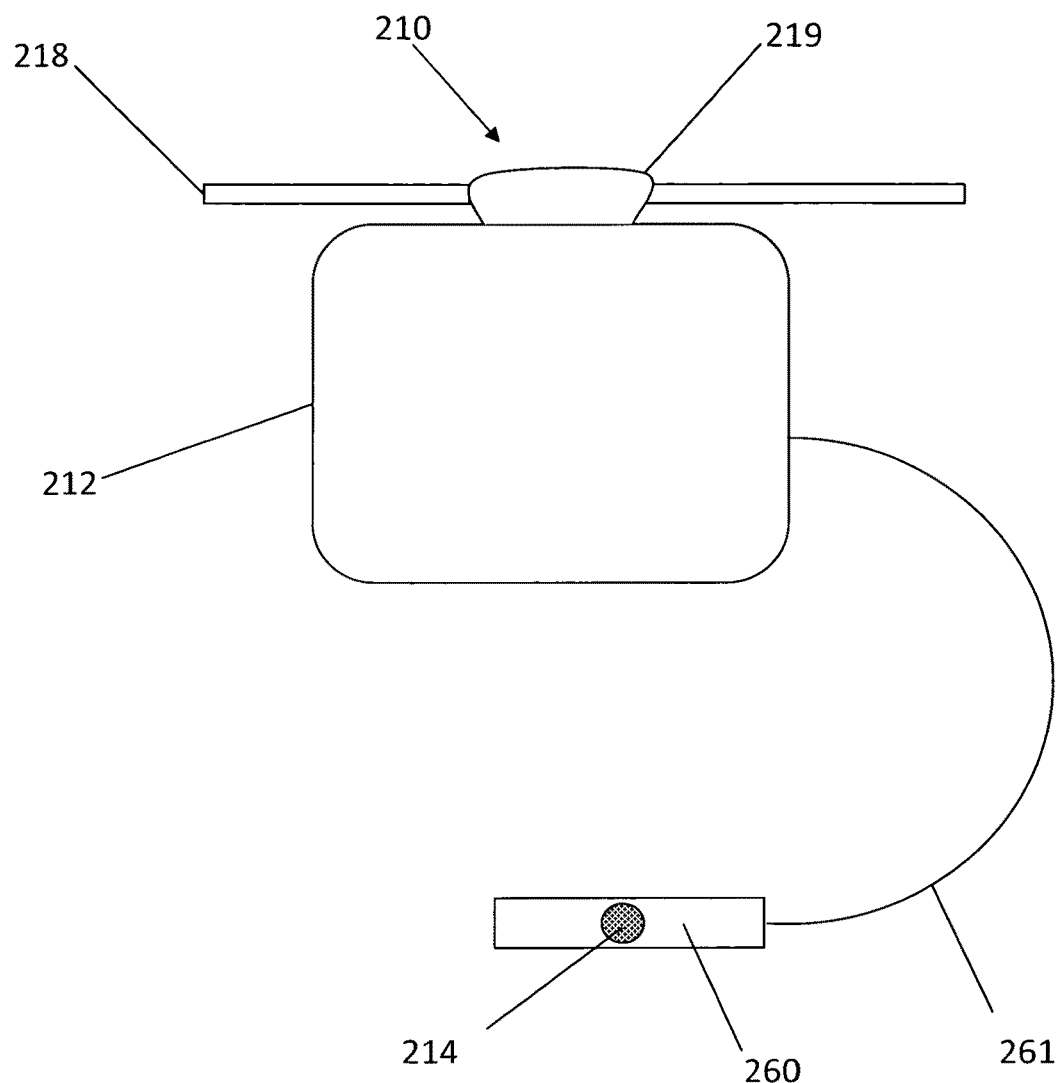
FIGS. 7A and 7B are schematic diagrams of another embodiment of the device.
Figure 7B:
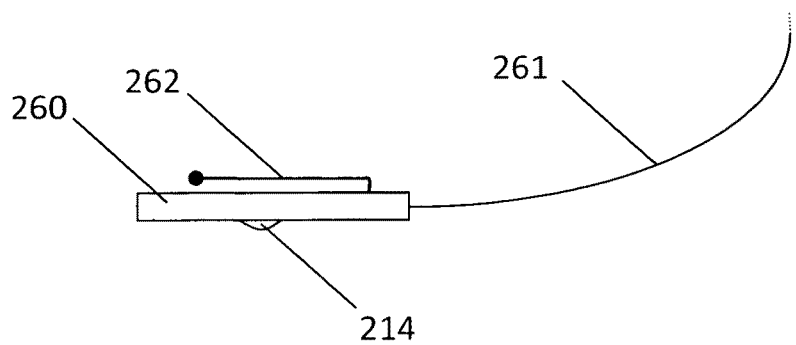

FIG. 7A depicts schematically an alternate embodiment of the designed to be hidden under a shirt collar, for instance under a turtle-neck shirt or a shirt and tie combination. In this embodiment, pendant 210 comprises a housing 212, essentially as shown in FIGS. 6A-6D with a microphone, an accelerometer and/or a vibrator (for example, not shown) contained within the housing 212. The video camera is contained within a second housing 260 connected to pendant 212 by a video cable 261. A lens 214 of the video camera is depicted. FIG. 7B is a side view of the secondary housing 260 of FIG. 7A, showing the lens 214 and cable 261. A clip 262 is provided to facilitate affixing secondary housing 260 to a tie, shirt collar, shirt pocket, etc. As would be evident, it is most desirable to place the secondary housing 260 close to the housing 212 to achieve a good field of view and sufficient height to obtain a useful video record. The housing 212 and secondary housing 260 may comprise one or more aesthetic features. Cable 261 typically includes one or more data transfer wires/cables and one or more power supply wires/cables. Other shapes or designs may be used for the housing or secondary housing. For example, in one embodiment, the secondary housing is in the shape of a button or a pin, with suitable fasteners for affixing the device to an individual's clothing (not shown).

The purpose of the aesthetic features (or decorations) is for the human subjects to have a normal appearance in their daily lives. It is assumed that, with these decorations, subjects will be more willing to accept these devices and the data obtained will be more reliable and more accurately represent the true activities of the subjects. In certain embodiments, such as the embodiment shown in FIG. 4, the cables from the electronic pendant join into a single cable at the back of the neck. In certain embodiments, the electronic pendant may connect under the clothes to a cell phone (smart phone) or a personal electronic device on a waist belt using a suitable plug connector. This cable can send battery power from the cell phone to the device, removing the need for a power supply on the device, such as depicted in FIG. 4, and the multimedia signals acquired by the device to the cell phone. Power can be supplied to the pendant by any means, such as by batteries either incorporated into the pendant, attached to the pendant or otherwise feeding the pendant. In any embodiment, the device optionally comprises a switch or button for temporarily shutting off one or more functions of the device, such as video recording. It may be preferable that the on/off switch does not turn off the microphone and/or accelerometer, to permit the user to recall eating events or respiratory events without video data. The device may further comprise a vibrator, which is turned on periodically (e.g., every 5 minutes) when the one or more functions are turned off and/or malfunctioning (e.g., low battery, blocked lens, etc.) to remind the subject to turn the device on again or to seek service of the device. The on/off switch or button may be located at any suitable position in the device, such as a side of the pendant.

Figure 8:
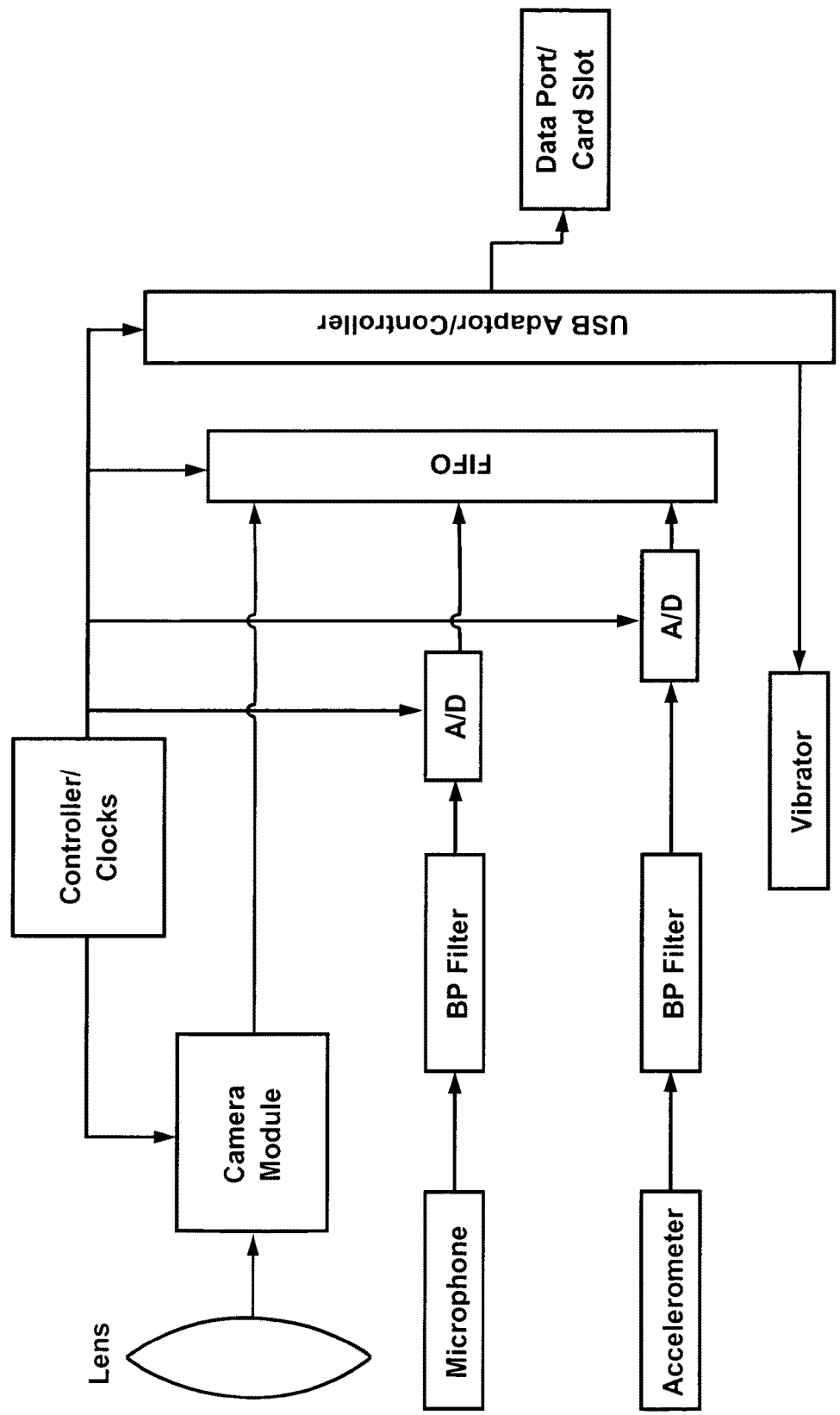
FIG. 8 is a block diagram showing one embodiment of an electrical circuit of the device.

According to one embodiment, while the physiological sensors of the apparatus acquire data continuously, the camera may operate in four different modes, pre-set by the user or clinician according to the particular needs. In the first mode, the camera is on all the time. In the second mode, the camera is turned on only when an eating or drinking event is detected by the swallowing sensor. The third mode turns on the camera when the respiratory signal demonstrates a stronger amplitude and higher frequency above certain threshold levels, indicating an increased physical activity. The last mode is a combination of the second and the third modes. A block diagram of the electronic circuit for the sensor unit is shown in FIG. 8, discussed in further detail below.

Choice of Device Location: Although the device containing the microphone and/or accelerometer, and optionally the video camera may be located in a variety of places on a subject, a preferred location is the jugular notch. There are three reasons to choose the jugular notch as the location of the electronic device: 1) the jugular notch is located at the intersection of three bones—left and right clavicles (collar bones) and the sternum—which makes it the only location on the neck with a natural depression or "seat" within which the electronic pendant can be securely placed; 2) it is found in a strategic location where signals produced by esophageal peristalsis and air flow through the trachea can easily be detected; and 3) its location in the neck is ideal for the simultaneous acquisition of both video and physiological (respiratory and swallowing) data. Placement of the device at any point above the jugular notch would mean a reduced visual field for the video camera due to obstruction from the chin. On the other hand, at any point below the notch, the quality of the recorded respiratory and swallowing signals will be affected because of attenuation through multiple boundaries of thick bone (sternum) and soft-tissues. In embodiments where the video camera is not located within the housing placed, e.g. at the jugular notch, it is preferable to affix the video camera at a location near the jugular notch to provide a satisfactory field of view for the intended purposes of the device.

Device Design: Optimally, the device is as small as reasonably possible. In one embodiment, using current technology, the electronic pendant may be the size of a US quarter (about one inch maximum in any linear dimension). The future size of the device is likely to be significantly smaller, e.g., resembling a real medium-sized pendant, if larger-scale integrated circuits are utilized in later designs. The pendant may include a small, (preferably hidden) button on the side of the device (not drawn) which allows the user to switch on or off the camera. The back side of the device is shown in the middle panel.

To adhere the pendant to a subject's skin, in order to adequately couple the device to the skin, the pendant, on a proximal side to the subject comprises a medically acceptable adhesive, such as a ring of adhesive plastic film for affixing to the skin. Any other suitable means for attaching/coupling the device to skin may be employed. The adhesive is preferably a disposable film with adhesive on both sides, which can be replaced once a day. For example, one side of the film is affixed to the device with a low-strength adhesive and the other side of the film has adhesive foams which affix the device to the skin with a lower-strength adhesive so that when the device is removed from the skin of a subject, the adhesive remains with the device and not on the subject's skin. The adhesive to be utilized may be similar to adhesives used for electrodes or iontophoretic devices, such as those used for ECG electrode pads. The adhesive should not be irritating, and is preferably hypoallergenic such that it will not make the skin uncomfortable in normal cases. Considering that the system may be used during vigorous exercise, which induces sweating, improved comfort may be achieved by using four adhesive foam islands (middle panel). The spaces between these islands provide passages for moisture to escape. The disposable adhesive pads may be arranged with single release sheets on both sides to facilitate proper arrangement of the adhesive by first, removal of the release sheet on the device side of the adhesive, adhering the adhesive, and then removing the release sheet from a skin side of the adhesive prior to placement on a subject's skin. The central part of the device may protrude out slightly, almost to the same height as the adhesive in order to facilitate good skin contact for data acquisition from the neck region. This protruding section has two important functions: 1) it allows the adhesive film ring or adhesive pads to be positioned accurately on the back of the device, and 2) it improves the acoustic and mechanical coupling to the skin for the piezoelectric microphone, accelerometer, and/or vibrator inside the device.

Electronic Design: A block diagram illustrating an embodiment of an electronic circuit within the electronic pendant device is shown in FIG. 8. A command/clock generation unit manages data acquisition tasks and produces control signals to other function blocks. For each analog channel, a band-selective filter may be utilized to eliminate certain primary frequency components of human speech. The purpose of this filtering is to prevent the possible abuse of the system in that the physiological data intended for computer analysis could be instead listened to as audio signals. In addition the filter will not significantly affect the swallowing and respiratory signals because the spectral characteristics of these signals are quite different from those of speech, as we found previously. The filter also has the secondary function of anti-aliasing. The digitized data streams from the camera control module, microphone, and accelerometer are fed into a first in-first-out (FIFO) data buffer (memory). Within this buffer, the data are temporally stored in blocks of fixed sizes.

These blocks then can be delivered to a cell phone or other communication device. For example, the blocks can be fetched sequentially by a USB adaptation circuit according to (e.g.) the USB 2.0 standard and delivered to the cell phone through a USB connector as is often found in smart phones. Within the cell phone, the data can be received and managed by a driver for further processing, including encryption and storage. The driver may be implemented by software and/or hardware. In one non-limiting embodiment, the USB adaptation circuit also receives both power and control signals from the cell phone through the USB connection.

A vibrator may be utilized in a portion of the device affixed to a subject's skin. The vibrator may be utilized to deliver simple messages. For example, when the camera is temporarily turned off, the vibrator can remind the wearer to turn it back on periodically (e.g., every 5 minutes).

Camera Control Module: The camera control module may be any useful module comprising, for example, an imaging sensor, a lens, a video control/DSP chip and any other useful components for generating a useful video signal. In order to facilitate the design of the electronic device, any of the large variety of commercial camera control modules may be used in the device, rather than assembling individual components. This module can be purchased from any number of vendors. Although the designs from different vendors are different, this module usually consists of a CCD imaging sensor, a lens, a multifunctional video control/DSP chip, and a set of discrete components (e.g., capacitor, resistors, and connectors). While the video control component on the chip performs a number of image acquisition tasks, the DSP component on the same chip implements data processing algorithms, such as noise reduction and simple forms of data compression and encryption. The digital output from the video control/DSP chip may be in either a parallel or a serial form, depending on the particular chip design and the input configuration in the next data processing or interface stage.

In one example, the video camera control module is manufactured by Sanyo Electric Co., Ltd., Tokyo, Japan (part No. IGT99267J-ST). The size of the module is less than about a ½ inch in its longest axis. Its size is adequately small for the devices described herein. The lens is an auto-focus camera lens that can be selected for its focal length. Choice of focal length represents a design element and is optional. A shorter focal length is helpful in terms of privacy protection, as only images within a certain proximity of the camera and the individual will be seen clearly. Beyond this focal distance, images would appear more blurred and perhaps indistinguishable, which would be desirable, for instance, with respect to preventing individuals from being identified with whom the subject volunteer comes into contact. The video camera control module also comprises a video control/DSP chip, a number of passive components, a printed circuit board (PCB), and a flexible wire strip including a connector for data and power transfer. This particular module can record 354× 288 color video (a resolution comparable to that of the VHS video tape) at 15 frames per second with a peak power consumption of 45 mW. Besides this device, newer commercial chips (e.g., part number OV6130-C00A, available from OmniVision, Sunnyvale, Calif.) with comparable resolution exist, but are smaller in size and demonstrate lower power consumption (<20 mW at 60 fps). Higher-end chips supporting much higher resolution (e.g., DVD resolution or higher) and frame rates (≥30 fps) also exist that are equipped with sophisticated imaging control and programming functions. However, these are achieved at the expense of higher power consumption. In configuring the systems described herein, factors such as the total power consumption of the device (which preferably is less than 50 mW (on average) for a one-day (12-18 hours) operation), video quality, complexity in circuit design, and the available space will have to be considered. At such low-level power consumption, the heat generated by the device should be insensible.

Respiration and Swallow Detection: The acquisition of respiratory and swallowing signals is important for monitoring a subject's activity and food intake. It has also been shown that there are strong correlations between the respiratory waveforms and certain physiological parameters, such as the respiratory rate, air flow volume, and $CO_2$ production. The swallowing signal is an ideal indicator of possible food/drink intake. In addition, these signals have been well-studied in the literature which has indicated the feasibility of their acquisition at the throat location using microphones and accelerometers.

Microphone: Although the microphone and accelerometer are both responsive to swallowing and respiratory signals, a microphone is more sensitive to acoustic vibrations, while the accelerometer is responsive to movement dynamics. The key to a reliable microphone recording is to reduce the acoustic impedance along the signal path. A number of acoustic sensors, such as hydrophones, free field microphones (e.g., from B&K (Brüel and Kjær)), piezoelectric microphones, and capacitive microphones for different biomedical applications may prove useful for acquisition of respiratory and swallowing signals. It may be preferably to use a piezoelectric crystal based sensor because of its high sensitivity and small size. In circuit design, this sensor can be affixed securely (coupled) to an inner surface of the device to eliminate air in the signal path and provide the best acoustic coupling.

Accelerometer: An accelerometer measures acceleration. Most accelerometers can also measure tilt. The accelerometer was originally a large device, but with the continued advances in the field of micro electromechanical systems (MEMS) technology, they now are available in sizes as small as 2.9×2.9×0.92 mm with 3-axis measurements. The architecture of the MEMS device initially uses a suspended cantilever beam. Recently, a newer architecture has been developed using a heated gas bubble with thermal sensors. When the accelerometer is tilted or accelerated, the location of the gas bubble causes variations in the output. Although most applications of accelerometers are found in the automobile industry, this MEMS device is also useful in biomedical applications, such as in physical activity, swallowing, and respiratory measurements. We have found that the accelerometer data of swallowing are highly reliable, although this device is also responsive to breathing. Although other types of accelerometers may find use in the devices described herein, 3-axis accelerometer may be preferred in most instances for characterization of respiratory and swallowing signals in terms of multi-dimensional dynamics. By combining with the microphone data, the system will provide high pattern recognition ability and measurement accuracy.

Signal Processing: Since respiration, swallowing, and speech signals will all be present in the recording along with biological and environmental noise, we will apply signal processing algorithms to the raw data to extract the breathing and swallowing events from the noise (e.g., speech residual). A variety of algorithms and processes can be used to accomplish this task, for example, as described below.

Peripheral Components: Besides the sensor elements, the device may include peripheral components, such as amplifiers, filters, analog-to-digital converters (A/D converters), clocks, controllers, memory/buffers, and data converters as part of its overall design. The sensor units and the peripherals are integrated into a working system. The microelectronics industry has provided vast resources of integrated circuits of these components. These components can be studied and compared for their suitability for use in the devices and systems described herein.

The size, weight, structural robustness, and power consumption are the most constraining factors in circuit construction and implementation in the devices described herein. In one embodiment, the electronic components of the device are located on a single chip or PCB-chip combinations. Surface mount technology (SMT) which has recently become very popular in electronic designs also may be employed in the devices described herein. SMT reduces the size of both components and their leads, minimizes mounting-holes, and allows the use of miniature circuit boards. SMT mini-circuits may be produced by automated methods or manually under a microscope.

Data Transfer: The apparatus used to communicate data from the device to a centralized computer for analysis may be any useful device for transmitting data over long distances, typically, but not necessarily over a communications network, such as over telephone, cable, internet, wireless, satellite or cellular networks. In one embodiment, the communication device is a mobile phone, a cellular phone or a smart phone. For purposes herein smart phones, mobile phones, cell (cellular) phones, satellite phones, cell or satellite modems or other data transfer devices that utilize the data transfer capacities of wireless, including partially wireless, telephone networks, are considered for purposes herein to be mobile data communication devices. It should be understood that reference to cell phones can equally be applicable to other forms of mobile phones or other mobile data communication devices. The cell phone or other mobile data communication device can be hardware-modified to accomplish the tasks related to communication of data to and from the device or supplying power to the device. That said, the mobile communication device need not be hardware-modified. Instead, hardware-related drivers and software to support data processing, storage, and transmission functions can be installed on a typical mobile communication device, such as a smart phone. In one embodiment, the mobile data communication device is a cell phone or smart phone, which is, in fact, a miniature, multi-functional handheld computing device. Of note, there recently has been a clear trend of unifying the mobile phone with other functional components, including PDA, music player, digital camera, digital camcorder, video player/recorder, GPS device, personal information manager, game player, and/or wireless adaptor into a single device, which is referred to herein as a smart phone, a type of cellular phone. Indeed, the boundaries among all these devices, especially between the smart phones and PDAs, are rapidly blurring. Handheld devices of this type are available from a variety of vendors, such as Palm, Research In Motion (BlackBerry), Motorola, Nokia, Samsung, HP, Sony, and lately, Microsoft and Apple. Even the fully functional laptop PC has become, in many instances, a small personal device. For example, the newly released Sony UX280P runs standard Windows XP with a 40 GB hard drive, 1 GB memory, and an extensive set of wireless data communication/networking options. These devices have provided, and will provide even more choices for the systems described herein.

Once a platform system is selected, software for processing and transporting the multimedia data acquired by the device can be developed on the platform system. A high-performance handheld system, for example one that uses either the Windows XP or CE or Linux operating system, would offer the great flexibility and system resources. The software development will be relatively straightforward on a Windows-based system. However, the unit cost of the system may be higher. On the other hand, using a small cell phone with a less flexible operating system on a manufacturer-specific platform will be more difficult and time-consuming. Advantages are lower unit costs, a slimmer design, and greater convenience. Currently, personal communication and mobile computing are among the fastest growing fields in consumer electronics and new products arrive on the marketplace in an explosive fashion. The choices of the best systems are a matter of design choice using what is available at the time of implementation.

Wireless Option: An alternative embodiment to providing a cable connection between the device and the smart phone or other communication device is to replace the cable with a wireless link, which would provided further convenience in data collection. One embodiment of this design is depicted in FIG. 4, described above. In this design, the pendant includes a wireless communication device, to include transmittal and, optionally, reception capability. In one embodiment, the device is configured as a necklace that comprises a pendant, two necklace portions attached to the pendant, a wireless communication device connected to the two necklace portions, and a power supply. The pendant comprises a video camera, one or both of a microphone and an accelerometer, and, optionally a vibrator and the necklace portions comprise one or more cables comprising wires and/or other data transfer conduits, such as fiber optics, for transferring data and/or power to and from the pendant and wireless communication device. The wireless communication device in this embodiment, or in any embodiment utilizing wireless data transfer methods for transferring data from the monitoring device (e.g., the necklace, pin, etc. comprising the video camera, microphone, accelerometer and/or vibrator) to a smart phone or other long-distance telecommunication device, is any device useful in wirelessly communicating data to and from the monitoring device according to any useful communication protocol, for example Bluetooth, ZigBee, UWB (ultra wideband) or the IEEE 802.11 standard(s). These wireless options are now widely supported by many smart phones and personal electronic devices.

Since the design of a device that is not physically connected to the smart phone or other long-distance (e.g., wide area) communication device does not benefit from deriving its power from the batteries of the long-distance communication device, a power supply is included in the device to facilitate extended periods of operation.

Multimedia Data Processing: The data obtained from the device are transferred to a computer where advanced multimedia processing algorithms in the form of an e-chronicle are utilized to provide a powerful abstraction of the lengthy data (see, e.g., R. Jain. "Media vision: multimedia electronic chronicle," *IEEE Multimedia*, July 2003; S. Guven, M. Podlaseck, G. Pingali, "PICASSO: Pervasive Information Chronicling, Access, Search, and Sharing for Organizations," *Pervasive Computing and Communications,* 2005. *PerCom* 2005. *Third IEEE International Conference,* 2005, 341-350; and P. Viola, M. Jones, Robust Real-Time Face Detection, International Journal of Computer Vision 57(2), 137-154, 2004). The events related to food intake and physical activity are extracted and summarized from both the physiological and video data, and the images of people in the video are blurred for privacy protection. The current multimedia technology can blur approximately 95% of such images (P. Viola, M. Jones, Robust Real-Time Face Detection, International Journal of Computer Vision 57(2), 137-154, 2004). All data processing is performed automatically except that human assistance is required to recognize individual food items and certain physical events using a convenient user interface provided by the system. Both the caloric intake and the energy expenditure are estimated computationally using mathematic models and pre-compiled information (e.g., calories of food items in unit volume) stored in a database.

The human-computer interface is described as follows. After automatic event extraction and privacy screening by the computer, all computer-recognized events related to food intake and physical activity are displayed. A "thumbnail" display, which is similar to that commonly used in displaying pictures, and a "storyboard" display, which surrogates each activity by a representative snapshot in the chronological order, are utilized in the user-interface design along with other human-computer interface techniques, such as specially designed bars, menus, and meters. Once the food items and physical activities are identified and entered into the computer by voice announcement or menu selection, further automatic processing is performed again to provide a comprehensive report in the textual, graphical, and tabular forms. For example, daily food intake is summarized in terms of specific meals and snacks, nutrients, products consumed, and caloric contents, and the energy expenditure from different forms of physical activity is plotted as graphs in a desirable resolution based on both multimedia data analysis and user-entered information.

The amount of human involvement in data processing is dependent on the level of sophistication in multimedia processing and user-interface design. At the present state of the multimedia technology, the workload to process a 24-hour food intake dataset is estimated to be approximately five minutes. Physical activity processing may require twice the time. As the multimedia technology is refined, the amount of human involvement in data processing will be reduced significantly and eventually eliminated.

Electronic Chronicle Data Management System: Algorithms and software modules may be developed for: 1) automatic dietary and physical activity recognition from recorded video data, 2) data management and organization, and 3) user interfaces in the graphical, thumbnail, and storyboard forms for rapid data analysis in obesity research and clinical study.

Data Processing for Automatic Activity Recognition: The data acquired by the electronic pendant can be stored on a flash disk and/or transferred (via a card reader or wireless transmission) to a secure computer in a laboratory or clinic where they can be studied. In theory, recorded data can be scanned manually; however, this would be tedious and labor-expensive. Algorithms can be developed to provide useful abstractions of the lengthy data to facilitate examination by a human observer.

Diet Recognition: In the systems described herein, the video recording containing eating/drinking activity can be recognized from the swallowing signal rather than the video itself. This is because: 1) automatic reorganization of food intake by video processing requires complex procedures and is subject to constraints such as occlusion (J. Gao, R. T. Collins, A. G. Hauptmann and H. D. Wactlar, "Articulated Motion Modeling for Activity Analysis," *CIVR* '04, *ANM* '04, Dublin City, Ireland, 2004; J. Gao, A. G. Hauptmann and H. D. Wactlar, "Combining Motion Segmentation with Tracking for Activity Analysis Dining," *FGR* '04, Seoul, Korea, 2004:

699-704; and J. Gao, A. G. Hauptmann1, A. Bharucha, and H. D. Wactlar, "Dining Activity Analysis Using a Hidden Markov Model," *ICPR '04*, Cambridge, United Kingdom, 2004), and 2) feeding monitoring by the swallowing sensor will be more continuous than the camera monitoring since the camera will have to be turned off in certain locations because of privacy concerns. The success of this indirect approach depends on the extraction of the swallowing events from the recorded physiological data, along with the extraction of respiratory events. It must be pointed out that swallowing data recorded at the jugular notch would reflect both involuntary as well as voluntary (eating/drinking) esophageal activity. It will be necessary to be able to distinguish between these two swallowing events in order to identify the specific points in time when food consumption is occurring. This problem can be approached through an in depth physiological study and mathematical modeling. There have been reports describing the frequencies and variations of these two types of swallowing (J. D. Rudney, Z. Ji, C. J. Larson, "The prediction of saliva swallowing frequency in humans from estimates of salivary flow rate and the volume of saliva swallowed," *Archives of Oral Biology,* 1995, 40(6): 507-512 and K. M. Hiiemae, A. W. Crompton, "Mastication, food transport and swallowing," *Functional Vertebrate Morphology,* 1985). A basis to construct a probabilistic model and an optimal classifier can be constructed based on the frequencies and intensities of the detected events. The classification results should be accurate because of the wide differences in frequency and intensity between these two events.

Food/Drink Recognition: Once the food/drink swallowing events are detected, the synchronously recorded video segments containing dietary information can be located which can then be labeled. Although further automatic recognition of foodstuffs is possible, the wide variety of human foods and drinks makes it difficult to produce accurate results. Therefore, initially, food/drink recognition can be performed manually. Fortunately, according to a survey by U.S. Department of Labor, the average American adult spends only one hour and twenty minutes eating and drinking per day. Within this time, only a small fraction needs to be examined visually for dietary assessment. Using the automatically labeled data and a sophisticated e-chronicle interface (detailed below), we expect to document an average-day food intake by approximately five minutes per patient, assuming a typical American diet.

Quantitative Food/Drink Measurement: Measuring the size of a dietary item is a critical problem in nutrition research. The current methods use rough estimates depending on the memory of the respondent and container/package size. Here, this problem can be solved computationally and objectively.

Automation of Measurement Process: In general, it is not possible to measure the volume of a three-dimensional object from a picture containing only a single view. However, in the case of food and drink, this restriction can often be relaxed. Most food items (e.g., pizza, pie, bread, and potato) have certain symmetries and known shapes. Even irregularly shaped food (e.g., mashed potatoes or scrambled eggs) is usually served using a symmetric container; the same is true for liquid foods and drinks. Therefore, allowing for certain errors, which could be an order of magnitude smaller than the current method, volume measurement in a single projection or a small number of projections (in the case of a moving object) should be possible in most instances.

The image processing tools can be highly automatic, requiring minimal human provided inputs. The nutritionist first selects a good view from the video. Then he/she needs only to point to the food item on the screen and, within a certain time, speak to the computer the item name (such as "a glass of milk"). The computer will listen within this time and, if understood, respond immediately with the segmented food item and measured volume, weight, and/or caloric content. The results, along with the time, location (based on the GPS data), and other information of interest, can become part of the data managed by the e-chronicle. In cases of difficulty in food measurement, an electronic ruler (such as the one described above) can be used to assist the process, which only requires the nutritionist to click several locations on the food item. (database may include commercial items, such as a "small bag of Cheetos" or a "Big Mac").

Speech recognition for such small-vocabulary applications is now highly accurate (The Microsoft Speech SDK 5.1, available from Microsoft Download Center). Since numerous commercial or public-domain software packages are available, such as the one provided by Microsoft, this software need not be developed.

Computational Methods: Correct Image segregation is important in order to implement the automatic procedure just described. Due to the wide variety of foods, the best segmentation tool must be food-specific, to be selected from a set of segmentation tools. A knowledge-based approach would be useful in this task. A toolset can be constructed, each tool can be associated with the most applicable food items, and the results in a tabular form in our e-chronicle system. During on-line operation, after the food name/container/unit information (e.g., "a bowl of cereal" or "a slice of pizza") is heard and understood by the computer, a segmentation manager can perform an immediate table look-up for the best tool. This tool can then be employed to segment the food item and calculate its area (in number of pixels). Next, the area can be converted to the volume in $cm^3$ based on multiple sources of information, including the input about the container/unit, calculated geometric shape parameters (e.g., the diameter and height of the milk in a glass), estimated/computed set of viewing distances and angles, and pre-stored formulas relating shape parameters and volume. Finally, the volume can be further converted to weight and calories, simply by using the USDA National database (cited elsewhere).

Segmentation Algorithms: The image segmentation toolset may include for example and without limitation: 1) common thresholding tools with respect to gray scales and/or HSU color values (N. Otsu, "A threshold selection method from grey-level histograms," *IEEE Transansactions on Systems, Man, and Cybernetics,* 1979, 1:62-66; S. Sural, G. Qian, S. Pramanik, "Segmentation and histogram generation using the HSV Color space for content based image retrieval," *IEEE Int. Conf. on Image Processing,* 2002; N. Herodotou, K. N. Plataniotis, A. N. Venetsanopoulos, "A color segmentation scheme for object-based video coding," *IEEE symposium on Advances in Digital Filtering and Signal Processing,* 1998, 25-30; and S. Vitabile, G. Pollaccia, G. Pilato, E. Sorbello, "Road signs recognition using a dynamic pixel aggregation technique in the HSV color space," *Int. Conf. on Image Analysis and Processing,* 2001, 572-577); 2) region growing tools based on split-and-merge (R. C. Gonzalez and R. E. Woods, *Digital Image processing*, Addison-Wesley Publishing Company, 1993) or watershed segmentation (L. Vincent and P. Soille, "Watershed in digital spaces: an efficient algorithm based on immersion simulation," *IEEE Trans. on Pattern Analysis and Machine Intelligence,* 1991, 13(6):583-589); 3) edge and contour tools based on the Hough transform (P. V. C. Hough, "Methods and means for recognizing complex patterns," U.S. Pat. No. 3,069,654, 1962) and active contour "snake" (M. Kass, A. Witkin, and D. Terzopoulos, "Snakes:

active contour models," *Int. J. of Computer Vision*, 1988, 1(4):321-331 and T. Meier and K. N. Ngan, "Video segmentation for content based coding," *IEEE Trans. on Circuits and Systems for Video Technology*, 1999, 9(8): 1190-1203); and 4) texture tools based on co-concurrence matrix (R. C. Gonzalez and R. E. Woods, *Digital Image processing*, Addison-Wesley Publishing Company, 1993), Gabor wavelet filter (B. S. Manjunath and W. Y. Ma, "Texture features for browsing and retrieval of image data," *IEEE Trans. on Pattern Analysis and Machine Intelligence*, 1996, 8(18):837-842), and edge-flow vectors (W. Y. Ma and B. S. Manjunath, "EdgeFlow: a technique for boundary detection and image segmentation," *IEEE Trans. on Image Processing*, 2000, 9(8): 1375-1388). In certain cases, a moving food item (e.g., a piece of butter being placed on bread) needs to be segmented. Tools can be included based on clustering in the motion parameter space (J. Y. A. Wand and E. H. Adelson, "Representing moving images with layers," *IEEE Trans. on Image Processing*, 1994, 3(5): 625-638) and spatio-temporal measures (F. Moscheni, S. Bhattacharjee, and M. Kunt, "Spatialtemporal Segmentation based on Region Merging," *IEEE Trans. on Pattern Analysis and Machine Intelligence*, 1998, 20(9): 897-915) in our toolset. In addition, pre- and post-processing tools, such as bilateral Gaussian filter (C. Tomasi and R. Manduchi, "Bilateral Filtering for Gray and Color Images," *Proc. of the 1998 IEEE International Conference on Computer Vision*, Bombay, India, 1998 and M. Elad, "On the Origin of the Bilateral Filter and Ways to Improve I," *IEEE Trans. On Image Processing*, 11(10), October 2002) and morphological filter (L. Vincent, "Morphological grayscale reconstruction in image analysis: applications and efficient algorithms," *IEEE Trans. on Image Processing*, 1993, 2(2): 176-201) can be constructed to improve segmentation results in noisy images.

Physical Activity Assessment: Three sources of information may be used to assess the level of physical activity during the recording day. Specifically, define a sliding window in the time direction can be defined. Within each time step, we can compute: 1) the number of the respiratory events; 2) the body acceleration intensity by integrating the squared signals obtained from the accelerometer after removing biological events; and 3) displacement measures calculated by the magnitude of body swings and slope (elevation) changes using the methods above. Clearly, these three variables are related to the physical activity and energy expenditure (EE). However, restrictive assumptions should be imposed to derive the explicit relationship between these variables and the EE function. A simple, but potentially effective, approach to obtain an estimate of the EE function may be as follows. To calibrate the device, measurements can be compared to those obtained using a commercial device (e.g., SenseWear by Bodymedia, Pittsburgh Pa.) for physical activity measurement—Assuming that the commercial device is accurate according to the manufacturer and existing reports (www.bodymedia.com/products/bodymedia.jsp and M. L. Irwin, B. E. Ainsworth and J. M. Conway, "Estimation of energy expenditure from physical activity measures: determinants of accuracy," *Obesity Research*, 2001, 9:517-525). Using the EE function obtained by the commercial device as a template, we can fit this function at each point using the three variables (mentioned above) obtained from our device. Least-square fitting algorithms (W. H. Press, B. P. Flannery, S. A. Teukolsky, W. T. Vetterling, *Numerical Recipes in C: The Art of Scientific Computing*, Cambridge University Press, 2nd Edition, 1992) may be utilized. It is believed that least-square fitting is optimal in this case because achieving the minimum of the overall error is most desirable. The performance of the system described herein can be evaluated quantitatively by the residual error of fitting.

A reasonable fitting is expected because our variables change substantially from the baseline as the physical activity intensifies. Physiologically, the respiratory signal is correlated with the gas exchange process. This correlation may be moderate without accurate instruments. In addition, the physical activity information provided by the accelerometer and video measure is limited, and these measures may not adequately reflect the resting energy expenditure (REE). These factors will contribute to system errors. However, this type of error is expected to exist in other commercial devices, such as the SenseWare device, which provides the EE function by the outputs of sensors embedded in an armband. This single-location configuration in the body may also limit its ability to observe all EE-related factors. However, some reports have stated that the measured EE function, by this device, is accurate (www.bodymedia.com/products/bodymediajsp and M. L. Irwin, B. E. Ainsworth and J. M. Conway, "Estimation of energy expenditure from physical activity measures: determinants of accuracy," *Obesity Research*, 2001, 9:517-525), despite the described potential limitations.

Errors in determining physiological parameters can be corrected. The sources of error can be analyzed from both physiological and engineering aspects. For example, if the error is mainly caused by the low specificity of the overall motion vector energy calculation, more sophisticated algorithms may be used to extract more activity-correlated variables and filter-out false "motion", such as that due to the moving scene on a TV screen. It also seems to be necessary to include appropriate delays into the function fitting process since there is a latency between the physical activity and respiratory response. It may be desirable to add new sensors to the system, for instance, an additional accelerometer and/or microphone at a different location, but in communication with the main device and/or the associated communication links, a measuring thermometer or other physiological or environmental sensors that are or may prove to be useful in determining energy expenditure. Even in the case where the EE function fitting is unsuccessful, a physical activity index function (e.g. with a value range between 0 and 1) can be constructed which can be used as a barometer to assist the manual scan of long-term video data. Besides the preferred EE or index functions, summarizing data can be provided for periods of resting times (based on the tilt information provided, for example, by the accelerometer), step counting/distance traveled/slope changing (for example, based on the methods described above), and respiration rate (for example by the methods described below).

Extraction of Respiratory and Swallowing Signals: The performance of the systems and methods described herein are dependent on detected respiratory and swallowing signals. Accurate extraction of these signals is not straightforward since both signals appear in the microphone and accelerometer channels, and there is considerable noise due to speech and environmental sound in both channels. Our system must be able to identify and separate them. Advanced signal processing techniques can be applied to accomplish these tasks. There exists a large body of literature documenting the physiology and the acoustic features of the respiratory and swallowing signals (A. L. Perlman, S. L. Ettema, J. Barkmeier, "Respiratory and acoustic signals associated with bolus passage during swallowing," *Dysphagia*, 2000, 15:89 C94; H. Firmin, S. Reilly, A. Fourcin, "Non-invasive monitoring of reflexive swallowing," *Speech Hearing and Language: work in progress*, 1997, 10: 171-184 and M. S. Klahn, A. L. Perlman, "Temporal and durational patterns associating respiration and swallowing," *Dysphagia*, 14:131-138). These features can be utilized in our algorithm design. Specifically, we can use a set of overlapped windows to scan the recorded data in both the microphone and accelerometer channels. Within each window, we can implement a number of feature extraction algorithms. The features extracted can be collected to form a vector (pattern vector). This vector can be appropriately normalized and fed to a pre-trained artificial neural network. This network can make decisions whether the data within the window contain an event of interest and, if yes, whether it is a respiratory/swallowing event which can be kept for e-chronicle applications, or a speech signal which can be suppressed to protect the privacy of the speaker. Choose signal processing algorithms can be selected to extract features that yield the maximum differences among the swallowing signal, respiratory signal, and biological/environmental noise (including speech). These differences may allow us to identify the status of each input within the hyperspace spanned by the patter vectors. The candidate signal features to be computed can include: the energy value, area of coverage, shape/axial/symmetry measures, instantaneous frequency, fractal dimensions, spectral tail, and the statistical features extracted in the wavelet and time-frequency domains. The artificial neural network to be evaluated may be a conventional three layer feed-forward back propagation network with standard designs training algorithms (Mohamad H. Hassoun, *Fundamentals of Artificial Neural Networks*, The MIT Press, 1995). Other neural network types, such as the radial basis function network, Bayesian network, and recurrent network, and more sophisticated training algorithms can also be compared for performance comparison. In each case, the results of any artificial neural network can be evaluated based on the correct, undetected, and falsely classified respiratory and swallowing events.

Data Organization: Organization of the multimedia data is an important system component. In a general-purpose e-chronicle system, data from various sources are collected and managed. Thus, a large scale database (called a chronicle repository) is required (G. Pingali, R. Jain, "electronic chronicles: empowering individuals, groups, and organizations," *Multimedia and Expo*, 2005. *ICME* 2005, 2005, 1540-1544). Here the sources of multimedia data are, according to one embodiment, limited to video, respiratory, and swallowing signals. This permits substantial simplification of the data management task. The video data can be indexed and summarized as described previously and a metadata set containing text, lists, thumbnails, and description parameters can be formed. These metadata can be stored, for example, separately from the raw data on a different, but closely linked, RAID server. All servers can be made accessible by a security-protected network. Every raw data and metadata item can be marked with time, location (GPS coordinates), and patient/subject identification number for easy organization and manipulation. Standard software development tools such as XML and XSLT can be used to construct the data management system (Tim Bray, Jean Paoli, C. M. Sperberg-McQueen, eds., W3C Recommendation 10 Feb. 1998, www.w3.org/TR/1998/REC-xml-19980210; James Clark (ed.) (1999). XSL Transformations (XSLT), W3C Recommendation, 16 Nov. 1999, www.w3.org/TR/1999/REC-xslt-19991116). Other standard video and image abstraction tools also may be utilized, such as MPEG-7 (MPEG-7 Test & Ealuation Ahg Meeting, Lancaster University, 15-19 Feb. 1999 and J. Hunter, "MPEG-7 Behind the Scenes," *D-Lib Magazine*, 1999, 5(9)) and SMIL (World Wide Web Consortium W3C Synchronized Multimedia Integration Language (SMIL) 1.0 Specification). These standard tools are compatible to the digital video library database that has already been developed by our group (R. Yan, J. Zhang, J. Yang, and A. Hauptmann, "A discriminative learning framework with pairwise constraints for video object classification," *IEEE Transaction on Pattern Analysis and Machine Intelligence (PAMI)*, 2006, 28(4):578-593). These standard tools and the available platform will not only facilitate development, but also allow future expansion of the e-chronicle technology across research and clinical groups and platforms.

User Interface: The e-chronicle system may provide three types of user interfaces allowing researchers and health care professionals to examine data. Optimally, the user is provided with the maximum, yet uncluttered information to address his/her needs while minimizing the time required for data examination, report generation, and extraction of both intra- and inter-subject information. These interfaces can also be designed in an easy-to-learn, user-friendly fashion.

Timeline-Based Interface: This form of interface provides several traces of plots with the same x-axis, representing the time in hours. Each trace represents a variable, such as the swallowing activity, EE function or physical activity level, walking, and respiration rate. Unlike the ordinary plots, the time axis at each trace can be activated by a mouse-click to index the location of related data segment. For example, when a lunch meal on a particular day is examined, the viewer can simply click the swallowing trace at the time axis where a large cluster of swallowing activity appears around noon of that day. As a result, another interface, such as the storyboard interface (described below), will appear summarizing this lunch meal.

Thumbnail Interface: Thumbnails have been commonly used in computers to display pictures. A recent study has shown (M. G. Christel, "Windowing time in digital libraries," *Proc. ACM/IEEE-CS Joint Conf. on Digital Libraries*, 2006, 190-191) that this form of interface is also very useful in representing multiple sets of videos on a screen to search for the desired information. For example, if the walking pattern after dinner among a group of obese subjects is of the interest to the study, a time range (e.g., between 6 p.m. and 8 p.m.) and "walk" is selected in the timeline based interface, the representative pictures in multiple sets of video data containing the walking information will be displayed with a color bar indicating the relevance of the query item. The viewer can then selectively replay the video segments or perform data analysis.

Storyboard Interface: The storyboard interface is an abstract form, or a surrogate, of chronological display of a video segment (M. G. Christel, *Proc. ACM/IEEE-CS Joint Conf. on Digital Libraries*, 2006, 190-191). In other words, it extracts the key frames from the video segment of interest and displays them as a series of thumbnails in the chronological order. If the video segment is very long, multiple layers of storyboard can be utilized. The interface allows viewer to quickly find the point of interest by test-viewing video after clicking a thumbnail.

Privacy Protection: Although the e-chronicle technology is a powerful tool for obesity study and behavior related research in general, it faces a critical problem of possible invasion of privacy. Because of the particular setup of the described system, the bearer of the sensor never appears in the recorded video unless a mirror is utilized. In addition, speech can be both hardware-suppressed and software-screened as described above and thus is not maintained as part of the data. The system design can make speech unintelligible even if it is accidentally recorded. The main problem here is that other people may be accidentally recorded who have not given a consent to appear in the video. The approach to this problem is multifaceted in both enforcing necessary regulations in data acquisition and applying technological solutions.

Focal Range Restriction: In many cases, it may be necessary to compromise the clarity of the video to address privacy protection concerns. Fortunately, for the issue of dietary assessment, the visibility of the video images within a distance of about 1, 1.5, 2, 2.5 or 3 feet from the camera will be sufficient to allow clear observation of foods on the dining table. Other people will rarely be situated in such close proximity to the test subject. Therefore, a camera lens which has a depth of field (DOF) that is less than this distance optionally may be used. The best depth can be determined experimentally. Once this depth is set, the camera lens to be used for the human subject study can be commercially acquired. Numerous manufacturers of miniature lenses are available for either direct purchase or custom-manufacturing of these lenses. Examples of some companies include Largan Digital Co., Ltd, Phoenix, Ariz.; Marshall Electronics, Inc., El Segundo, Calif.; and Kanto Tatsumi Electronics Co., Ltd. Japan.

Figure 9B:
FIG. 9B is a photograph showing the effect of using a camera lens with a limited field of view.
Figure 9C:
FIG. 9C is a photograph showing the effect of using a human image localization and suppression algorithm.
Figure 9A:
FIG. 9A is a photograph of a recorded scene with a high risk of privacy breach.

Human Image Localization and Suppression Algorithms: As stated previously, the e chronicle technology can acquire a wide spectrum of life-style information. The previously described approach, although safe in preventing privacy invasion, may severely limit the value of data if other life-style related obesity research is intended other than dietary assessment. We have previously studied advanced technologies for automatic de-identification (e.g., privacy screening) of video data in compliance with federal regulations (HIPPA) in support of medical research (J. Yang, W. Holtz, W. Yang, and M. T. Vo, "An adaptive multimodal interface for wireless applications," Proceedings of International Symposium on Wearable Computers, 1998; J. Yang, W. Yang, M. Denecke, A. Waibel, "Smart sight: a tourist assistant system," Proceedings of ISWC'99;J. Yang, J. Gao, Y. Zhang, X. Chen, and A. Waibel, "An automatic sign recognition and translation system," Workshop on Perceptive User Interfaces (PUI 2001); J. Yang, X. Chen, W. Kunz, "A PDA-based face recognition system," Proceedings of WACV 2002, 2002, 19-23; and J. Yang, X. Chen, W. Kunz, H. Kundra, "Face as an index: knowing who is who using a PDA," International Journal of Imaging Systems and Technology, 2003, 13(1): 33-41). Fueled by the heightened security demands, there have been numerous algorithms developed based on features such as motion, shape, and flesh color for automatic identification of human images. It has been reported that the effectiveness of the best algorithms can be nearly 95% (P. Viola, M. Jones, "Robust Real-Time Face Detection" International Journal of Computer Vision, 57(2), 137C 154, 2004) These algorithms can be studied, selectively implemented, modified, and compared with our algorithms. The performance of the automatic de-identification system can be evaluated using mock video recordings. FIG. 9 illustrates the effect of our privacy protection solutions for a breakfast scene (left panel as in FIG. 9A) by using a lens of limited depth of view (as in FIG. 9B) and by human image localization and suppression (as in FIG. 9C).

Data Encryption/Decryption: In order to further protect the temporary data before machine-reading for the purpose of de-identification, the data recorded and saved to the smart phone will not be available for observation by any human observer, including researchers and health professionals. These data will be encrypted to safeguard their transportation and/or transmission. While low data-rate acoustic signals may be encrypted using standard encryption algorithms, such as RSA and DES (M-Y. Rhee, *Internet Security: Cryptographic Principles, Algorithms and Protocols*, Wiley, 2003), the video data must be encoded using more efficient algorithms which do not seriously complicate the computational load. There have been several algorithms developed for this purpose, such as those based on chaotic theory (S. Li, G. Chen, and X. Zheng, "Chaos-based encryption for digital images and videos," in *Multimedia Security Handbook*, B. Furht and D. Kirovski, Eds. CRC Press, LLC, 2004, ch. 4, 133-167, with preprint available at www.hooklee.com/pub.html), visual perception (J. Dittmann and A. Steinmetz, "Enabling technology for the trading of MPEG-encoded video," in *Information Security and Privacy: Second Australasian Conference (ACISP??97) Proc., ser. Lecture Notes in Computer Science*, 1997, 1270: 314-324; Y. Bodo, N. Laurent, and J. L. Dugelay, "A scrambling method based on disturbance of motion vector," in *Proc. 10th ACM Int. Conference on Multimedia*, 2002, 89-90; M. Pazarci and V. Dipc?in, "A MPEG2-transparent scrambling technique," *IEEE Trans. Consumer Electronics*, 2002, 48(2): 345-355; and C. Wang, H. B. Yu, and M. Zheng, "A DCT-based MPEG-2 transparent scrambling algorithm," *IEEE Trans. Consumer Electronics*, 2003, 49(4): 1208-1213), and, more recently, fixed-length codewords (S. Li, G. Chen, A. Cheung, B. Bhargava, K-T. Lo, "On the design of perceptual MPEG-Video encryption algorithms," *Computer Science, abstract cs.MM/0501014 v2* Aug. 31, 2006). These algorithms can be studied, compared, and modified for our application.

Example 2

In this example, we present a novel approach to the study of energy intake and expenditure by using a video-based system. This system ubiquitously acquires free-living data and analyzes these data by using advanced multimedia technology. In these experiments, the study participants wear a video camera attached to the front of their body. As an electronic visual memory, this camera stores essentially all the scenes that these individuals have observed throughout the recording period. This video recording serves two main data acquisition purposes: 1) daily food intakes, and 2) daily physical activities. When compared to the current use of questionnaires, the objectively recorded video avoids most human errors in food intakes and physical exercises.

In order to study the effectiveness of using the multimedia technology to assess energy balance, experiments in both food intake assessment and physical activity analysis were conducted. In the first case, a semi-automatic method to measure foods and drinks from the recorded video data was investigated. In the second case, algorithms to evaluate walking/jogging velocities via motion analysis were developed. As is shown in the following examples, advanced multimedia technology provides a powerful tool for the study of obesity, and this technology promises to be a practical means of performing life style analysis which is essential in the development of effective treatment programs.

Dietary Assessment

In our experiments on dietary assessment, we utilized a compact digital camera (SiPix StyleCam Blink, focal length 6.3 mm, aperture size F3.0) to acquire video data. When focused on objects within three feet of distance, this camera produces video images with varying degrees of sharpness for the foreground and background objects. The background objects are recorded at an acceptable sharpness only when they are located within 4.5 feet from the camera. As this distance or the aperture size increases, the background scene becomes increasingly blurry. This property of the camera is useful to control the depth-of-field in the recorded data. The images of persons who appear in the background can therefore be blurred to a degree where they are no longer recognizable or identifiable. This is useful for dealing with sensitive issues surrounding privacy protection.

Figure 1B:
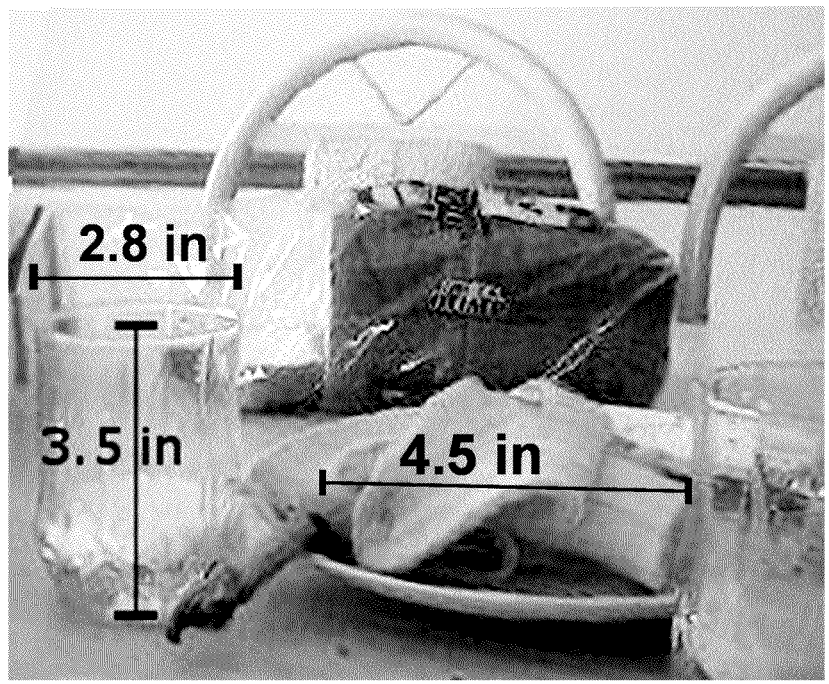
FIG. 1B shows an image of breakfast items with computer assisted measurements.

The camera was attached to the body essentially as shown in FIG. 1. It is connected to a computer via a USB port. The video capture was controlled by a computer, which stores the compressed video data (320×240 pixels at 30 frames per second) on the hard drive. In our experiments, the foods and drinks were placed within an area of 2×2 square feet in front of the study participants. This area was well covered by the camera which has a field of view of approximately 75 degrees. The participants were asked to dine normally during video recording. A snap shot of a dining video is shown in FIG. 1B. During data examination, the nutritionist can clearly identify the types of food/beverage consumed in most cases. The main goal of our study was to assist the nutritionist in determining the volume, weight, and caloric content by using signal processing algorithms.

For the common foodstuffs within a certain culture, people who are familiar with the culture usually have good knowledge about the shape and size of the foods and/or their containers. Therefore, it is usually feasible to estimate the volume of a food object from a single or a small number of two-dimensional projection images. The key problem, however, is to provide accurate length measurements (see those lengths FIG. 1B) in an actual physical unit based on the lengths in terms of pixels.

Figure 10:
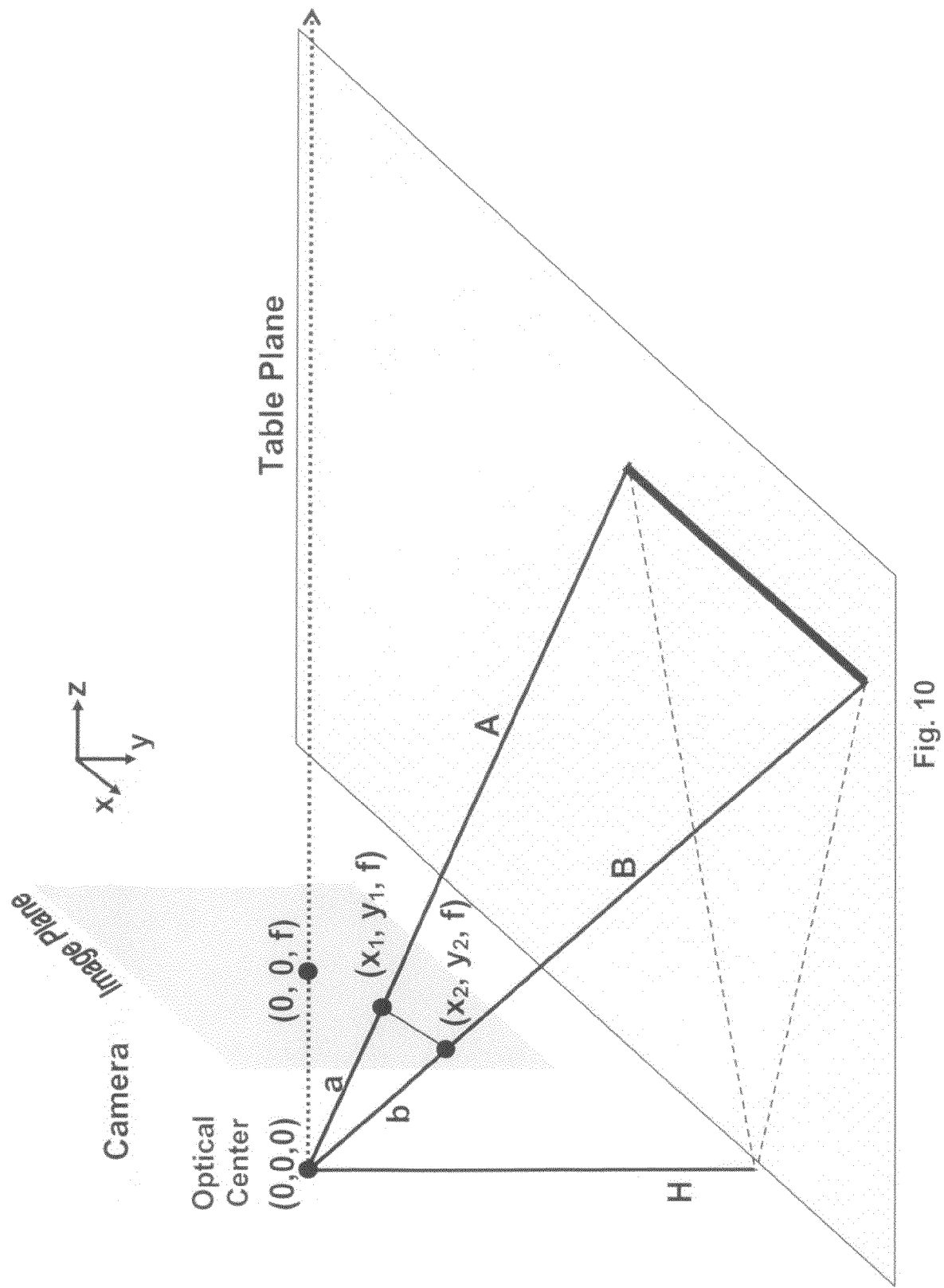
FIG. 10 is an illustration of geometric relationships among the coordinates of the camera optical center, image plane, and food object on the table plane.

In order to derive a conversion formula between the physical length and the pixel length, we must understand the geometric relationships among the parties involved, including the camera optical center, image plane, and food object on the table plane. These relationships are illustrated in FIG. 10. Setting the camera optical center as the origin at (0,0,0), the intersection point of the optical axis and image plane is (0, 0,f). In the image, the two ends of the segment corresponding to the observed object have world coordinates $(x_1,y_1,f)$ and $(x_2,y_2,f)$, and H is the height from the camera to the dining table top. To convert the pixels' coordinates in the image plane to the world coordinates, we write $$x_1 = i_1 \cdot d_x, x_2 = i_2 \cdot d_x, y_1 = j_1 \cdot d_y, y_2 = j_2 \cdot d_y \quad (1)$$

Where $i_1, i_2, j_1, j_2$ are the pixel indices in the image plane. Observing A, B, a, and b as defined in FIG. 10, we have the following relations $$\frac{y_1}{H} = \frac{a}{A}, \frac{y_2}{H} = \frac{b}{B} \quad (2)$$

Based on Equations (1) and (2), we can calculate length L of the observed object by $$L = \frac{H}{j_1 \cdot j_2 \cdot d_y} \sqrt{(i_1 \cdot j_2 - i_2 \cdot j_1)^2 d_x^2 + (j_1 - j_1)^2 f^2} \quad (3)$$

Equation (3) provides an important observation that the variations of H and L are linearly related. In practice, the value of H, which represents the vertical distance between the camera lens and food table, is a major unknown factor. Fortunately, the variation of H is limited since, if the heights of the chair and the table were to vary drastically, it would indicate a very uncomfortable dining experience.

Once L is estimated, we are able to measure the volume of the food in most cases using existing human knowledge. For example, FIG. 1B shows a glass of milk with a height h and a radius r estimated from Equation (3). In this case, the volume of the milk is approximately given by V. This volume can then be utilized to calculate the weight and calories using standard food tables, such as the USDA national database (see, e.g., U.S. Department of Agriculture and Agricultural Research Service, "USDA nutrient database for standard reference, Release 19," available in Nutrient Database Laboratory Home Page, 2006, (www.ars.usda.gov/ba/bhnrc/ndl) and U.S. Department of Agriculture, Agricultural Research Service. 2007. USDA National Nutrient Database for Standard Reference, Release 20. Nutrient Data Laboratory Home Page, (www.ars.usda.gov/ba/bhnrc/ndl)).

Video Assessment of Walking/Jogging

The recorded video provides a rich set of information about a variety of physical activities. These activities represent a critical portion of the energy expenditure closely related to the etiology of obesity. Here, we focus only on the most common forms of these activities: walking and jogging. In our experiments, we utilized a SONY DCR-TRV20 camcorder affixed to the center of the lower neck while performing such activities. Four types of video were acquired: walking on a level ground, walking uphill, walking downhill, and jogging on level ground. We utilized an algorithm to register the walking/jogging steps by analyzing the recorded video frames. We call this algorithm "video pedometry". This algorithm is based on the observation that, during walking/running, the human body swings both vertically and horizontally. The video acquired by the camera reflects this periodic motion. By identifying the period of motion, one can identify the gait frequency and, with additional knowledge of the elapsed time, step size, and body weight, the velocity and the distance of travel as well as the energy expenditure can be estimated.

Since the underlying motion is caused by the periodic movement of the camera, we characterize this movement by shifts in the video content within a series of recorded frames. Numerous methods exist to calculate frame displacements such as those utilized in image registration (see, e.g., J. Wang, and J. Chun "Image registration for an imaging system onboard fast moving military vehicle," Proceedings of the IEEE NAECON 2000, pp. 239-243, 2000 and M. Lee, M. Shen, A. Yoneyama, and C. C. Jay Kuo, "DCT-domain image registration techniques for compressed video," IEEE ISCAS 2005, Vol. 5, pp. 4562-4565, 2005.). Most of these methods, however, are computationally expensive. Considering the tremendous amount of data that may result from the long-term recording, we utilized a simple, but highly robust, method to calculate frame displacements. First, horizontal projections (i.e. summations of the pixel intensities along rows) of two video frames are calculated. These projections represent the "marginal distribution" of the row intensities. To estimate the shifts between two input frames, we calculate the translation of one of the projected intensity vectors that renders the maximum correlation between the two projection vectors. This was done by the following:

Calculating the Cross-Correlation $$R_{i,j}(\tau) = \begin{cases} \frac{1}{N+\tau} \sum_{n=1}^{N+\tau} p_i(n) p_j(n-\tau), & -N < \tau < 0 \\ \frac{1}{N-\tau} \sum_{n=\tau+1}^{N} p_i(n) p_j(n-\tau), & 0 \leq \tau < N \end{cases}$$

where N is the length of horizontal projection vectors for each frame; $\tau$ is the shift between two projection vectors; $p_i$ and $p_j$ are the projections of frames i and j respectively, with i=1, 2, ..., j=1, 2, ... M and M is the number of frames in one video clip.
finding the shift $$\tau^* = \max_{\tau} R_{i,j}(\tau)$$

when i and j are previously fixed.

Figure 11A:
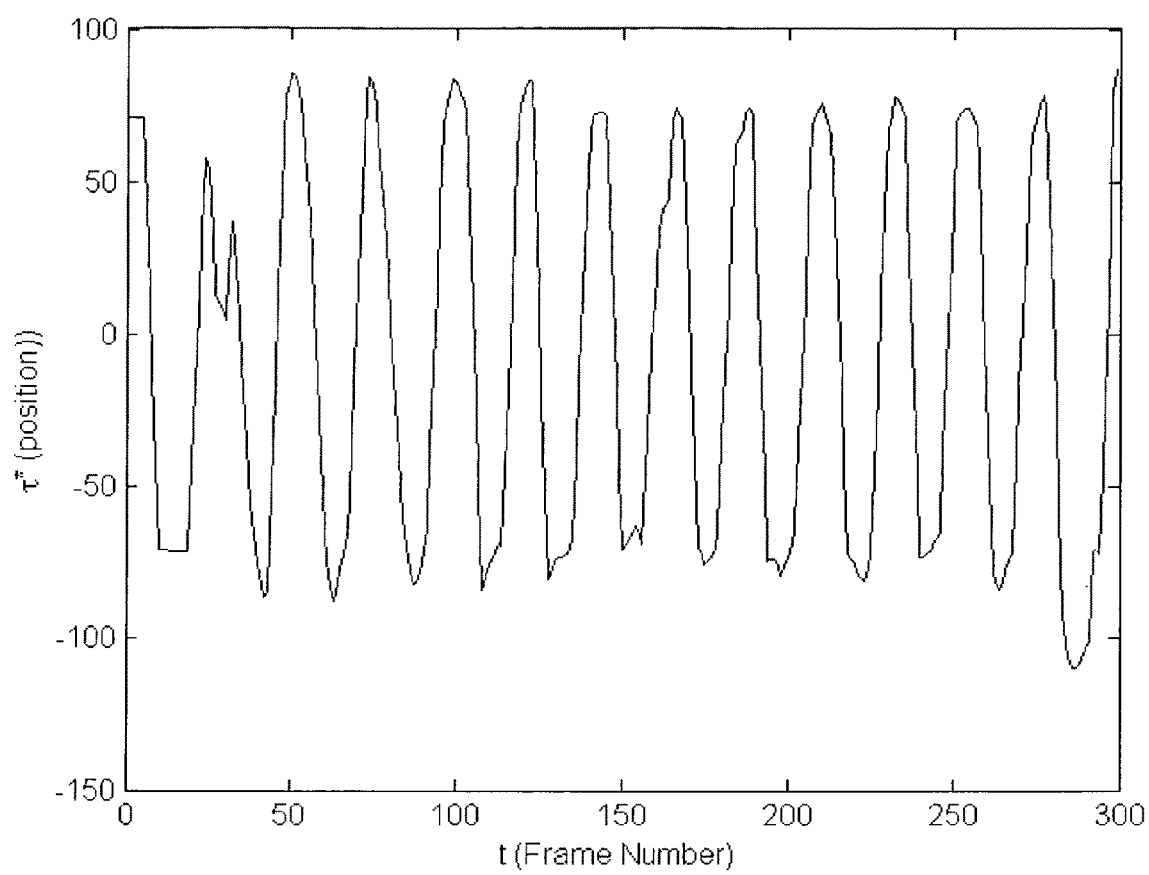
FIGS. 11A and 11B are graphical representations of the periodic left-right shifts (swings in the horizontal direction) estimated by spatial correlations between frames ((FIG. 11A) shifts of a jogging video.
Figure 11B:
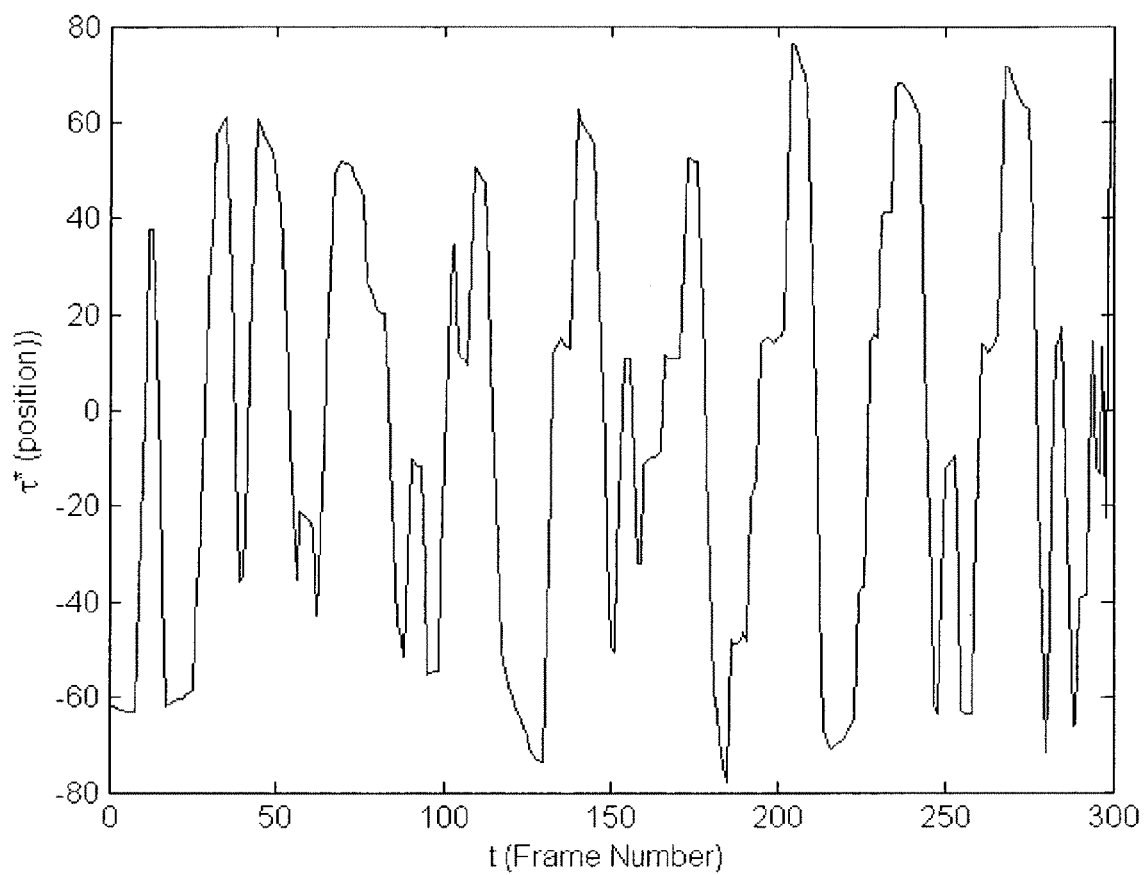

Since this calculation was performed on 1-D vectors, the computational cost was greatly reduced compared to the traditional methods. FIG. 2A is the 20th frame of the walking video 1. We took all the videos from the common living and working places. Some experimental results of the shifts are shown in FIG. 11A for the cases of jogging (FIG. 11A) and walking (FIG. 11B). The positive and negative shifts represent, respectively, the camera swinging to left and right, respectively. It can be observed that both results show the periodic motions between frames with time, each period representing a particular step.

Table 1 shows the results of the gait frequency for both the walking and jogging cases calculated from 6 video clips (about 5,000 video frames). It can be observed that the estimated speeds for walking and jogging were approximately 2.2 steps/second and 2.9 steps/second, respectively. These values, along with the step size and the body weight of the subject, can be utilized to calculate the energy expenditure reflecting these physical activities.

TABLE 1

Walking and Running Gait Frequency Estimation.

| Video sequence | Frequency in X direction (number of strides/second) |
|---|---|
| Walking video 1 | 2.2 |
| Walking video 2 | 2.0 |
| Walking video 3 | 2.2 |
| Walking video 4 | 2.2 |
| Jogging video 1 | 3.0 |
| Jogging video 2 | 2.8 |

We have presented a new multimedia approach to the study obesity by acquiring and analyzing recorded video data. Our investigations have focused on energy assessment, i.e. measurements of the energy intake from foods/drinks and the energy expenditure due to physical activity. We have utilized image and video processing algorithms to obtain these measurements. In the dietary assessment case, we have demonstrated the geometric relationships among the camera, the image plane, and the table plane. From these relationships, we can estimate the actual physical dimensions, which can subsequently be used to estimate the caloric content of foods and drinks. In the physical activity assessment case, we have exploited the body swings during walking and jogging. The speed and distance measurements provide important information to estimate the energy expenditure. Our algorithms are low in computational complexity and suitable for processing large sets of multimedia data.

Example 3

Laser-Based Depth Measurement for Digital Imaging of Close-Up Objects

Most software-based methods for estimating depth of objects in an image require explicit knowledge of intrinsic and extrinsic parameters of the camera. We propose a new depth measurement method using fiducial markers generated on the image by several laser beams. A pinhole camera perspective projection model is presented from which the physical depths of the pixels on an arbitrarily rotated plane are estimated with a high accuracy.

The measurement of depth of an object using still images is an important problem in computer vision. Although a laser range finder can be used to obtain depth data, it is often ineffective when the object is very close to the camera. Here, we present a simple method based on several laser beams emitted at positions near the camera. We assume that the measurement points are on a plane oriented arbitrarily but the fiducial makers produced by the laser beams can be observed from the image. We utilize a pinhole camera perspective projection model to reconstruct the optical path of interested points. We estimate the equation of the target plane based on algebraic geometry of the projection system. Then, we estimate the physical depths of pixels on the determined plane.

Three laser emitters are mounted on a hexagonal plexiglass (polyacrylic) board. In each emitter, a laser diode and a focusing lens are adhered on a small plexiglass panel attached on a curved copper sheet. A small screw is used to adjust the angle of the beam by changing the curvature of the sheet copper. A DC power supply is used to illuminate three laser diodes connected in series. The operating voltage and current of the three laser diodes are 2.1 v and 20 mA, respectively. A small web camera is used to take digital images of objects. A 0.5× 0.5×50 inch brass bar is mounted on the table which facilitates the calibration of distance measurement between the camera and the object.

Figure 12:
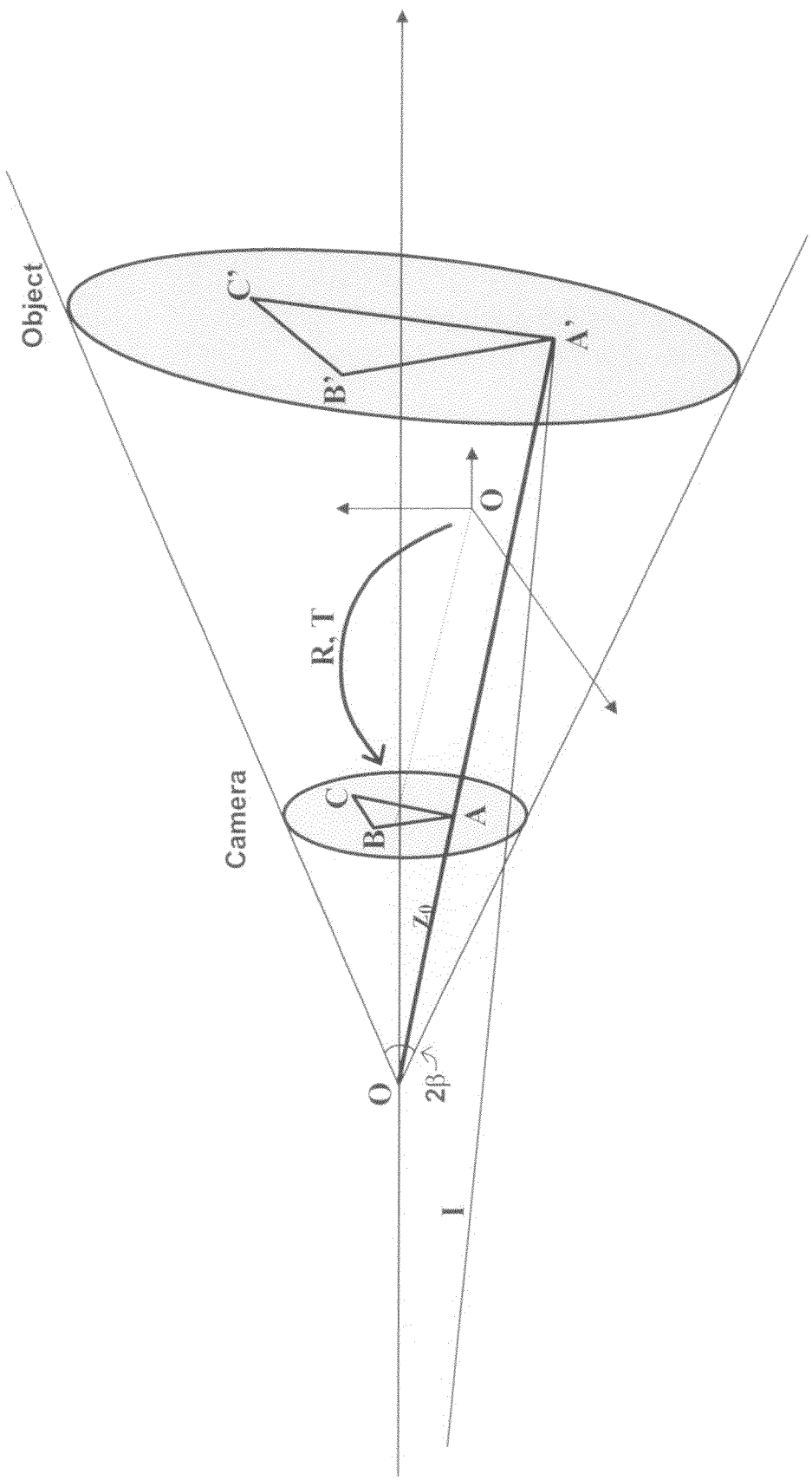
FIG. 12 illustrates the geometric relationship between camera plant, object plane and origin as described in Example 3.
Figure 13:
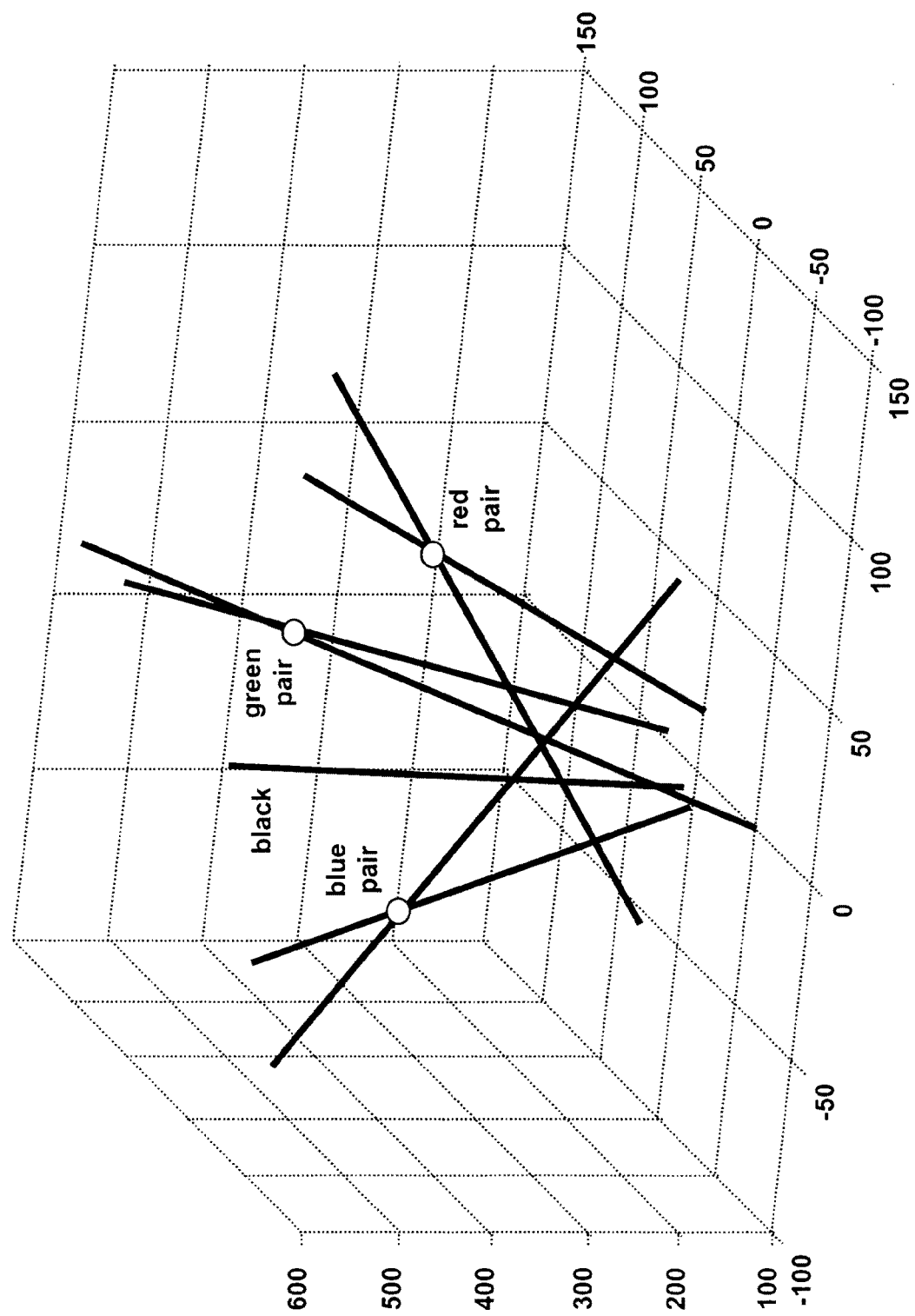
FIG. 13 is a 3D graphical representation of line intersection estimations as described in Example 3.

The optical system model of our system is shown in FIG. 12 where O is the pre-determined origin of world coordinate system. The plane defined by ABC is the camera plane. The center of camera plane is on the optical axis through the camera optical center O'. $2\beta$ is the angle of view of camera and $0z$ is the focal length. A', B', C' are the points of interest on the object plane and A, B, C are their projections on the camera plane. The relation between camera plane coordinate system and world coordinate system can be represented as a rotation matrix R and a translation vector T as following:

$$\begin{bmatrix} X_w \\ Y_w \\ Z_k \end{bmatrix} = R \cdot \begin{bmatrix} X_c \\ Y_c \\ Z_c \end{bmatrix} + T$$

where $(X_c, Y_c, Z_c)$ gives the coordinates of a point in the camera coordinate system and $(X_w, Y_w, Z_w)$ represents the coordinates of the same point in world coordinate system. The rotation matrix R and translation vector T can be obtained by a standard extrinsic calibration method. We utilized a Matlab toolbox provided in (www.vision.caltech.edu/bouguetj/calib_doc/) to compute these parameters. To obtain the equations of the three laser beams of our experimental system, we measured those beams in multiple positions and estimate their line equations using the orthogonal linear regression (OLR) method. The perspective projection paths of O'A, O'B, and O'C are obtained from camera intrinsic calibration. We need only to estimate the intersection points of line I and O'A, line II and O'B, and line III and O'C to obtain the equation of the plane determined by points A', B', C'. Because there exist measurement and estimation errors, generally, two lines do not cross exactly in three-dimensional space. Therefore, a determination of the optimal approximation of the intersection points is necessary. FIG. 13 shows the six spatial lines obtained from laser beam measurements and their perspective projection path estimates. Each color pair represents two cross lines in a non-ideal practical case. The black line is the camera optical axis. To approximate cross points A', B', C', we use an iterative gradient method to search for two closest points on the pair of lines. After we determine the coordinates of the three cross points A', B', C', the plane equation in the three-point form can be obtained.

Experiments

In our experiments, we estimated the depths of both artificial objects (planner patterns) and food objects in arbitrarily oriented flat plates. The performances of physical depth estimates by our system for the artificial objects and food objects are provided in Tables 2 and 3, respectively. Once the depth information is obtained, the food volume can be estimated which is an important step to obtain caloric and nutritional information. Our experimental results indicate an average depth estimation error of less than 5% from the true depth. This error is acceptable in our study on food volume based on imaging processing techniques.

TABLE 2

Depth estimation of artificial objects (unit: millimeter)

| | Distance estimation: | Object physical length estimation |
|---|---|---|
| Parallel plane | Mean of error = 1.9723<br>Mean of Percentage error = 0.44%<br>Std of error = 3.2558<br>Std of Percentage error = 0.76%<br>(16 samples) | Mean of error = −4.2381<br>Mean of Percentage error = 3.79%<br>std of error = 2.5193<br>Std of Percentage error = 2.51%<br>(36 samples) |
| Arbitrary rotated plane | | Mean = −3.6915<br>Mean of Percentage error = 2.44%<br>Std of error = 7.5703<br>Std of Percentage error = 8.31%<br>(24 samples) |

TABLE 3

Food objects depth estimation

| | Bread (13) | Cheese slice (15) | Round steak (12) | Noodle (14) |
|---|---|---|---|---|
| Measured length (mm) | 107 | 76 | 80 | 130 |
| Average estimate length (mm) | 109.2898 | 81.3913 | 81.4064 | 135.1880 |
| Mean of error (mm) | 2.2898 | 5.3913 | 1.4064 | 5.1880 |
| STD of error (mm) | 5.0705 | 4.1381 | 8.0560 | 6.6006 |

Example 4

Automatic Dietary Assessment from Fast Food Categorization

A goal of this research is to develop a system which could assess food intake and energy expenditure automatically and objectively. We are developing a unified, miniature sensor device which combines with a microscopic video camera and other sensors such as an accelerometer, an oximeter, a semiconductor thermistor, and a microphone, etc. The video camera is configured to record the same scene as the wearer perceives. The device will be used for automatically capturing eating/drinking activities as well as physical activities. Besides the hardware, we also need to develop algorithms and tools for processing and analyzing recorded multimedia data. In this paper, we present an approach for automatic dietary assessment from fast food categorization.

Fast food is the food that can be prepared and served quickly. Every day about one quarter of the U.S. population eat fast food. Many fast food restaurants have standardized their food ingredients. Thus, for a given category, we could know its major nutrition facts directly (e.g., calories, fat, etc.). This provides us an easier way for automatic dietary assessment. Instead of analyzing the ingredients, we could obtain the nutrition facts directly from categorizing the food, i.e., from food to calories. Suppose that a subject has worn a video device which has captured the food eaten. If the system can automatically recognize the food with the known ingredients, it knows how many calories the subject has taken. In this way, we can formulate the dietary assessment problem as an object categorization problem. We further employ computer vision and pattern recognition techniques to solve this problem. Below, we describe the main algorithm, present system implementation and the experiment results.

Let I be a test food image and its q-th segment $S_q$, $I_{ic}$ be the i-th training image of the c-th category. Let $\phi(I)$ (or $\phi(s)$) be the signature of image I (or segment S) and $\Omega(I)$ (or $\Omega(S)$) the number of features extracted form image I (or segment S).

Segments are classified based on the nearest neighbor rule. Define the distance of the test segment $S_q$ to class c as:

$$d(S_q, c) = \min_i d(S_q, I_{ic}) = \min_i \|\phi(S_q) - \phi(I_{ic})\|_1. \quad (1)$$

We assign the segment $S_q$ to its closest category $c_1(S_q)$:

$$c_1(S_q) = \underset{c}{\operatorname{argmin}} d(S_q, c). \quad (2)$$

In order to combine segment labels into a unique image label, we define the second best labeling segment $S_q$ first:

$$c_2(S_q) = \underset{c = c_1(S_q)}{\operatorname{argmin}} d(S_q, c). \quad (3)$$

Then we compare the distance of $S_q$ to c1 and c2, defining:

$$p(c_1(S_q)|S_q) = (1 - r) + r/C, r = \frac{d(S_q, c_1(S_q))}{d(S_q, c_2(S_q))}. \quad (4)$$

C is the number of categories. For other labels, $c \neq c_1(S_q)$:

$$p(c|S_q) = \frac{1 - p(c_1(S_q)|S_q)}{C - 1}. \quad (5)$$

Let $\{S_1, \ldots, S_k\}$ be all the segments of a test image I. The label of the food image I is then given by (6):

$$C(I) = \underset{c}{\operatorname{argmax}} \sum_{q=1}^{K} p(c \mid S_q) \omega(S_q), \quad (6)$$

$$\omega(S_q) = \Omega(S_q) / \Omega(S_{\max}),$$

where $S_{max}$ is the largest segment (in number of features).

Experiment Results and Systems

System Implantation for "from Food to Calories"

A miniature digital camera attached to the body is utilized to acquire video data. Once key frames that contain food are extracted from the video sequence, we can then recognize their categories and infer calories from the database. We choose McDonalds® fast food for test because of its popularity, standard production, and detailed nutrition information offered. The nutrition information of McDonalds® food could be easily found from its website (four categories of them are listed in Table 4). We have ignored the volume and content difference between foods in a general category in this experiment. Although this estimation process is coarse, it is the first attempt toward the final goal of automatically dietary assessment.

TABLE 4

Calorie information of some MacDonalds ® fast food

| Menu Item | Calories(C) |
| --- | --- |
| Hamburger | 250 |
| Medium French Fries | 380 |
| Ice Cream Cone | 150 |
| Coca-Cola Classic (Medium) | 210 |

Food Image Categorization Results

Figure 14A:
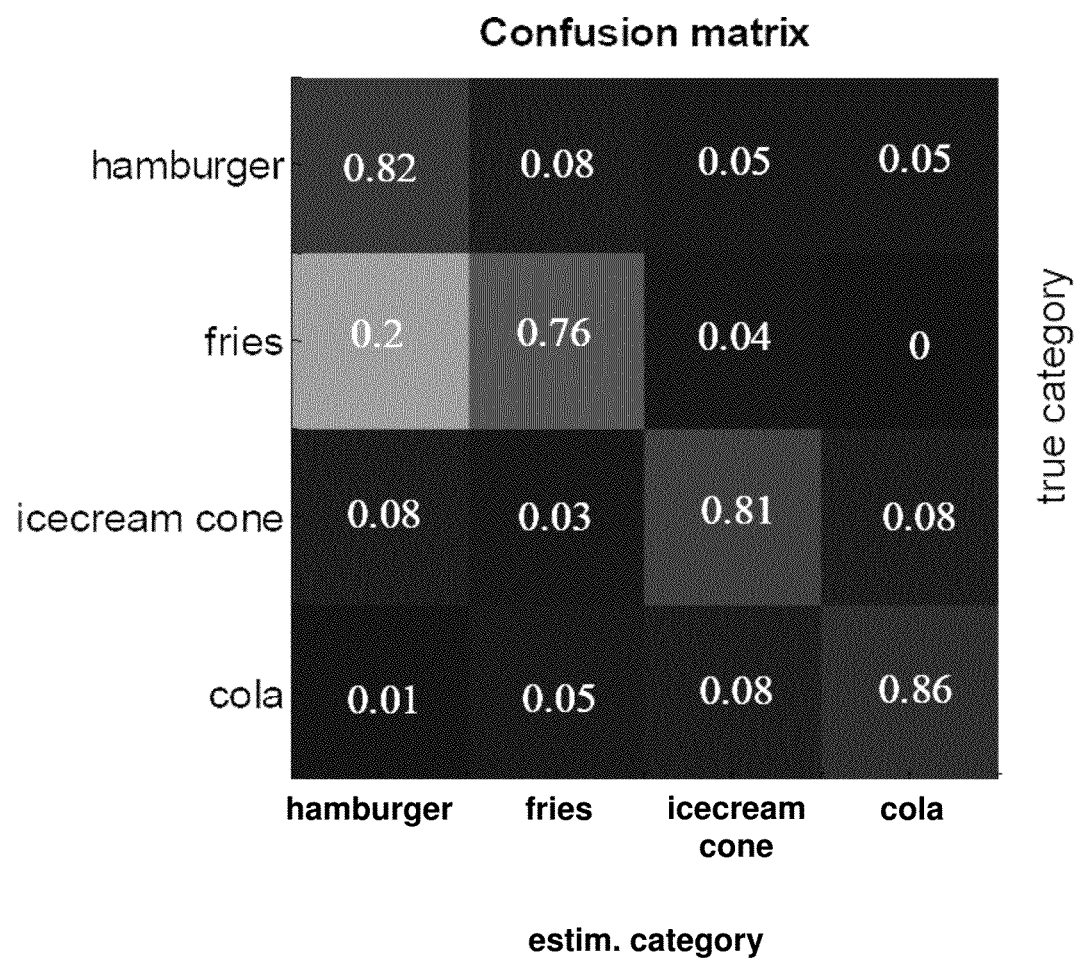
FIGS. 14A and 14B provide experimental results as described in Example 4.
Figure 14B:
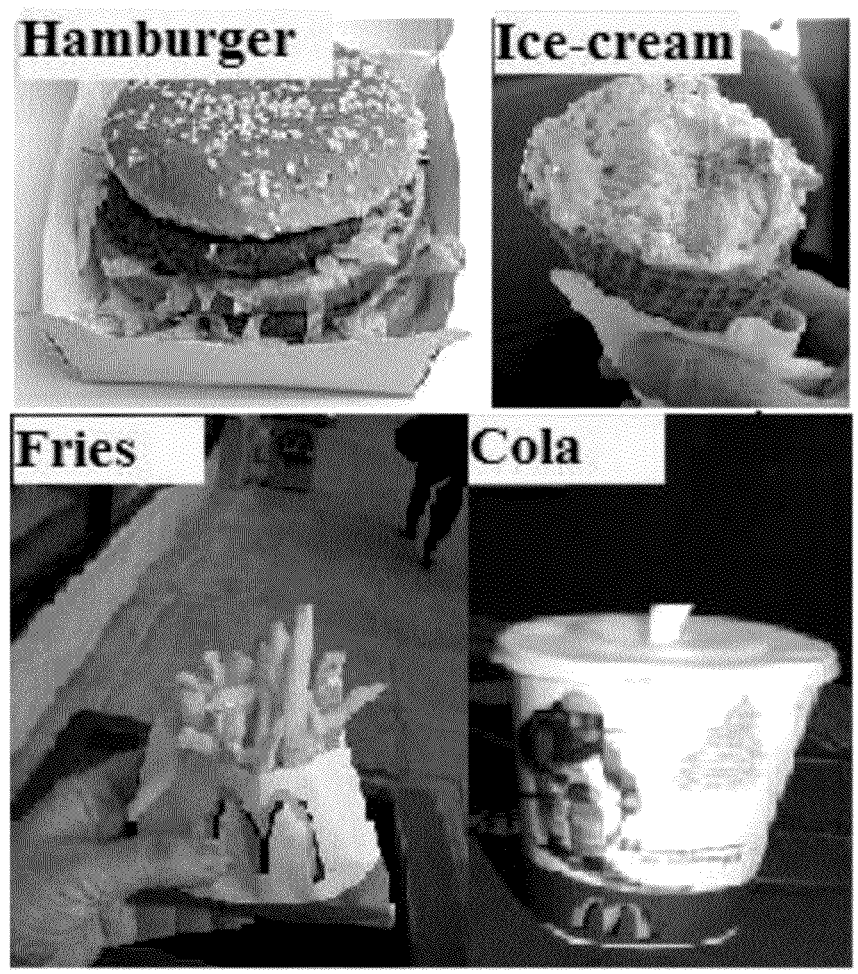

To demonstrate the feasibility of proposed food categorization method, we collect a dataset with four most common fast foods in McDonald®: hamburger, fries, ice-cream cone, and Coca Cola. There are 100 images in each category. Even though the categories of fast foods are small and the database is limited, as our first attempt, the experimental results are encouraging and promising (FIG. 14).

20 images are used for training and the remained 80 images are for test in each category. The statistic results as well as some examples of correctly classified images are shown in FIG. 14. We have achieved an average categorization accuracy of 81.25% in total.

This experiment demonstrates that a system can be designed to assess food intake and energy expenditure automatically and objectively. Together with a unified, miniature sensor device configured to record the same scene as the wearer perceives, the combination will provide reliable information for accurate dietary assessment. We have proposed a novel method for automatic dietary assessment from images. We directly estimated calories of fast food from its category and formulated dietary assessment as an object categorization problem. We used a modified bag of feature model for fast food categorization. We have demonstrated the feasibility of the proposed method in a database of McDonalds® fast food. The improvement of the accuracy of the food categorization algorithm and the inclusion of more categories of food are works in progress.

Example 5

This example describes our preliminary work on privacy protection in video for supporting automatic dietary assessment in obesity studies. We present an approach to protect people's identities and contents on computer screens using object detection techniques. We use the Adaboost algorithm implementation from the OpenCV framework to build a system that allows detection of faces and screens in order to obscure them and make them unrecognizable in the recorded images. We also use some post processing methods to improve the detection accuracy. Our preliminary results show encouraging results. We are currently improving the accuracy and robustness of the system towards a working system.

The advance in hardware and multimedia technologies has made it possible to build up a system that can deal with capturing, representation, organization, analysis, and presentation of temporal streams of data, captured by a patient with body mounted devices in "free-living" conditions for more accurate medical studies. For example, we are developing a unified sensor and electronic chronicle (echronicle) system for ubiquitous "free-living" data acquisition and management in the study of obesity. The device will integrate multiple sensors such as a microscopic video camera, an accelerometer, an oximeter, a semiconductor thermistor, a microphone, etc. The device can be used to capture eating/drinking activities as well as physical activities for obesity patients. Because the video camera is configured to record the same scene as the patient's perspective, we have to address problems of privacy protection for both the patient and other people. For example, the device may capture other people in the scene or the patient's own computer screen when he/she is using a computer. Here, we present our ongoing research of privacy protection in videos to deal with these problems.

Figure 15A:
FIGS. 15A and 15B are modified images as described in Example 5.
Figure 15A:
Figure 15B:
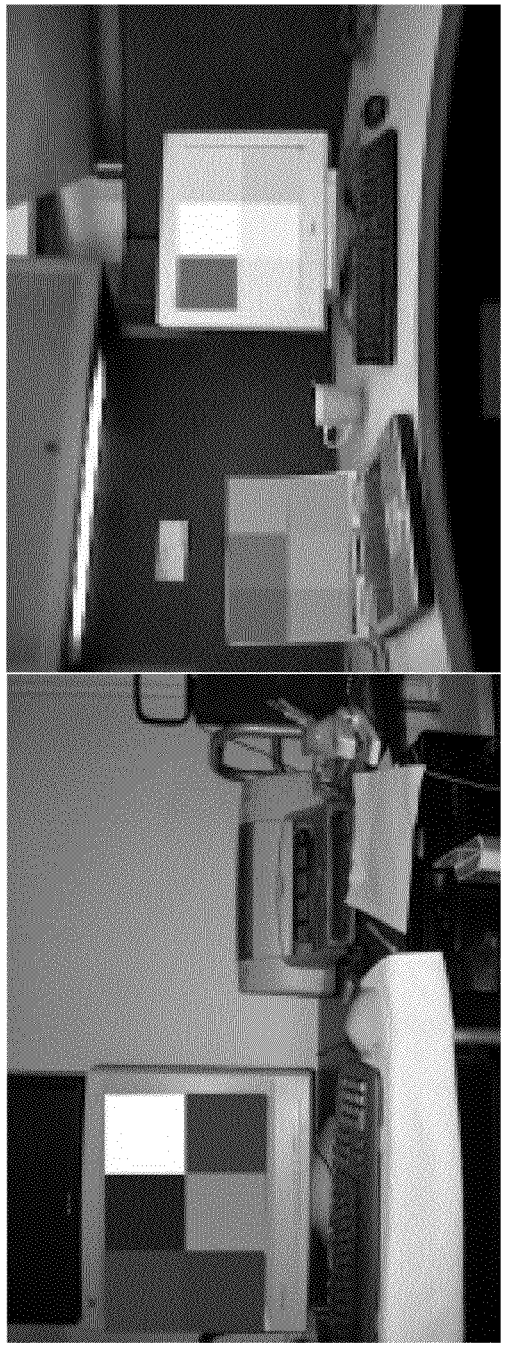
Figure 15B:
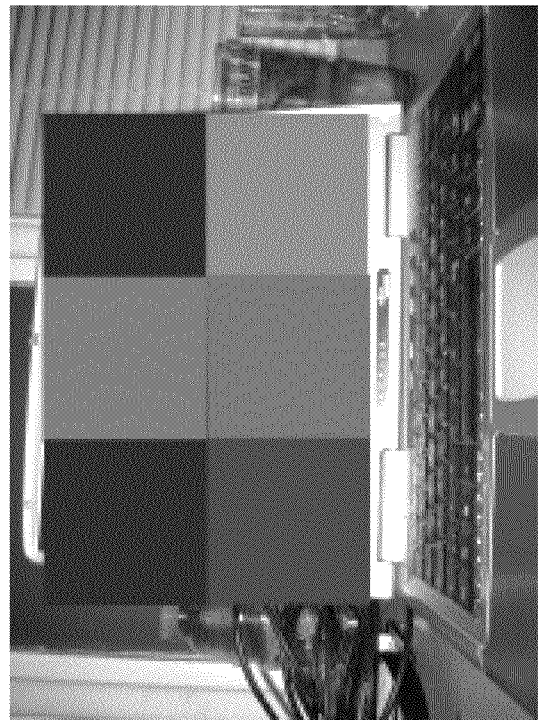

The problem of privacy protection in videos is poorly defined. Privacy could mean different things to different people. In this research, we adopt the common approach in practice that protects the identity of people and the content of objects from being recognized during the video playback. More specifically, we develop techniques to remove people's identities by face obscuring, as commonly seen in television, and to protect the content of computer screens by masking the screens when the screen is close enough (e.g., with a certain size). FIG. 15 illustrates the proposed concept of our system. FIG. 15A shows the results of privacy protection for people and FIG. 15B displays the results of content protection for computer screens. In order to obscure human faces and to mask computer screen, we have to robustly detect human faces and computer screens in images. Thus, the problem becomes an object detection problem in images/video.

Object detection is a fundamental problem in computer vision and pattern recognition: Given an image, to determine whether or not the object is present, and, if present, determine the location and size of each object. A well studied and common used approach for object detection is the Adaboost algorithm introduced by Viola-Jones (P. Viola, M. Jones, "Rapid Object Detection using a Boosted Cascade of Simple Features", CVPR, 2001) and extended by (R. Lienhart, J. Maydt, "An extended set of haar-like features for rapid object detection", IEEE ICIP, pp. 900–903, 2002). The basic idea of the Adaboost algorithm is to build a series of so called weak classifiers that perform slightly better than guessing in classifying. They are represented by connecting rectangles, which define a set of pixels. These pixels' values are summed up. The difference of the sums of the rectangles is then used to separate positive from negative samples, e.g., faces from non faces. By "boosting" a weak classifier as described in P. Viola, M. Jones, "Rapid Object Detection using a Boosted Cascade of Simple Features", CVPR, 2001, a strong classifier is calculated. This strong classifier can be trained using arbitrarily good false alarm rate and hit rate on training data.

We then can use the trained classifier for an object detection task. To detect objects, the input image and its sub images are forwarded to this classifier, which decides whether it contains the trained object or not. According to the position of the sub image, the position of a detected object within the image is found.

We use the OpenCV framework, an open source library maintained by the Intel Corporation, as a tool to implement our system. The OpenCV provides essential data structures and algorithms for computer vision applications. Among these algorithms, Viola-Jones algorithm is implemented and provides training and detection tools such as cvhaartraining.exe and performance.exe. We used these libraries and tools to train the classifier, detect objects in images and test our results.

Face Detection

For training a face detector, we used an optimized face database from other researchers (J. Chen, X. Chen and W. Gao. "Expand Training Set for Face Detection by GA Resampling," 6th IEEE International Conference on Automatic Face and Gesture Recognition, pp. 73-79, 2004). To speed up the training process, small subsets of this large collection were used. Three classifiers will be compared later. Class2000, Class5000 and Class 10k were trained with 2000, 5000, 10.000 face images and 2000, 5000, 5000 images without faces respectively. For evaluation, we used the three collections with upright faces from the CMU+MIT test set for testing the classifiers quality, as most other researchers do. The evaluation dataset contains 191 images with 517 faces.

Figure 16:
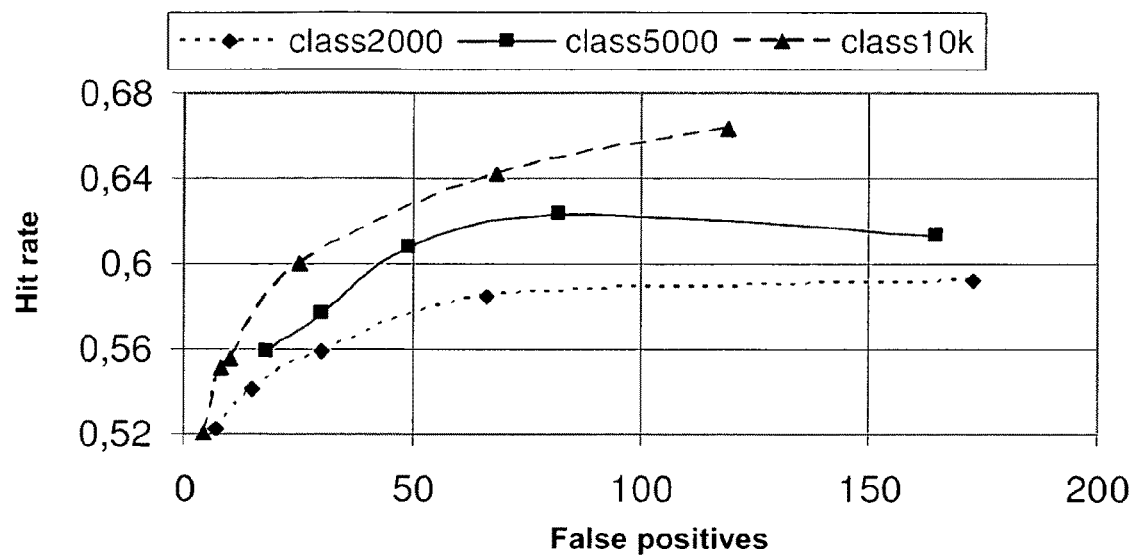
FIGS. 16 and 17 are graphical representations of face detection results as described in Example 5.

The result of these tests is displayed as a roc curve. It describes the amount of falsely positive labeled objects on the x-axis and the percentage of correctly detected objects on the y-axis. The more the curve orients to the top left corner, the better is the classifier. FIG. 16 shows the promising results for our classifiers, as they become better, the more samples are used and as J. Chen, X. Chen and W. Gao. "Expand Training Set for Face Detection by GA Resampling," 6th IEEE International Conference on Automatic Face and Gesture Recognition, pp. 73-79, 2004 reports, very good results using this set for training.

Screen Detection

Figure 17:
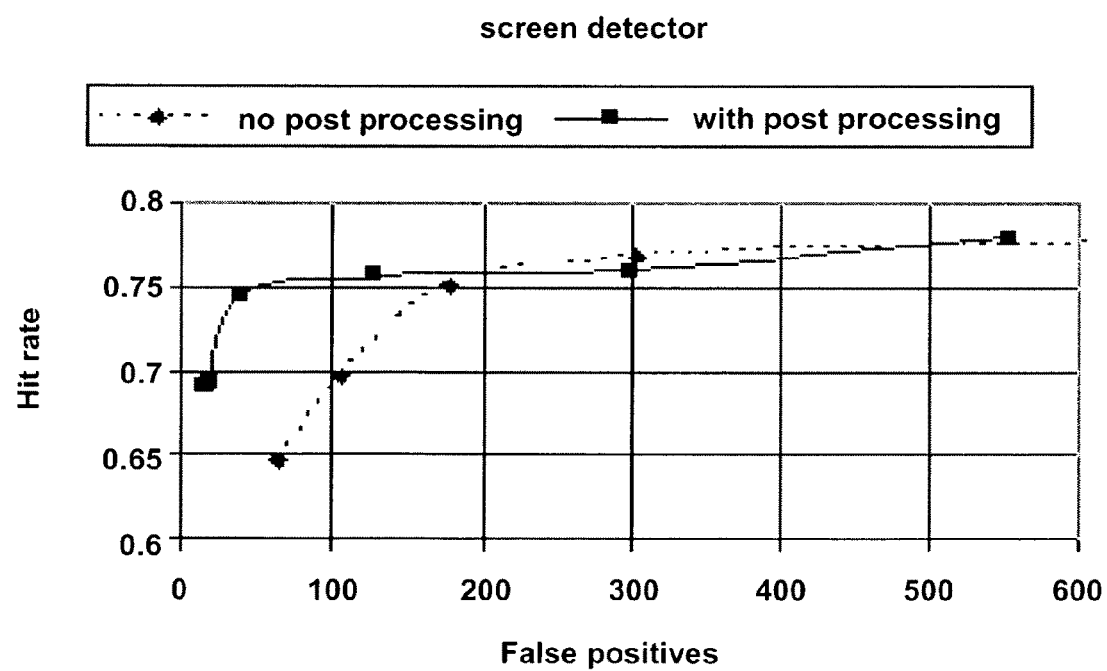

While face detection is a very well researched field, screen detection is nearly not mentioned in literature. Our first attempt is to use the same procedure as we used for faces. Therefore, we collected 1000 screen images and 2800 no screen images on the internet. A preliminary classifier was trained using this collection. The result is a classifier that found a high number of false positives when detecting a reasonable number of objects correctly. To improve this result displayed in FIG. 17, the detected objects are filtered by post processing. Only those objects are considered as correct, which are also found in two of the three previous or following frames. For testing a short video recorded in an office environment was used. This sequence consists of 239 frames containing 314 screens. FIG. 17 shows that most of the correctly detected screens were kept while dismissing many false positives during post processing. The post processing allows a hit rate (correctly found screens divided by all found screens) nearly as well as the classifier alone, but has far less false positives.

Our preliminary work shows that object detection can be used for protecting privacy in videos. Although the described approach can provide robust detection of objects concerning privacy, it needs further improvements for real working systems. The classifiers need to be improved, especially for occluded and rotated objects. For more complete privacy protection, we will work on detecting other objects that may reveal privacy of people, such as text in the scene, and mask them accordingly.

Example 6

Laser Rangefinder

The following is a laser rangefinding method similar to that of Example 3. We investigate a different approach based on laser rangefinding. Although sophisticated rangefinders are available, their bulky size does not fit our miniature device. We use a different design in which several miniature laser diodes emit low-intensity light beams (visible or invisible) from the front of the picture-taking device. These beams produce fiducial markers on food pictures which are then analyzed to obtain the desired physical scale.

In order to simplify the problem, we assume: 1) the food item possesses a certain symmetry (e.g., a banana, a glass of milk, or a hamburger) so that dimensional measure(s) between manually or automatically selected point pairs can be used to estimate the volume; 2) the selected point pairs are within a 2-D measurement plane determined by the fiducial markers.

Figure 18:
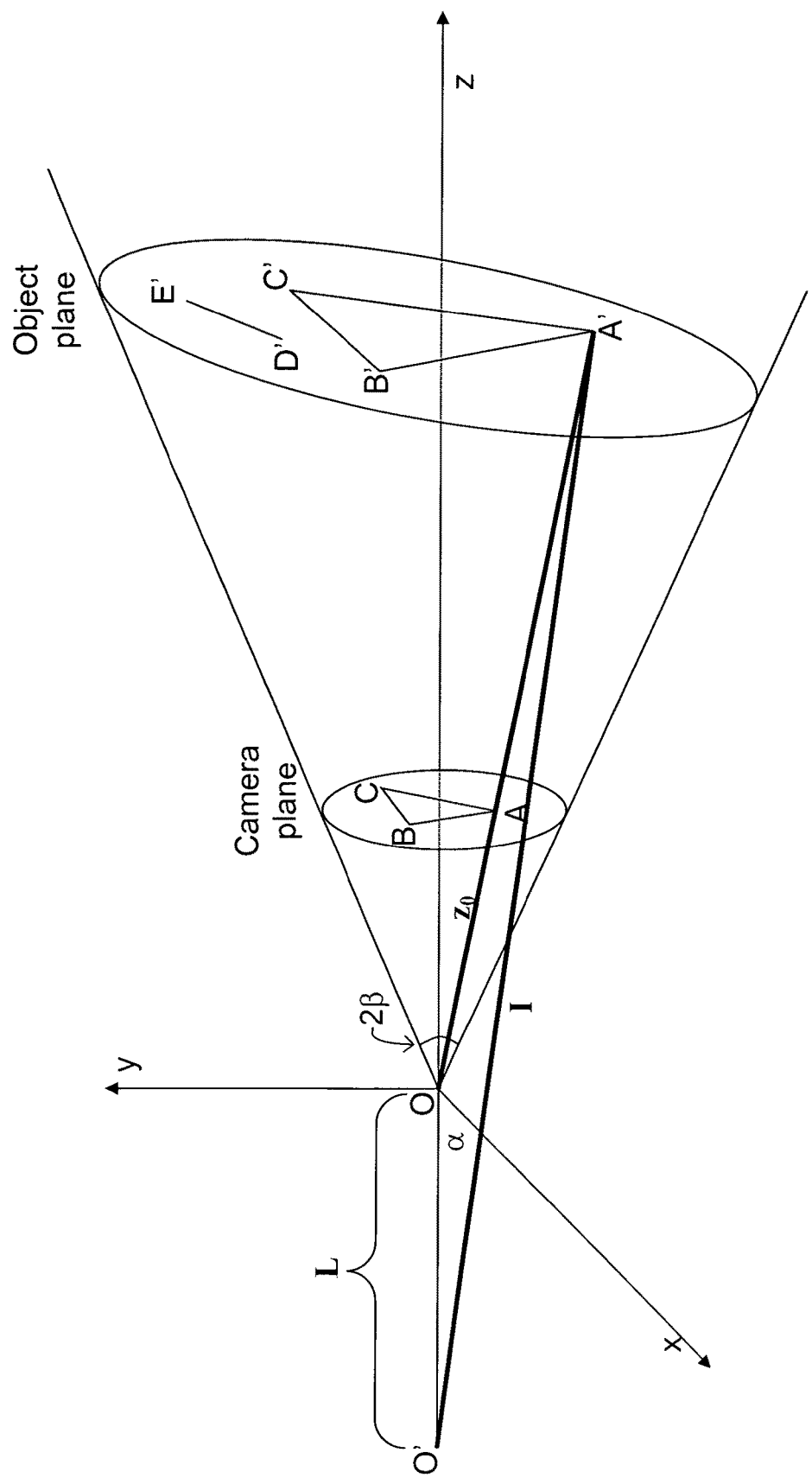
FIG. 18 is a graphical representation of the geometric relationship between laser beam I, camera plane and observed object plane in the world coordinates, as described in Example 6.

The geometric model of a three-diode system involving the laser beams, camera, and measurement plane are shown in FIG. 18. The systems with less or more beams or structured lights can be similarly studied. We let the focus of the camera lens be the world coordinate origin O, the z-axis be the camera capture direction, the camera focal length be $z_0$, and the camera angle of view be $2\beta$. We assume that both the projected image plane $\Delta ABC$ and the physical plane $\Delta A'B'C'$ is in front of the camera focus. Obviously, the equation for the image plane is given by: $z=z_0$.

The three laser diodes are fixed symmetrically and centered at point $O'(0,0,L)$. For simplicity, let the angle $\alpha$ between each of the lights and the z-axis is equal. If the plane intersecting the three beams is perpendicular to the z-axis, the fiducial markers form an equilateral triangle otherwise, in the more general case, there will be a non-equilateral triangle, as the triangle $\Delta A'B'C'$ shown in FIG. 18. Labeling the lines O'A', O'B', and O'C' as I, II, and III and fixing the angle between I and x as $\pi/2$, then, the angle between I and y is $\alpha+\pi/2$. The angles between other lines and axes can be similarly calculated. FIG. 18. shows the geometric relationship between light I, camera plane $\Delta ABC$ and observed object plane $\Delta A'B'C'$ in the world coordinates. D'E' is the physical scale of our interest. Lines II and III have similar geometric relations and they point to points B' and C' respectively.

Since the coordinates of A, B, C can be computed from the pixel-coordinates in the captured images, the equations of lines OA, OB, OC can be obtained from two-point form as $$OA: \begin{cases} x = 0 \\ \dfrac{y}{y_1} = \dfrac{z}{z_0} \end{cases}, \qquad (1)$$

$$OB: \dfrac{x}{x_2} = \dfrac{y}{y_2} = \dfrac{z}{z_0}, \qquad (2)$$

$$OC: \dfrac{x}{x_3} = \dfrac{y}{y_3} = \dfrac{z}{z_0}. \qquad (3)$$

Since the direction vectors of lines I, II, and III are known, the equations of I, II, and III can be obtained from the world coordinates as $$O'A': \begin{cases} x = 0 \\ y = -\tan\alpha(z_0 + L) \end{cases}, \quad (4)$$

$$O'B': \frac{x}{\cos\alpha\sqrt{0.75\cos^2\alpha + 1}} = \frac{y}{\sin\alpha/2} = \frac{z+L}{\cos\alpha}, \quad (5)$$

$$O'C': \frac{x}{-\cos\alpha\sqrt{0.75\cos^2\alpha + 1}} = \frac{y}{\sin\alpha/2} = \frac{z+L}{\cos\alpha}. \quad (6)$$

The points A', B', and C' are the intersections of line pairs OA and I, OB and II, and OC and III. From the above six line-equations, we can compute the coordinates of A', B', and C', and then the equation for plane ΔA'B'C'.

As mentioned previously, D'E' represents the physical length of interest on the plane of triangle ΔA'B'C'. In the image, we can measure the pixel-coordinates of its projection DE. Using the same method, we can obtain the world coordinates of D'($x_{D'}, y_{D'}, z_{D'}$) and E'($x_{E'}, y_{E'}, z_{E'}$). Finally, we calculate D'E' by:

$$|D'E'| = \sqrt{(x_{D'}-x_{E'})^2 + (y_{D'}-y_{E'})^2 + (z_{D'}-z_{E'})^2}. \quad (7)$$

We conducted two experiments to verify our methods. Low-power laser diodes and small polymer lenses were utilized to generate visible laser beams. Conventional image processing methods were used to segment and extract laser-highlighted points and the image objects.

Figure 19A:
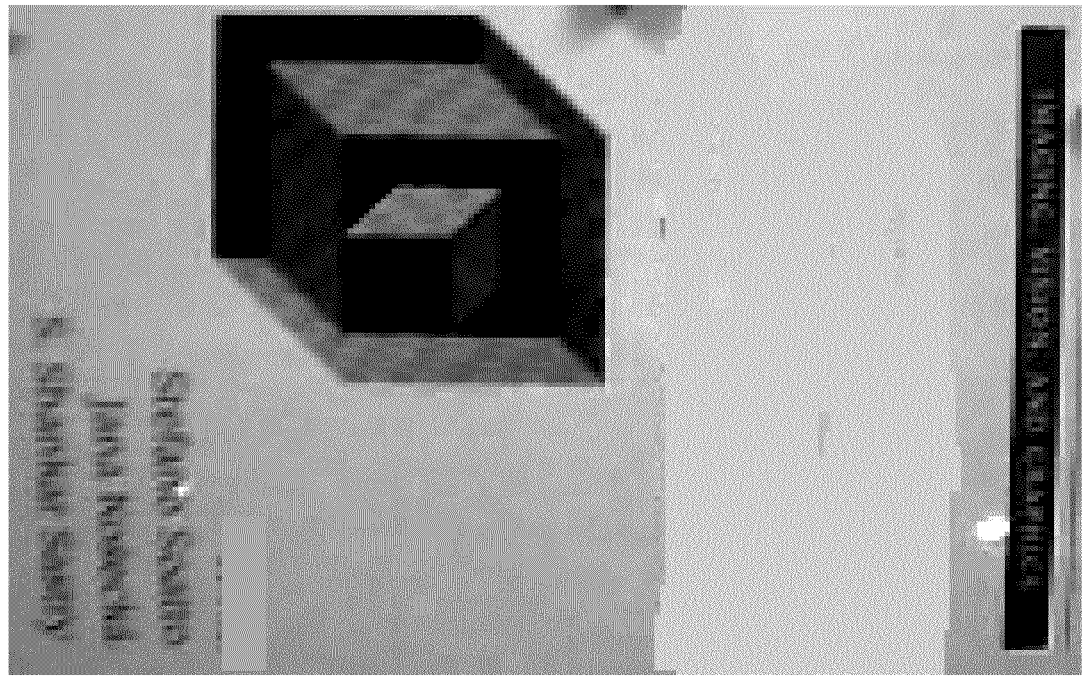
FIGS. 19A and 19B are images with laser highlights as fiducial markers, as described in Example 6.

In the first experiment, we used two parallel laser diodes. We arranged the object (a cube figure on a book's cover) at 12 different locations 50 cm to 100 cm from the camera. FIG. 19A shows the image captured at 60 cm away from the camera. The estimated object dimensions in the horizontal direction by our method were {4.2562 4.2396 4.1899 4.1697 4.2602 4.2764 4.4203 4.4036 4.5177 4.5572 4.7328 4.7788 (cm)}. The average length estimated was 4.4 cm with covariance 0.0429 versus the object's true length of 4.6 cm.

Figure 19B:
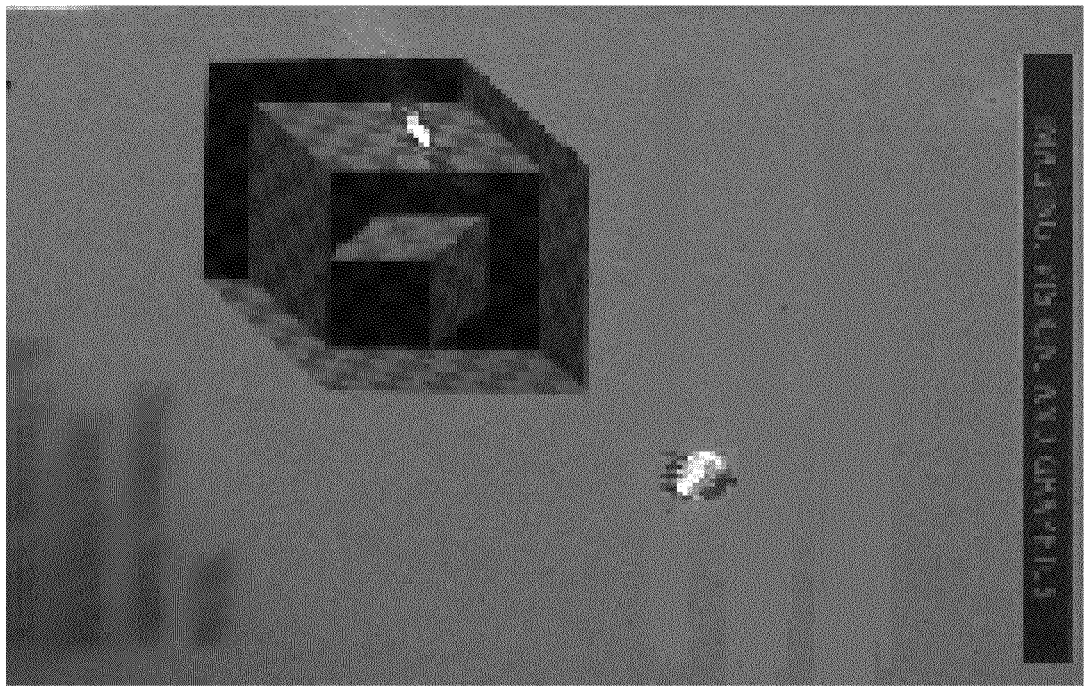

In the second experiment, we used three laser diodes fixed around the camera. The fiducial markers produced by three laser beams were clearly observable on the object plane (FIG. 19B. With the knowledge of the positions of the diodes and the camera optical center, we were able to use our model described above to assess the effects of arbitrarily rotated plane on the calculated dimensions of test objects.

We have presented a design of a simple laser rangefinder for measurement of food dimensions. A mathematical model is presented which forms the theoretical basis of this design. In general, the volume of an object cannot be determined completely by one 2-D image or a small number of images. In the case of food, however, exceptions exist. In many cases, the food object or its container has a known shape which possesses a certain form of symmetry, such as an apple, a hamburger, or a glass of milk. Therefore, based on the knowledge of food shapes and our formulas, the volume of certain foods can be determined by several mouse clicks on a single or several food images.

Example 7

Load Measurement Based on Gait Analysis

The study of the relationship between load carrying and gait variation of a walking person is important in many applications, such as biometric human identification and postural analysis for children and the elderly. Here, we present a method to estimate the carried weight from an image sequence. Our estimation method is based on the relationships among the carried weight, leaning angles, body weight, and the position of the load. Our method has been verified successfully by experiments consisting of 57 video recordings.

Gait analysis has been an active domain of research. A variety of techniques have been reported (Sarkar, S., Phillips, P. J., Liu, Z., Vega, I. R., Grother, P., Bowyer, and K. W., "The humanID gait challenge problem: data sets, performance, and analysis," Pattern Analysis and Machine Intelligence, IEEE Transactions on Volume 27, Issue 2, pp: 162-177 February 2005). Most of these techniques have focused on gait recognition, human identification, tracking and behavior analysis. The effects of the carried load on gait have been studied using image processing techniques (Id.) for the purpose of understanding how the carried load influences the result of gait recognition, rather than using gait analysis to determine the carried load. Research also exists which relates gait features to blood pressure, breathing, and walking speed for medical evaluation (Daniel H. K, Alexander C. K, Au-Yang "The effect of backpack load on the gait of normal adolescent girls", Ergonomics, Vol. 48, No. 6, 15 May 2005, 642-656). In contract, our study aims to compute the carried weight from gait measurements.

We approach the problem by investigating human kinetics and estimating the carried weight based on a recorded image sequence from which gait features are extracted. We analyze the person's centroid locomotion, assuming a rigid body kinetic model and a simplified mass distribution of the upper human body. A reference balance support point is selected to estimate the carried weight. Our experiments have verified the effectiveness of this approach.

Previous studies indicate that human walking includes a swing phase and a stance phase and that the normal gait is adjusted automatically to maximize energy efficiency (Mark W. Spong, and Francesco Bullo, "Controlled Symmetries and Passive Walking," IEEE Transactions On Automatic Control, Vol. 50, No. 7, July 2005). Based on these findings, we assume the following: 1) the gait varies naturally reflecting the effects of the load and the balance of the body; and 2) the input image data sequences are human silhouettes (generally binary) after applying simple image processing techniques to the raw data.

Naturally, a non-trivial load carried by a person can cause significant changes in the human posture. Among these changes, the variation in truncal leaning are particularly important, since it is the most energy-efficient way that one uses to keep his/her body balanced. Therefore, we estimate this parameter from the image sequence data.

Figure 20A:
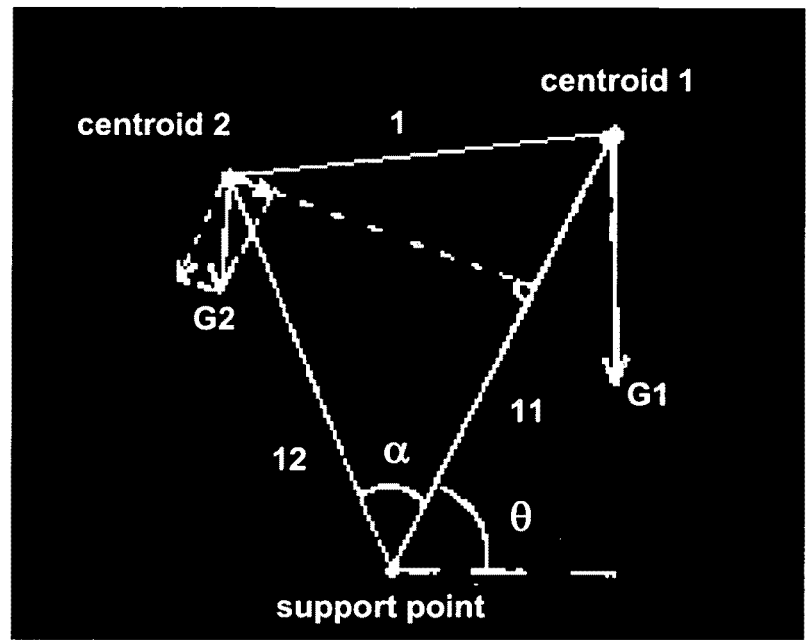
FIGS. 20A and 20B provide illustrations of a model used in gait analysis as described in Example 7.
Figure 20B:
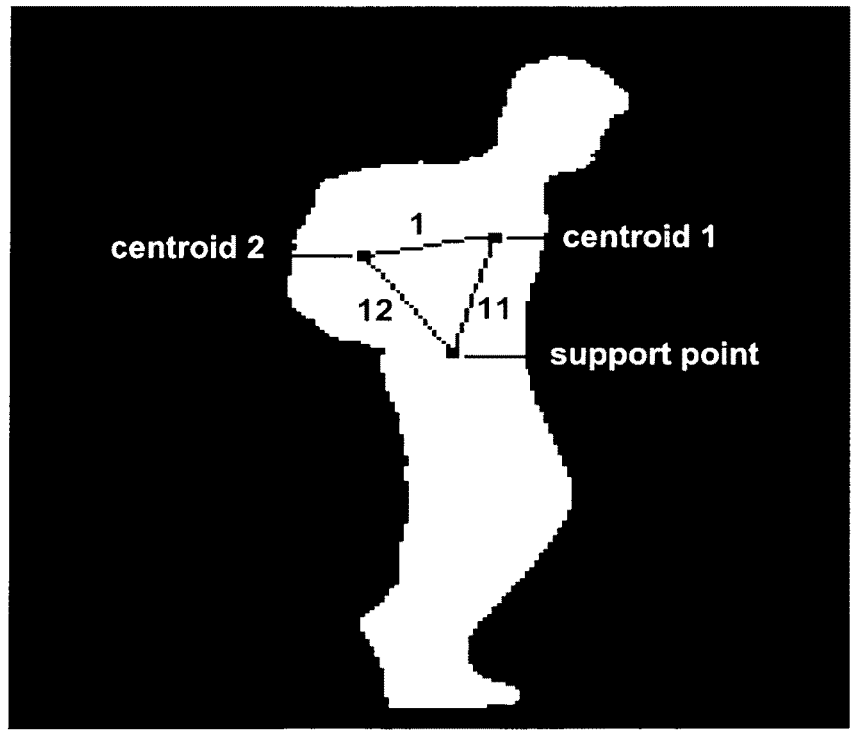

Observation and experimental studies on walking have shown that the upper body is relatively stable during walking except that repetitive motions of the arms are involved. Based on these findings, we constructed a simple model shown in FIG. 20 where G1 and G2 represent, respectively, the gravitational forces of the upper body above the waist and the carried load, centroid points 1 and 2 represent, respectively, the centers of gravity of the upper body and the carried load, and θ is the truncal leaning angle described previously. Our experimental study has shown that the determination of the support point (indicated in FIG. 20A) is very important. We found that it is effective to choose this point to be the midpoint of the waist in the side silhouette (see FIG. 20B). This point can be obtained by image processing.

According to a mechanical principle that governs the fixed-axis rotation of a rigid object, the total torque at the support point is given by $$J_z * \frac{d\omega}{dt} = \sum_{i=1}^{n} M_i \quad (1)$$

where dω/dt represents the angular acceleration, $J_z$ is the moment of inertia, and $$\sum_{i=1}^{n} M_i$$

represents the total torque.

Because the stance of the upper body segments is relatively stable, we can reasonably assume that centroids 1 and 2 have zero angular acceleration with respect to the support point. Then, $(\Sigma_i^n M_i=0)$. Using the differential equation of fixed-axis rotation for a rigid body, we can obtain the following relation based on the model show FIG. 20A:

$$G_1 * \cos\theta * l_1 = G_2 * l_z \cos(\pi - (\theta + \alpha)) \quad (2)$$

From Eq.(2), the leaning angle is given by $$\theta = \tan^{-1}\left(\frac{1}{G_2} * \frac{G_1 * l_1}{\sin\alpha * l_2} + ctg\alpha\right) + c \quad (3)$$

TABLE 5

Comparison between the actual and computed loads.

| Load/kg | | 0 | 1.3 | 2.2 | 3.1 | 4.2 | 5.3 | 6.3 | 7.8 | 8.8 | 10.3 | 11 | 11.6 |
|---|---|---|---|---|---|---|---|---|---|---|---|---|---|
| Computational | A1 | 0.6 | 1.5 | 1.6 | 2.3 | 4.6 | 5.7 | 6.6 | 7.1 | 8.1 | 10.8 | 11.9 | 12.7 |
| load/kg | B2 | 0.5 | 1.4 | 1.5 | 2.5 | 4.5 | 5.4 | 6.6 | 7.7 | 8.2 | 10.7 | 11.8 | 12.5 | where c is a modification factor, which, under certain conditions, is a constant. We write $\theta = \tan^{-2}(k)$, with k representing the slope of the support point to centroid 1.

We use the following steps to estimate load G2:

Compute parameters $l, l_1, l_2$ (shown of FIG. 20A) using the Euclidian distance formula $$d = \sqrt{(x1-x2)^2 + (y1-y2)^2} \quad (4)$$

where (x1,y1) and (x2,y2) are the end points.

Compute parameters α:

$$\alpha = \cos^{-1}\left(\frac{l_1^2 + l_2^2 - l^2}{2 * l_1 * l_2}\right) \quad (5)$$

Compute G1, centroids 1 and 2:

G1 and centroid 1 are determined by human tissue properties of the upper body (Xiao Hui, HUA Dong-Hong, Liu Wei and Zheng Xiu-Yuan, "A brief introduction of national standard of the people's republic of china 'mass center of Chinese adults'," Proceedings of the 20th Annual International Conference of the IEEE Engineering in Medicine and Biology Society, Vol. 20, No 6, 1998). Although these properties are complex, in our case, requiring their accurate description is unnecessary. Thus, we assume that the mass of the tissues is a constant. Then, centroid 2 can be computed by:

$$X = \frac{\sum_{1}^{N} f(i,j) \times i}{\sum_{1}^{N} f(i,j)} \quad (6)$$

$$Y = \frac{\sum_{1}^{N} f(i,j) \times j}{\sum_{1}^{N} f(i,j)}$$

where x and Y represent the position of centroid 2, f (i, j) represents the pixel value at position of (i, j) which, in our case, is either zero or a constant, and N is the number of pixels of the upper body. After all the parameters are computed, the relationship between G2 and θ can be established.

Figure 21A:
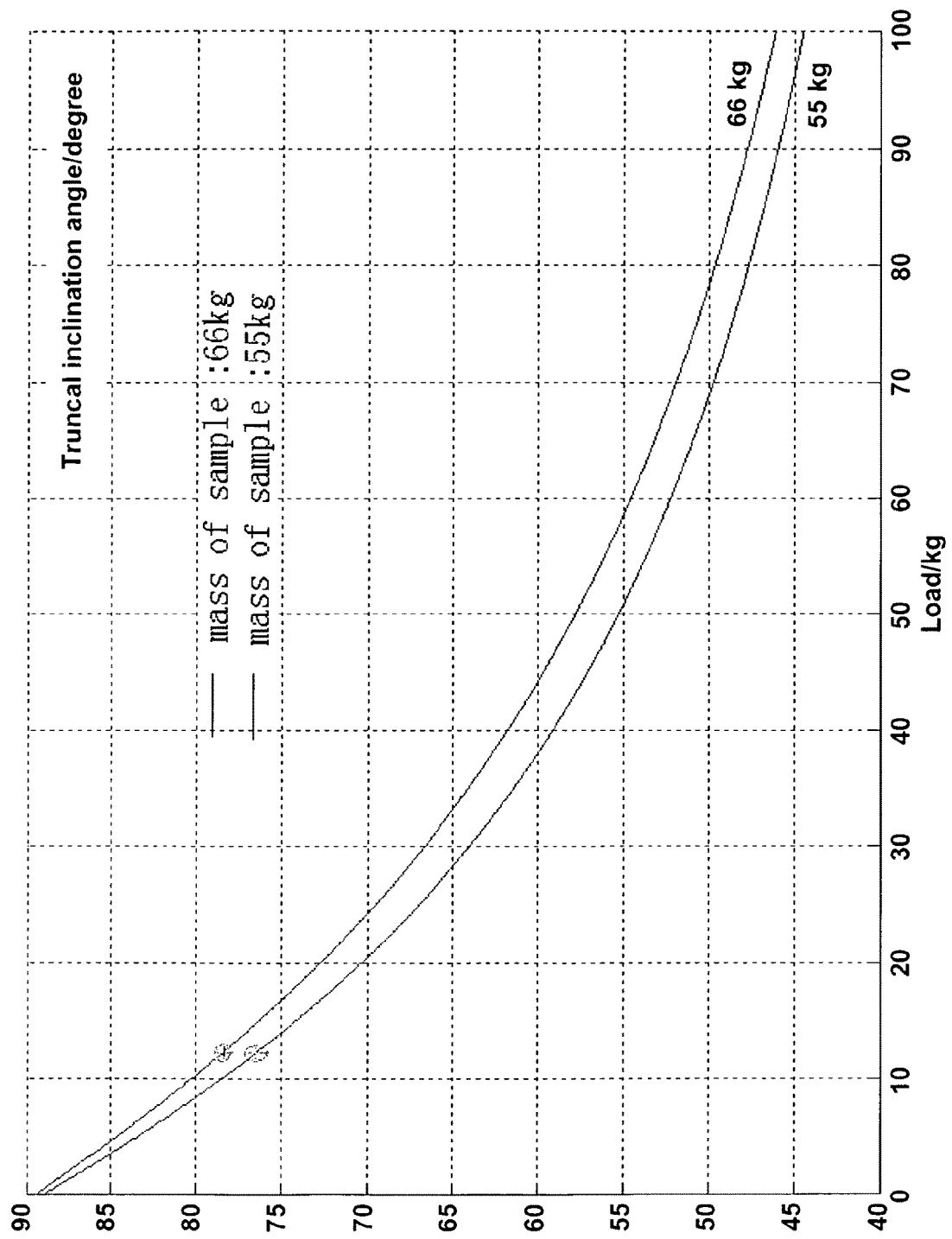
FIGS. 21A-21C provides theoretical (FIG. 21A) and empirical (FIGS. 21B and 21C) results of load studies described in Example 7.
Figure 21B:
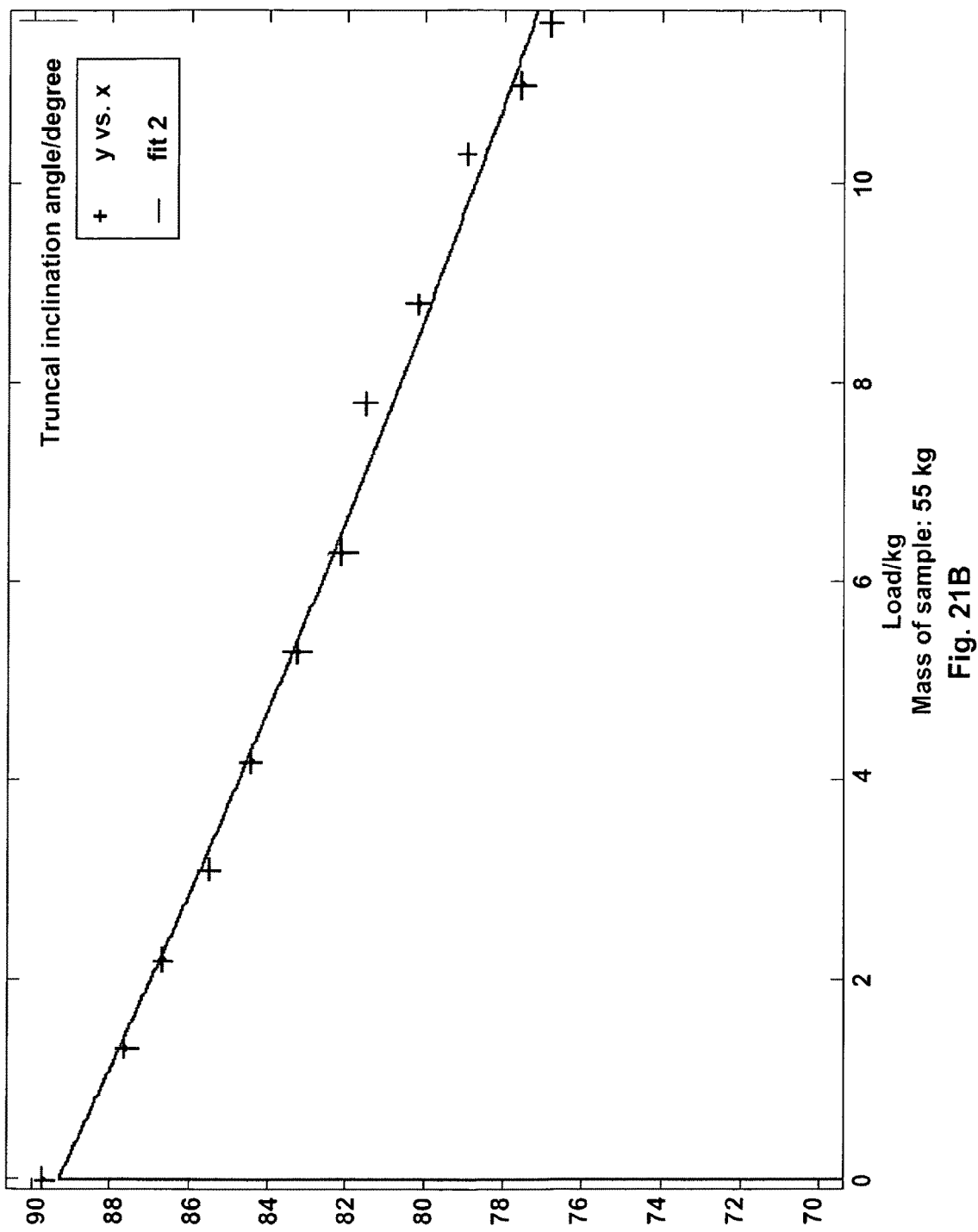
Figure 21C:
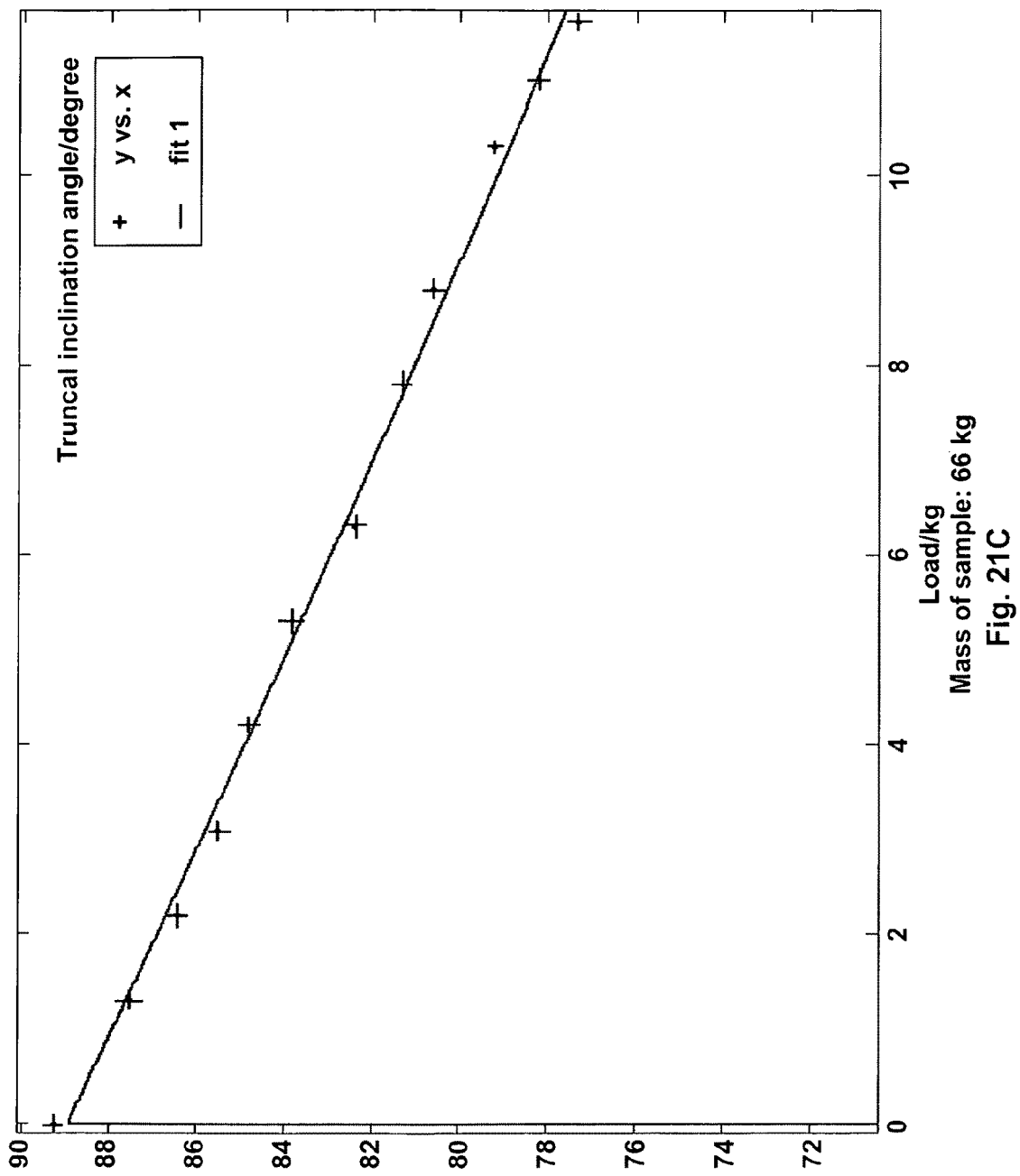

Using 57 individually recorded walking video sequences of two human subjects; we estimated the weight of a backpack that each subject carries. The results are shown in Table 5 which indicates that our method worked well. In order to further verify the validity of Eq. (3), we used actually measured values to obtain the load vs. the leaning angle curve. Our numerical fitting produced the following empirical equations:

$$\text{For Subject 1 } \theta(g) = \tan^{-1}\left(0.5311 + \frac{48.25}{g}\right) - 0.7153 \quad (7)$$

$$\text{For Subject 2 } \theta(g) = \tan^{-1}\left(0.1931 + \frac{56.3}{g}\right) - 1.097 \quad (8)$$

where θ(g) and g represent the leaning angle and the carried load, respectively. The body weights of the two human subjects were 55 kg and 66 kg respectively. The results from Eqs. (7) and (8) are shown in FIGS. 21A-21C. The similarity between the theoretical result (FIG. 21A) and the empirical results ((FIGS. 21B and 21C) which correspond to a portion of (FIG. 21A)) can be observed. Note that, besides the carried weight, the truncal leaning angle is also affected by the position of the carried load, body weight and body shape since G1, centroid 1 and the support point are mainly determined by the body shape.

Here, we have presented an efficient method to compute the carried load of a walking person based on the differential equation of fixed-axis rotation of a rigid object. The waist detected by imaging processing was used to determine a support point. By computing the balance of toques, we successfully estimated the carried weights from 57 video sequences of two walking subjects. Our experimental results indicate that our estimation method is reasonably accurate.

Example 8

Swallowing and Respiratory Event Detection

We have performed a series of experiments to detect swallowing and respiratory events using portable electronics. A miniature microphone was used to acquire both types of physiological data. The choice of a microphone over an accelerometer was because our experiments showed that the microphone provided more balanced sensitivity to both types of signals, while the accelerometer was more sensitive to swallowing than respiration. We designed a small double-sided PCB board and installed an amplifier, a cascade of filters, and a microphone on the board. This miniature device was affixed to the lower neck to acquire data. The gain and the cut-frequencies of the filters were adjusted experimentally to maximize the signal-to-noise ratio. Our results showed that swallowing and breathing signals have different spectral characteristics. The swallowing signal has sharper spectral peaks, while the breathing signal is more evenly distributed along a wide range of frequencies. Using this difference and taking advantage in physiology that these two events never overlap, we were able to identify and separate these two events reliably unless the recorded data were very noisy. We have also studied the noise effect of speech signals on event detection and found that most speech signals are identifiable using spectral characteristics.

We claim:

1. A system for remote monitoring of food intake and physical activity in a human subject, comprising:
    a device for remote monitoring of food intake and physical activity in a subject comprising
        a housing having a first side and a second side, wherein when the device is worn by the subject, the first side is proximal to the subject and the second side is distal to the subject;
        one or more physiological sensors contained within the housing, contained within or connected to the housing, wherein the physiological sensors are selected from the group consisting of a microphone, an oxygen saturation sensor, a heart rate monitor, and an electrode;
        a sensor for determining location, the sensor contained within the housing;
        a motion sensor contained within the housing;
        a video camera contained within the housing;
        a data transfer interface contained within the housing and connected to the sensors and the video camera; and
        one or more power supplies contained within the housing;
    a computer; and
    a data communication device for transmitting data obtained from the device to the computer,
    wherein the computer is programmed or configured to perform a process for recognizing a swallowing event by a person wearing the device and turning on video recording by the device when data is received by the device that corresponds to a swallowing event, the computer also programmed or configured to perform one or more processes for recognizing a food item, recognizing a physical activity, and determining a dimension of a food item in video data obtained from the video camera and for characterizing or quantifying physical activity of a subject wearing the device in data obtained from one or more of the video camera, the physiological sensor, the sensor for determining location, and the motion sensor.

2. The system of claim 1, in which the device further comprises one or more environmental monitoring sensors or an optical sensor connected to the data transfer interface.

3. The system of claim 2, in which the environmental monitoring sensors include one or more of a light sensor for assessing whether the device is located indoors or outdoors and a thermometer and a humidity sensor for monitoring weather conditions.

4. The system of claim 1, in which the computer is further programmed or configured for distinguishing data associated with food and drink consumption from other data obtained from one or both of the microphone and motion sensor; and a process for distinguishing data associated with physical activity from other data obtained from the device.

5. The system of claim 1, further comprising a database comprising dietary information for different foods, and a computer process for determining nutritional information from the computer processes for recognizing a food item and for determining a dimension of a food item in video data obtained from the video camera.

6. The system of claim 1, wherein the data transfer interface comprises a device for storing data on storage media located within the housing of the device for storing data from the physiological sensors and video camera.

7. The system of claim 1, further comprising a controller unit for processing data acquired from the one or more physiological sensors and video camera and for managing the data acquisition of the sensors and video camera.

8. The system of claim 1, in which the video camera can be turned on and off by the subject.

9. The system of claim 1, in which the physical activity of the subject is determined by comparing data from the physiological sensors to predetermined activity correlated variables defining specific physical activities.

10. The system of claim 1, comprising:
    one or both of a motion sensor and a heart rate sensor within or connected to the housing and connected to the data transfer interface;
    sensor for determining location within the housing and connected to the data transfer interface;
    one or more environmental monitoring sensors within the housing and connected to the data transfer interface;
    an optical sensor within the housing and connected to the data transfer interface;
    an oxygen saturation sensor connected to the housing and the data transfer interface;
    a controller unit which manages the acquisition of data from the sensors; and
    a data storage device for storing data on storage media connected to the sensors and the video camera;
    wherein the data transfer interface is connected to the data storage device for transferring data to an external source.

11. The system of claim 1, in which the system comprises a process for recognizing a physical activity and data from the motion sensor corresponding to the physical activity triggers recording from the video camera.

12. The system of claim 1, in which the first side of the housing comprises an acoustic coupling portion, the device comprises a microphone acoustically coupled to the first side of the housing, and data from the microphone corresponding to a swallowing event triggers recording from the video camera.

13. The system of claim 1, further comprising a data encryption process for encrypting data obtained from the device.

14. The system of claim 1, further comprising a process for obscuring facial features of a person in video data obtained from the video camera.

15. The system of claim 1, in which the motion sensor is an accelerometer.

16. The system of claim 1, in which the sensor for determining location is a global positioning sensor.

17. The system of claim 1, in which the computer is programmed or configured to recognize a physical activity by correlating one-dimensional vectors.

18. The system of claim 17, in which the computer is programmed or configured to recognize physical activity by cross-correlating the one-dimensional vectors, using the algorithm:

$$R_{i,j}(\tau) = \begin{cases} \dfrac{1}{N+\tau} \sum_{n=1}^{N+\tau} p_i(n) p_j(n-\tau), & -N < \tau < 0 \\ \dfrac{1}{N-\tau} \sum_{n=\tau+1}^{N} p_i(n) p_j(n-\tau), & 0 \leq \tau < N \end{cases}$$

wherein N is the length of horizontal projection vectors for each frame captured using the video camera; $\tau$ is the shift between two horizontal projection vectors; $p_1$ and $p_j$ are projections of frames i and j respectively, with t=1, 2, ..., j=1, 2, ... M, and M is the number of frames in one video clip.

* * * * *

UNITED STATES PATENT AND TRADEMARK OFFICE
CERTIFICATE OF CORRECTION

PATENT NO.       : 9,198,621 B2                                    Page 1 of 1
APPLICATION NO.  : 12/141741
DATED            : December 1, 2015
INVENTOR(S)      : John Fernstrom et al.

It is certified that error appears in the above-identified patent and that said Letters Patent is hereby corrected as shown below:

In the claims

Column 47, Line 26, Claim 18, delete "$p_1$" and insert -- $p_i$ --

Column 47, Line 27, Claim 18, delete "t=1," and insert -- i=1, --

Signed and Sealed this
Ninth Day of August, 2016

Michelle K. Lee
*Director of the United States Patent and Trademark Office*